US012624012B2

(12) United States Patent
Xie et al.

(10) Patent No.: US 12,624,012 B2
(45) Date of Patent: May 12, 2026

(54) 14-CHLORO-β-ELEMENE NITRIC OXIDE DONOR DERIVATIVE AND PREPARATION METHOD AND USE THEREOF

(71) Applicant: HANGZHOU NORMAL UNIVERSITY, Hangzhou (CN)

(72) Inventors: Tian Xie, Hangzhou (CN); Renren Bai, Hangzhou (CN); Xiangyang Ye, Hangzhou (CN); Junlong Zhu, Hangzhou (CN); Ziqiang Bai, Hangzhou (CN)

(73) Assignee: Hangzhou Normal University, Hangzhou (CN)

( * ) Notice: Subject to any disclaimer, the term of this patent is extended or adjusted under 35 U.S.C. 154(b) by 103 days.

(21) Appl. No.: 18/257,371

(22) PCT Filed: Sep. 2, 2022

(86) PCT No.: PCT/CN2022/116672

§ 371 (c)(1),
(2) Date: Jun. 14, 2023

(87) PCT Pub. No.: WO2023/061095

PCT Pub. Date: Apr. 20, 2023

(65) Prior Publication Data

US 2024/0132456 A1 Apr. 25, 2024

(30) Foreign Application Priority Data

Oct. 11, 2021 (CN) .......................... 202111180424.7

(51) Int. Cl.

| | |
|---|---|
| ***C07D 271/08*** | (2006.01) |
| ***A61P 35/00*** | (2006.01) |
| ***C07D 413/12*** | (2006.01) |

(52) U.S. Cl.

CPC ............ *C07D 271/08* (2013.01); *A61P 35/00* (2018.01); *C07D 413/12* (2013.01)

(58) Field of Classification Search

CPC ...... C07D 271/08; C07D 413/12; A61P 35/00
See application file for complete search history.

(56) References Cited

PUBLICATIONS

Jia et al., Synthesis of the Antitumor β-elemene Derivatives, Youji Huaxue, (1991), 11, 608-610—Google Machine Translation—Obtained Sep. 10, 2025 (Year: 1991).*

CN 106866572 A—Description—Patentscope Machine Translation—Obtained Sep. 10, 2025 (Year: 2017).*

Patani et al., Bioisosterism: A Rational Approach in Drug Design, Chemical Reviews, (1996). 96(8), 3147-3176 (Year: 1996).*

* cited by examiner

*Primary Examiner* — Renee Claytor
*Assistant Examiner* — Christopher Lindsay Johnson
(74) *Attorney, Agent, or Firm* — Hoffman Warnick LLC

(57) ABSTRACT

Disclosed are a 14-chloro-β-elemene nitric oxide donor derivative and a preparation method and use thereof in the preparation of anti-tumor drugs. The 14-chloro-β-elemene nitric oxide donor derivative has a general formula shown in formula (I): in formula (I): $R^1$ represents a linear or cyclic alcohol amine structure containing nitrogen and oxygen atoms; and each of $R^2$ and $R^3$ is independently selected from the group consisting of $C_{1-10}$ alkyl, $C_{3-12}$ cycloalkyl, $C_{6-12}$ aryl, 5- to 10-membered cyclic heteroaryl, $C_{2-10}$ alkenyl, $C_{2-10}$ alkynyl, and $C_{2-10}$ alkoxy.

formula (I)

(I)

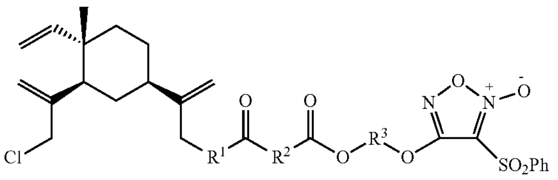

10 Claims, 7 Drawing Sheets

13-β-elemene

2

3

4

5

10

6

4

9

7

8

11

12

13

14a

14b

15a

15b 5-10

14, 15

$R^1$= $-CH_2CH_2-$, $-CH_2CH_2CH_2-$ $R^2$= $-CH_2CH_2-$, $-CH_2C{\equiv}CCH_2-$

| | Bioluminescence signal intensity of brain tumor ($\times 10^5$, $\frac{p/sec/cm^2/sr}{\mu W/cm^2}$) | | | |
|---|---|---|---|---|
| | **Week 0** | **Week 1** | **Week 2** | **Week 3** |
| **Model** | 4.8±0.4 | 82.5±8.1 | 649.0±95.3 | 4874.6±2125.5 |
| **β-Elemene** | 4.3±0.8 | 63.2±11.9 | 120.6±39.7 | 665.7±210.7 |
| **Id** | 4.0±0.3 | 11.2±6.3 | 65.2±19.3 | 115.3±39.8 |

14-CHLORO-β-ELEMENE NITRIC OXIDE DONOR DERIVATIVE AND PREPARATION METHOD AND USE THEREOF

CROSS REFERENCE TO RELATED APPLICATION

This patent application is a national stage application of International Patent Application No. PCT/CN2022/116672, filed on Sep. 2, 2022, which claims the priority of Chinese Patent Application No. 2021111804247, entitled "14-chloro-beta- elemene nitric oxide donor derivative and preparation method and use thereof" filed with the China National Intellectual Property Administration on Oct. 11, 2021, the disclosure of which is incorporated herein by reference in its entirety.

TECHNICAL FIELD

The present disclosure relates to the field of medicinal chemistry, and specifically relates to a 14-chloro-β-elemene NO donor derivative and a preparation method and use thereof.

BACKGROUND

Elemene is a sesquiterpene natural product exacted and isolated from *Curcuma zedoaria* and has broad anti-tumor activity. In 1994, elemene oral emulsion and injection were approved by the China Food and Drug Administration (CFDA) as broad-spectrum anti-tumor drugs for the treatment of lung, liver, esophageal, nasopharyngeal, and brain cancers.

In the elemene extract mixture, β-elemene has the highest content and is also the most important anti-tumor active ingredient. However, the structure of β-elemene only contains two elements of carbon and hydrogen, leading to β-elemene having great-fat solubility, poor water solubility, and low bioavailability. β-elemene is not easily absorbed by the human body, thus limiting its clinical application. Taking β-elemene injection as an example, patients often need to be administered high-dose injections during treatment. The medical solution highly irritate to the patient's blood vessels, which may easily cause phlebitis. Therefore, it is necessary to carry out structural transformation and modification of β-elemene to improve its physicochemical properties on the one hand and enhance its anti-tumor activity on the other hand.

Nitric oxide (NO) is involved in various physiological and pathological processes. High levels of nitric oxide can inhibit the growth of tumor cells through various signaling pathways, such as ERKs and Akt. However, as a small gas molecule, NO is difficult to quantify and transport, so the preparation of a portable and stable nitric oxide donor has become a research hotspot.

Studies have found that phenylsulfonylfurazan, a classic nitric oxide donor, can produce high levels of nitric oxide in vitro and in vivo. Therefore, the introduction of nitric oxide donors into the structure of β-elemene will significantly enhance the anti-tumor activity of β-elemene, improve the drug-likeness of β-elemene, and hopefully obtain anti-tumor drugs with better efficacy.

Chinese Patent Application No. 201710066664.1 discloses a synthesis of a nitric oxide donator β-elemene derivative. The specific synthetic route and general structure are shown in FIG. 1. The compound reported in this patent is prepared by using 13-alcohol of β-elemene as an intermediate and connecting it with a furoxan-type nitric oxide donor through an esterification reaction to prepare an ester-type nitric oxide β-elemene derivative. Although this series of compounds exhibited good in vitro anti-tumor activity and in vivo tumor suppressive activity, such as shown in FIG. 1, the ester bond at the 13-position of β-elemene in this series of compounds is easy to be hydrolyzed by esterases in vivo to metabolize to 13-β-elemenol. Subsequently, 13-β-elemenol would be rapidly metabolized through oxidation to 13-β-elemenal. However, 13-β-elemenal has strong cytotoxicity. The administration of medium and high doses for a long time can directly cause the death of administered animals. Therefore, long-term administration has a greater risk to safety and is not suitable for the human body. In addition, because the compounds disclosed in this patent are easy to metabolize and decompose, the stability of the compound is poor, and it is difficult to penetrate the blood-brain barrier, so it cannot effectively treat intracerebral tumors, such as malignant brain glioma.

SUMMARY

In the present disclosure, an alcohol amine structure in the 14-chloro-β-elemene nitric oxide donor derivative functions as a linker. A 13-β-elemene amine intermediate is firstly prepared and then connected with a furazan nitric oxide donor to finally prepare a β-elemene nitric oxide donor derivative with a novel linker, which has excellent activities, and is absent of the toxicity problem that may occur in CN201710066664.1.

In the present disclosure, the synthetic route of 13,14-dichloro-β-elemene is shown in FIG. 2. The reaction conditions and reagents used are as follows: N-chlorosuccinimide (NCS), ytterbium trifluoromethanesulfonate (Yb $(OTf)_3$), and trimethylchlorosilane (TMSCl), dichloromethane ($CH_2Cl_2$):tetrahydrofuran (THF) (4:1, v/v), at 0° C.

In the present disclosure, 13,14-dichloro-β-elemene is chosen as a skeleton to provide anti-tumour activity, which has the following important advantages: 1) In the chlorination reaction of β-elemene, 13-chloro-β-elemene (intermediate 2, main product), 14-chloro-β-elemene (intermediate 3, by-product), and 13,14-dichloro-β-elemene (intermediate 4) are simultaneously generated. However, the polarities of the two monosubstituted β-elemene chloro derivatives are extremely similar, and it is difficult to separate one from the other even if preparative high performance liquid chromatography (HPLC) is used. Their mixture can only be used as the raw material for subsequent reactions, resulting in forming a certain amount of 14-position derivatives in the final products, increasing the complexity in purification. Therefore, the prepared compounds are difficult to purify and are not suitable for industrial mass production, which is not conducive to the development of drugs that can be prepared on a large scale. Therefore, the development and research of drugs are difficult to conduct. 2) The preparation of 13,14-dichloro-β-elemene is relatively easy to realize, and the polarity of the dichloro product is quite different from that of monochloro-β-elemenes, so it is easy to separate and obtain a high-purity dichloro-β-elemene intermediate and the subsequent derivative final product, and it is suitable for scale-up production. 3) The anti-tumor activity of 13,14-dichloro-β-elemene is equivalent to that of 13-chloro-β-elemene, 14-chloro-β-elemene, and β-elemene, and due to slightly increased polarity after dichlorination, 13,14-dichloro-β-elemene exhibits a better drug-like property.

Therefore, the β-elemene nitric oxide donor derivative disclosed in the present disclosure is easy to prepare and separate, and has better structural and metabolic stability, and better long-term medication safety. Also, it can penetrate the blood-brain barrier and effectively inhibit malignant brain glioma, and has good innovation and novelty.

Provided is a 14-chloro-β-elemene nitric oxide donor derivative, and a pharmaceutically acceptable salt, a solvate, an enantiomer, or a diastereoisomer thereof.

In the present disclosure, the 14-chloro-β-elemene nitric oxide donor derivative has a structural general formula as shown in formula (I):

(I)

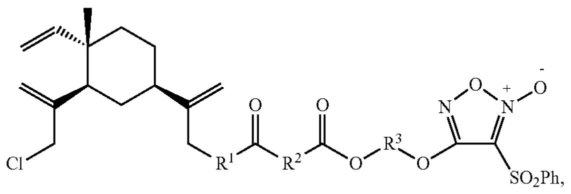

in formula (I):

$R^1$ represents a linear or cyclic alcohol amine structure containing nitrogen and oxygen atoms; and each of $R^2$ and $R^3$ is independently selected from the group consisting of $C_{1-10}$ alkyl, $C_{3-12}$ cycloalkyl, $C_{6-12}$ aryl, 5- to 10-membered cyclic heteroaryl, $C_{2-10}$ alkenyl, $C_{2-10}$ alkynyl, and $C_{2-10}$ alkoxy.

In some embodiments, in formula (I):

$R^1$ represents a linear $C_{2-5}$ alcohol amine structure containing nitrogen and oxygen atoms or a cyclic $C_{5-6}$ alcohol amine structure containing nitrogen and oxygen atoms; and each of $R^2$ and $R^3$ is independently selected from the group consisting of $C_{2-6}$ alkyl, $C_{2-6}$ alkenyl, and $C_{2-6}$ alkynyl.

In some embodiments, in formula (I):

$R^1$ is any one selected from the group consisting of

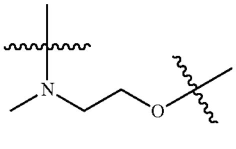

,

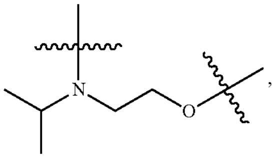

,

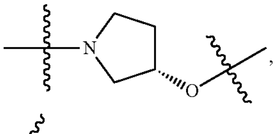

,

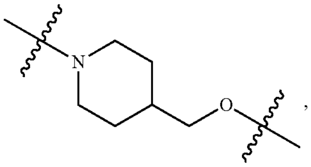

,

-continued

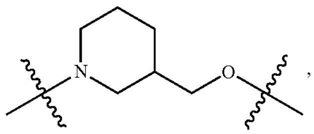

,

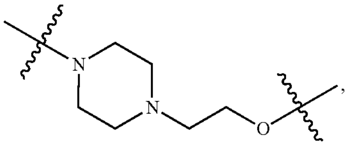

,

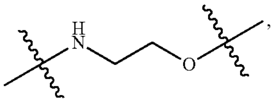

,

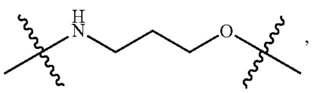

,

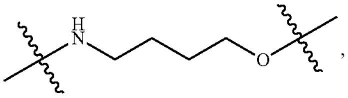

,

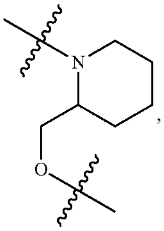

, and

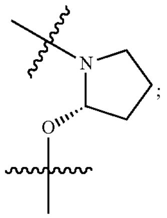

;

and each of $R^2$ and $R^3$ is independently any one selected from the group consisting of $-CH_2CH_2-$, $-CH_2CH_2CH_2-$, $-CH_2CH_2CH_2CH_2-$, $-CH_2CH_2CH_2CH_2CH_2-$, $-CH{=}CH-$, $-CH_2CH{=}CH-$, $-CH{=}CHCH_2-$, $-CH_2CH{=}CHCH_2-$, $-CH_2CH_2CH{=}CH-$, $-CH{=}CHCH_2CH_2-$, $-CH_2C{\equiv}C-$, $-C{\equiv}CCH_2-$, $-CH_2C{\equiv}CCH_2-$, $-CH_2CH_2C{\equiv}CCH_2-$, $-CH_2CH_2C{\equiv}CCH_2CH_2-$, and $-CH_2C{\equiv}CCH_2CH_2-$.

In some embodiments, the 14-chloro-β-elemene nitric oxide donor derivative is any one selected from the group consisting of compounds having a structure as shown in formulas I-1 to I-6:

I-1

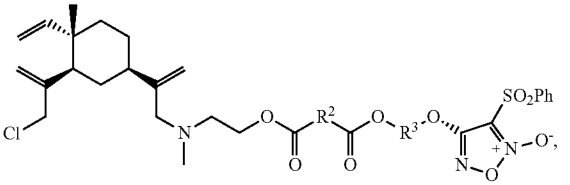

I-2

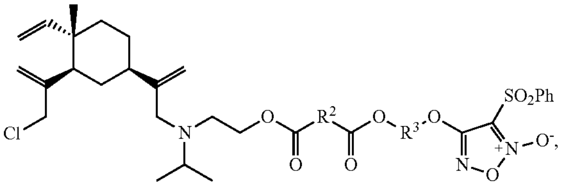

I-3

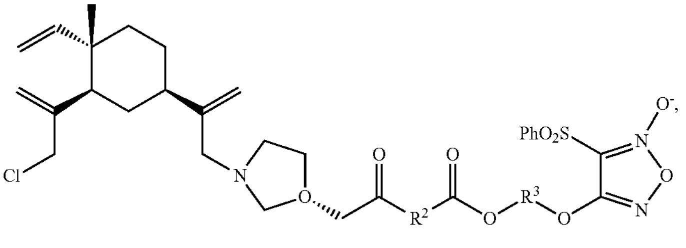

I-4

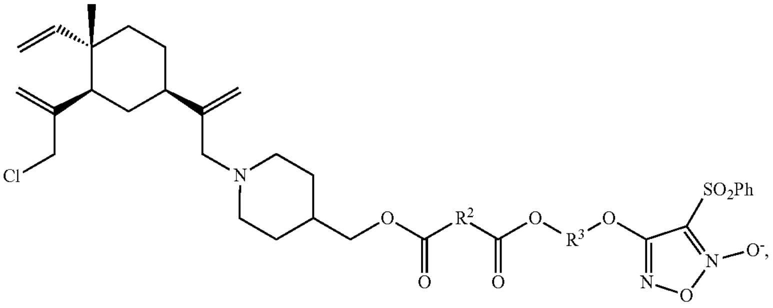

I-5

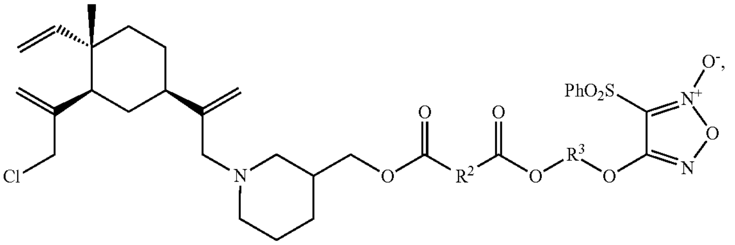

and

I-6

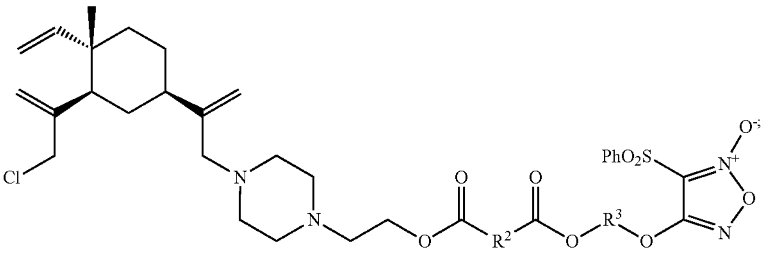

and in the formulas I-1 to I-6, each of $R^2$ and $R^3$ is independently any one selected from the group consisting of $C_{2-6}$ alkyl, $C_{2-6}$ alkenyl, and $C_{2-6}$ alkynyl, including any one selected from the group consisting of $-CH_2CH_2-$, $-CH_2CH_2CH_2-$, $-CH_2CH_2CH_2CH_2-$, $-CH_2CH_2CH_2CH_2CH_2-$, $-CH{=}CH-$, $-CH_2CH{=}CH-$, $-CH{=}CHCH_2-$, $-CH_2CH{=}CHCH_2-$, $-CH_2CH_2CH{=}CH-$, $-CH{=}CHCH_2CH_2-$, $-CH_2C{\equiv}C-$, $-C{\equiv}CCH_2-$, $-CH_2C{\equiv}CCH_2-$, $-CH_2CH_2C{\equiv}CCH_2-$, $-CH_2CH_2C{\equiv}CCH_2CH_2-$, and $-CH_2C{\equiv}CCH_2CH_2-$.

In some embodiments, the 14-chloro-β-elemene nitric oxide donor derivative is any one selected from the group consisting of the compounds having a structure shown in formulas 1 to 24 as follows:

1
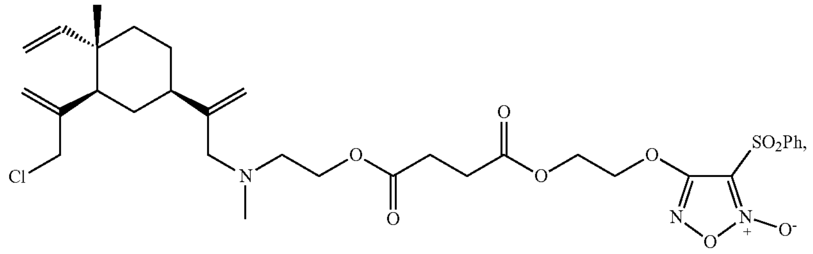
2
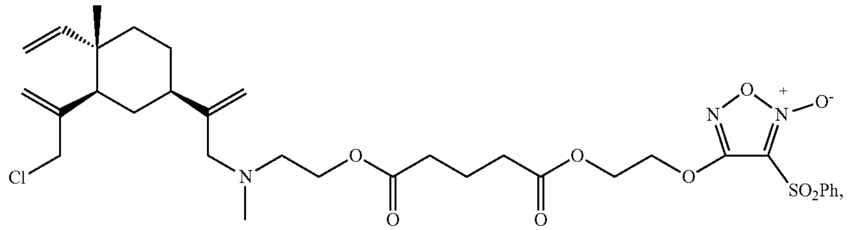
3
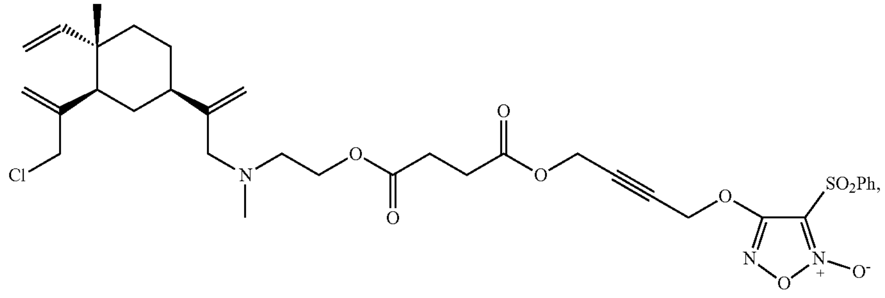
4
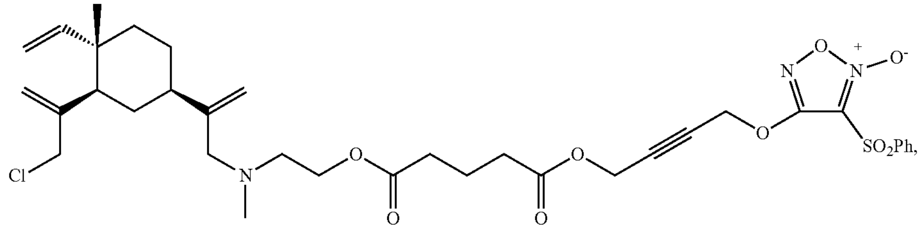
5
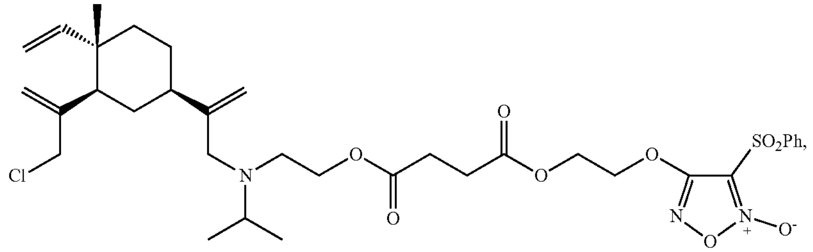
6
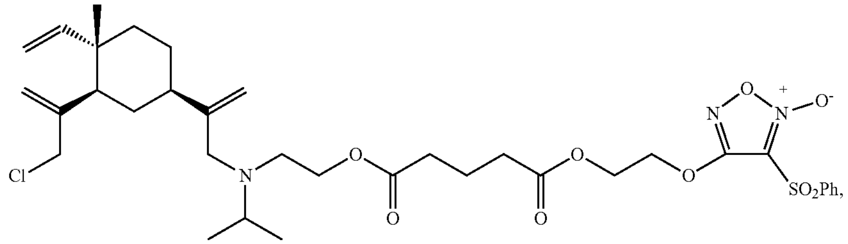

-continued
7
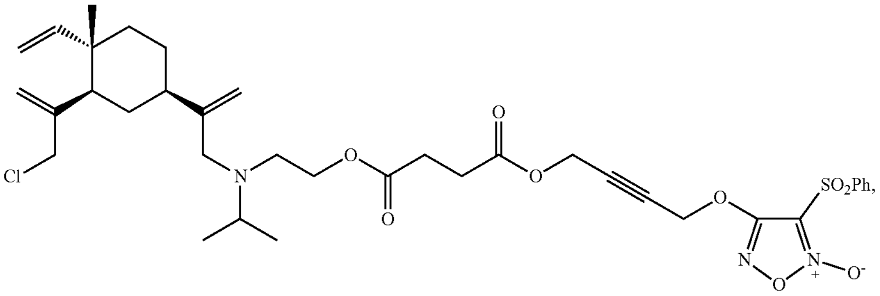
8
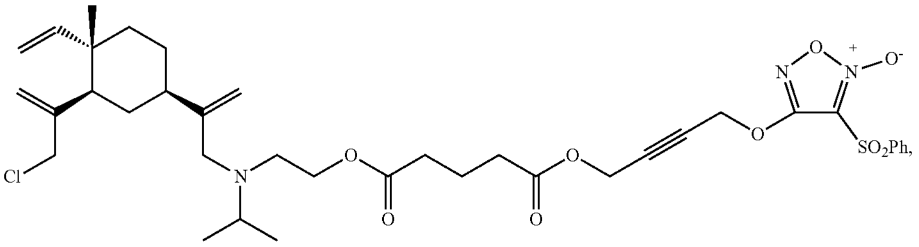
9
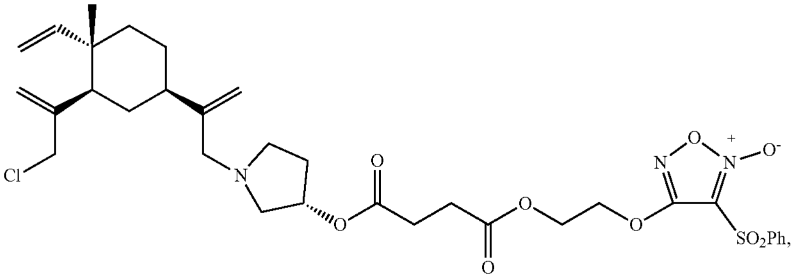
10
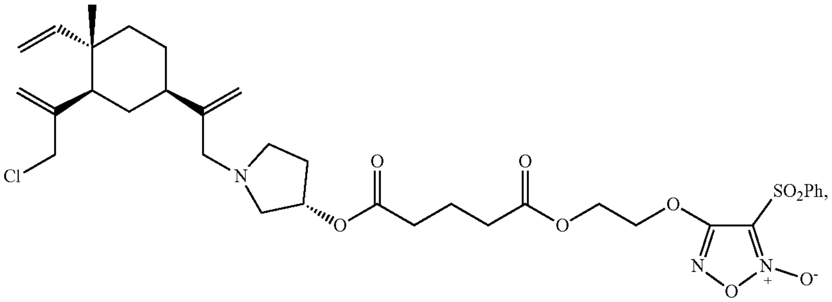
11
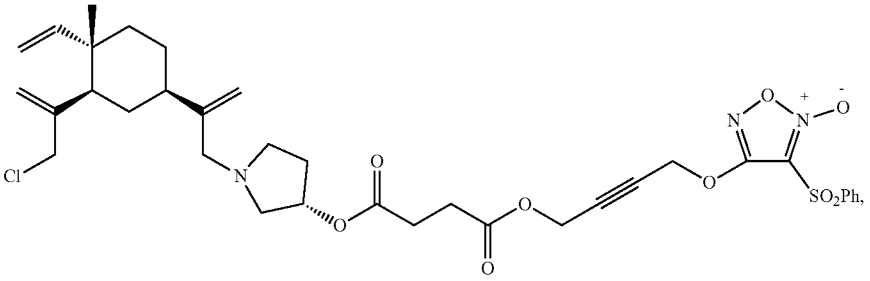

-continued
12
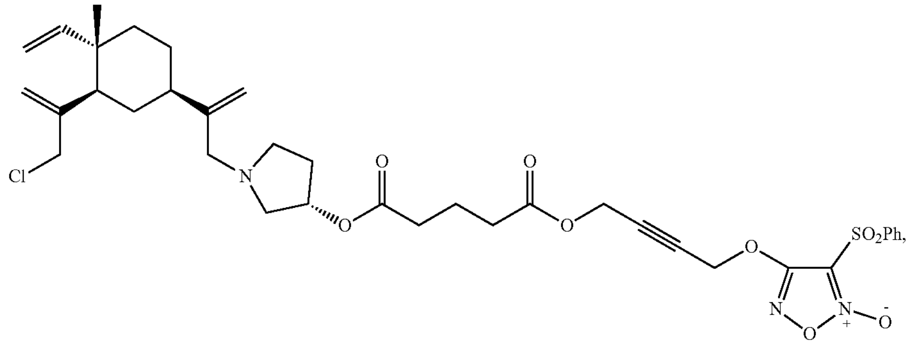
13
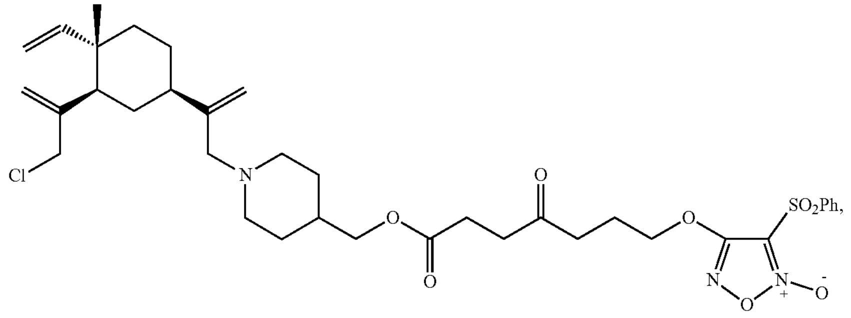
14
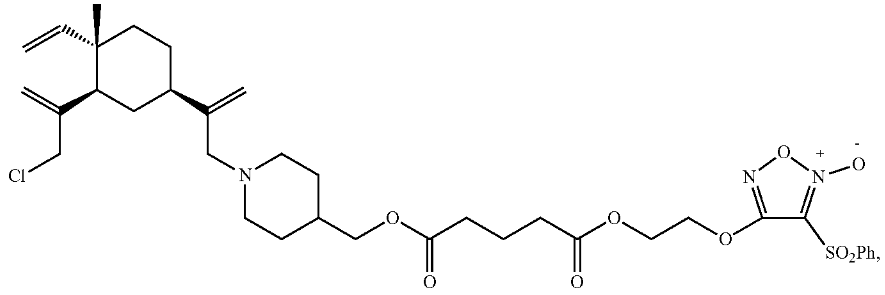
15
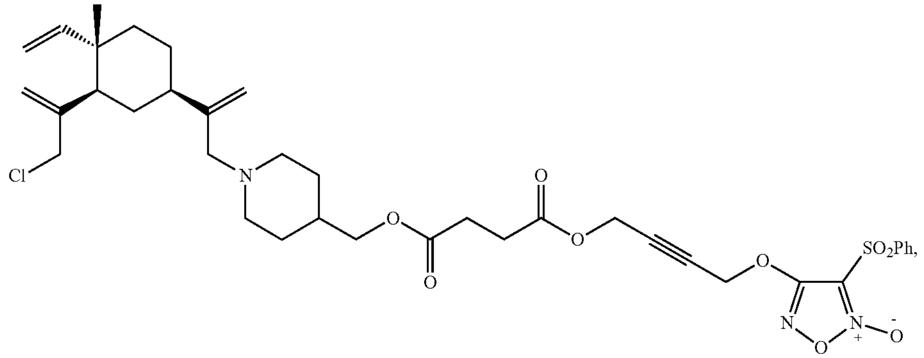
16
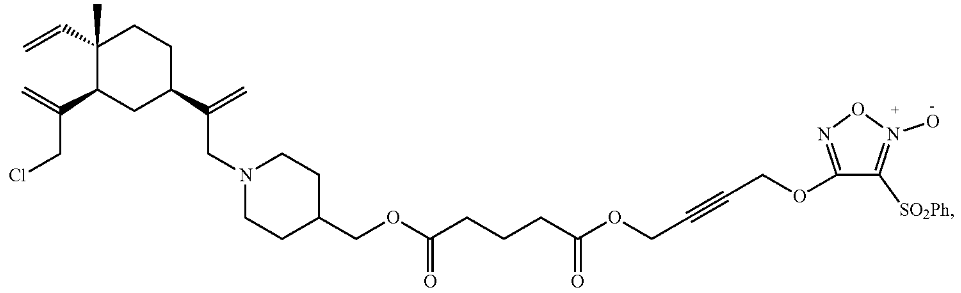

-continued
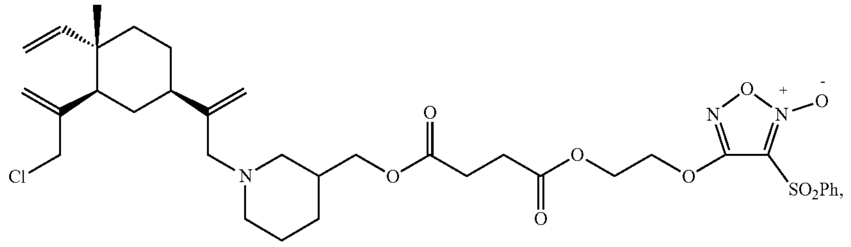
17
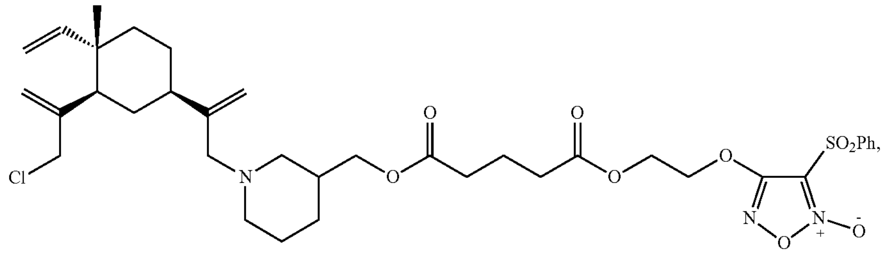
18
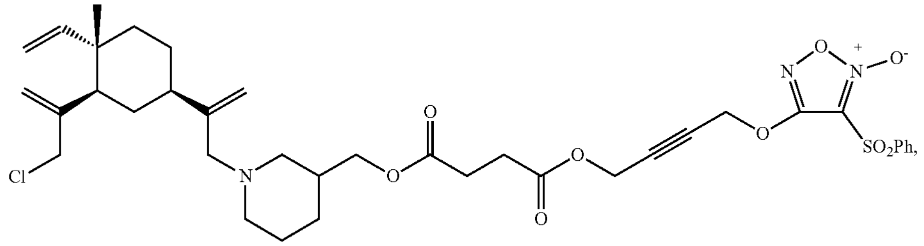
19
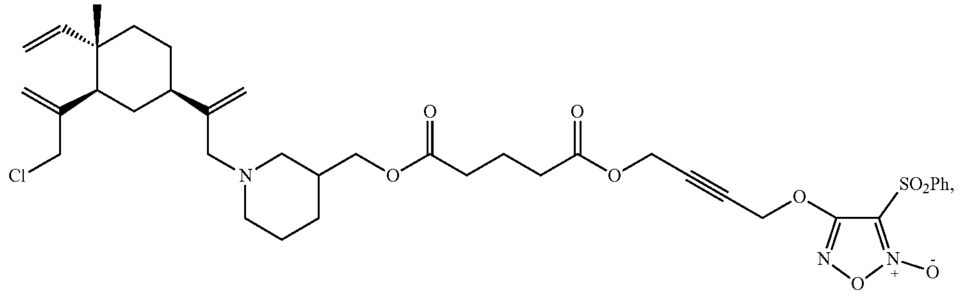
20
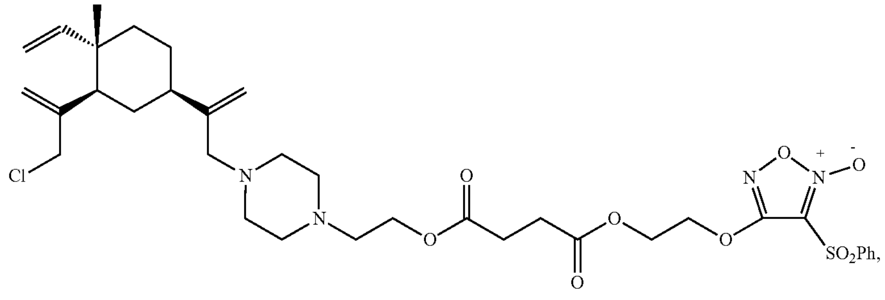
21

-continued

22

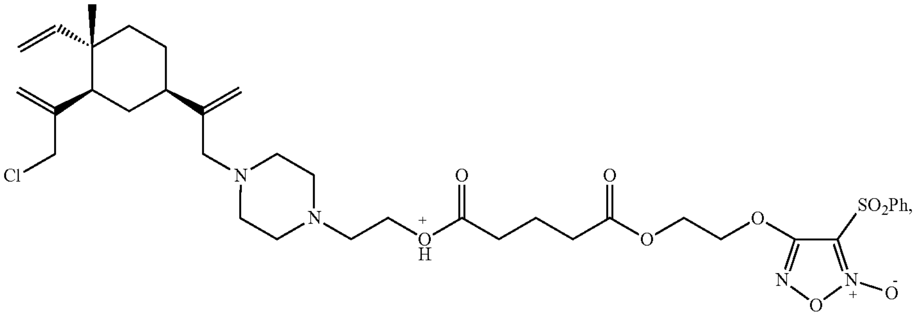

23

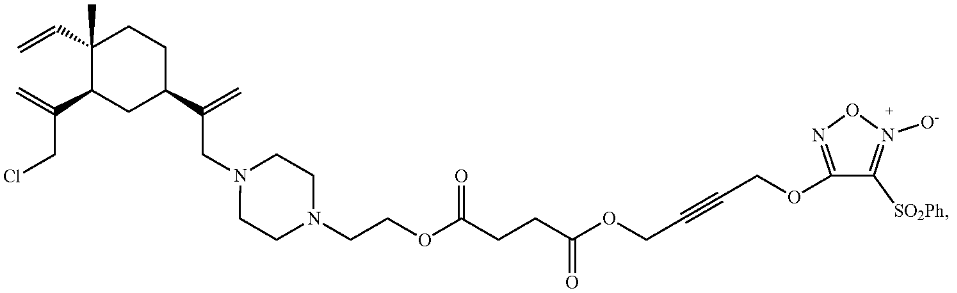

and

24

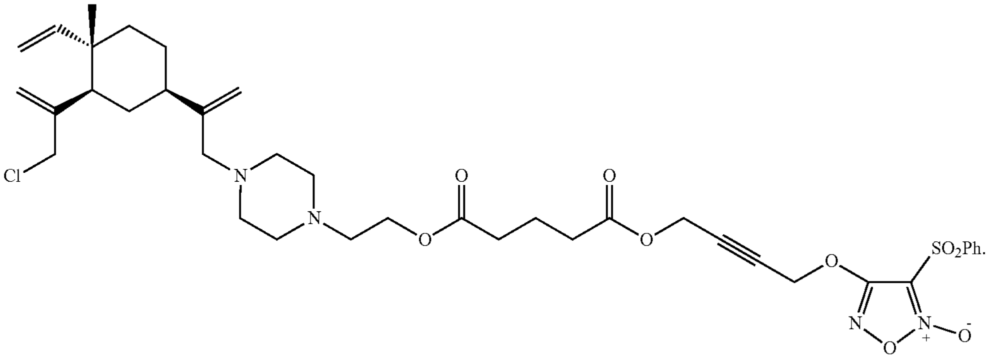

Further provided is use of the 14-chloro-β-elemene nitric oxide donor derivative, and a pharmaceutically acceptable salt, a solvate, an enantiomer, or a diastereoisomer thereof as described in the above technical solutions in the preparation of anti-tumor drugs.

In some embodiments, the tumor comprises lung cancer, colon cancer, or malignant brain glioma.

Compared with the prior art, the embodiments provided by the present disclosure the has the following main advantages:

In the present disclosure, an alcohol amine structure that can enhance in vivo anti-tumor activity is introduced as a linker, which improves in vivo stability and provides good therapeutic activity against malignant brain glioma against which effective therapeutic drugs is short in clinical practice.

DETAILED DESCRIPTION OF THE EMBODIMENTS

The present disclosure will be further described below with reference to the drawings and specific examples. It should be understood that these embodiments are intended to illustrate the present disclosure only but not limit the scope of the present disclosure. The operation methods without specific conditions in the following embodiments are generally in accordance with conventional conditions or the conditions recommended by the manufacturer.

(1) Preparation of Intermediate 4

Figure 1:
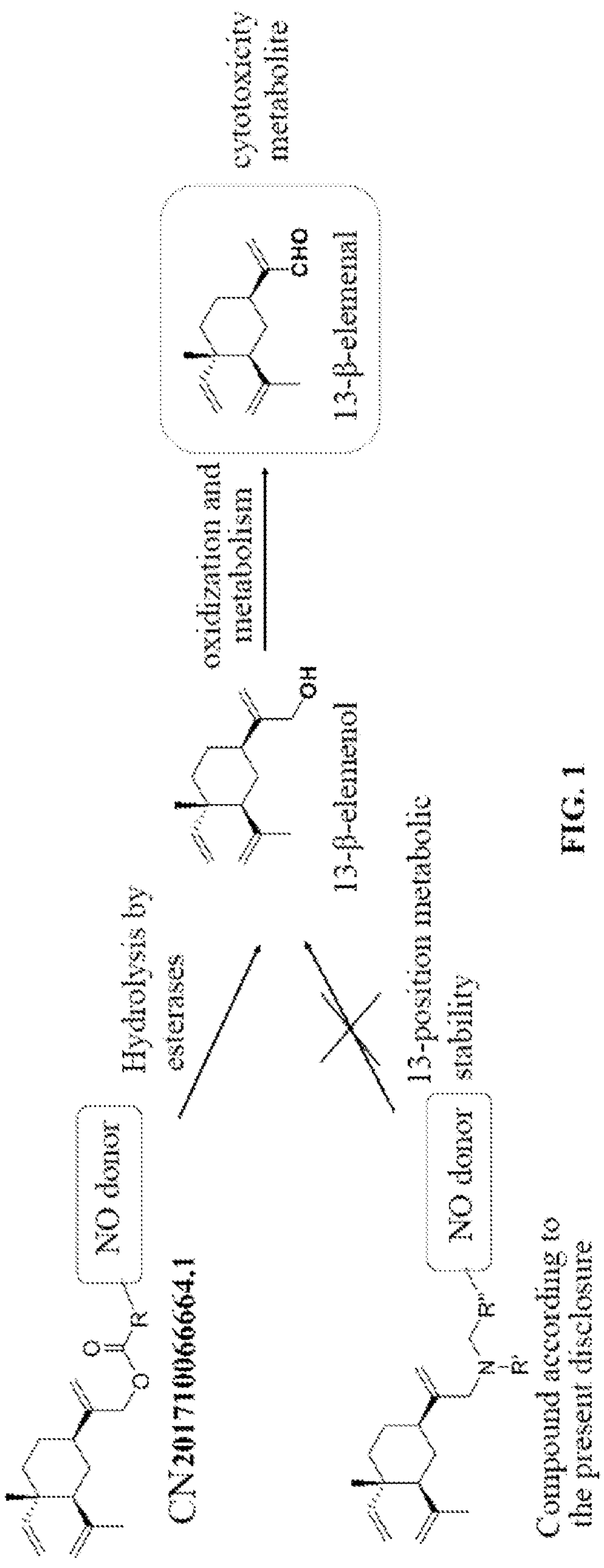
FIG. 1 shows the advantages of the compound prepared in an embodiment of the present disclosure compared with that prepared in CN201710066664.1.
Figure 2:
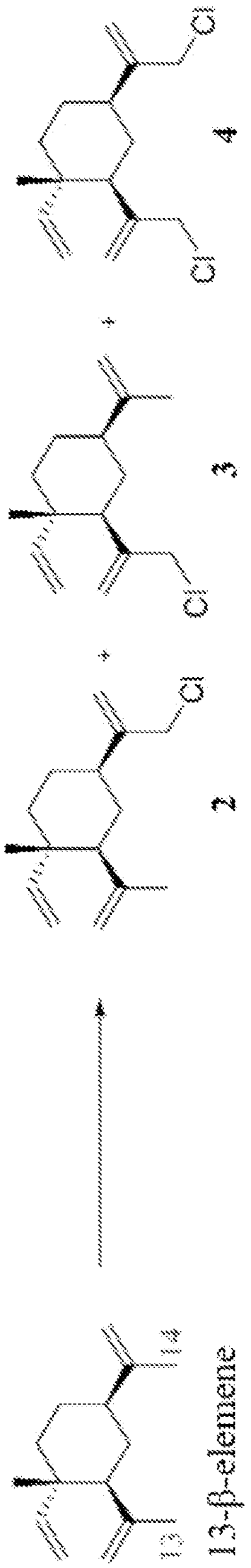
FIG. 2 shows the synthetic route of 13,14-dichloro-β-elemene.

As shown in the synthetic route in FIG. 2, NCS (1.34 g, 20 mmol), ytterbium trifluoromethanesulfonate (310 mg, 0.5 mmol), trimethylchlorosilane (54 mg, 0.5 mmol) were added in turn to a mixed solution of dichloromethane (8 mL) and tetrahydrofuran (2 mL) containing β-elemene (1.02 g, 5 mmol) at 0° C., obtaining a reactant mixture. The reactant mixture reacted at 0° C. for 8 h. At the end of the reaction, the resulting reaction product mixture was distilled under reduced pressure to remove solvents, and then diluted by adding water (15 mL). The resulting mixture was subjected to extraction with ethyl acetate (4 mL) three times, and organic phases were combined. The organic phase after combining was washed with water (20 mL×2) and saturated saline (20 mL×2) in turn, and dried with anhydrous sodium sulfate, obtaining a dried organic phase. The dried organic phase was distilled under reduced pressure to remove solvent, obtaining a residue. The residue was purified by silica gel column chromatography (pure petroleum ether), obtaining a colorless liquid compound, i.e., intermediate 4 with a yield of 45%. The spectroscopy data is as follows.

$^{1}$H NMR of Intermediate 4

$^{1}$H NMR (400 MHz, $CDCl_3$) δ 5.85-5.72 (m, 1H), 5.28 (s, 1H), 5.18 (s, 1H), 5.04 (s, 1H), 4.98-4.89 (m, 3H), 4.15-4.05 (m, 3H), 3.97 (d, J=11.7 Hz, 1H), 2.35-2.21 (m, 2H), 1.77-1.42 (m, 6H), 0.99 (s, 3H). $^{13}$C NMR (100 MHz, $CDCl_3$) δ 149.6, 149.0, 147.5, 116.4, 113.5, 111.6, 51.1, 47.8, 47.5, 41.0, 39.8, 39.7, 33.8, 27.0, 15.8.

(2) Preparation of Intermediates 5 to 10

Figure 3:
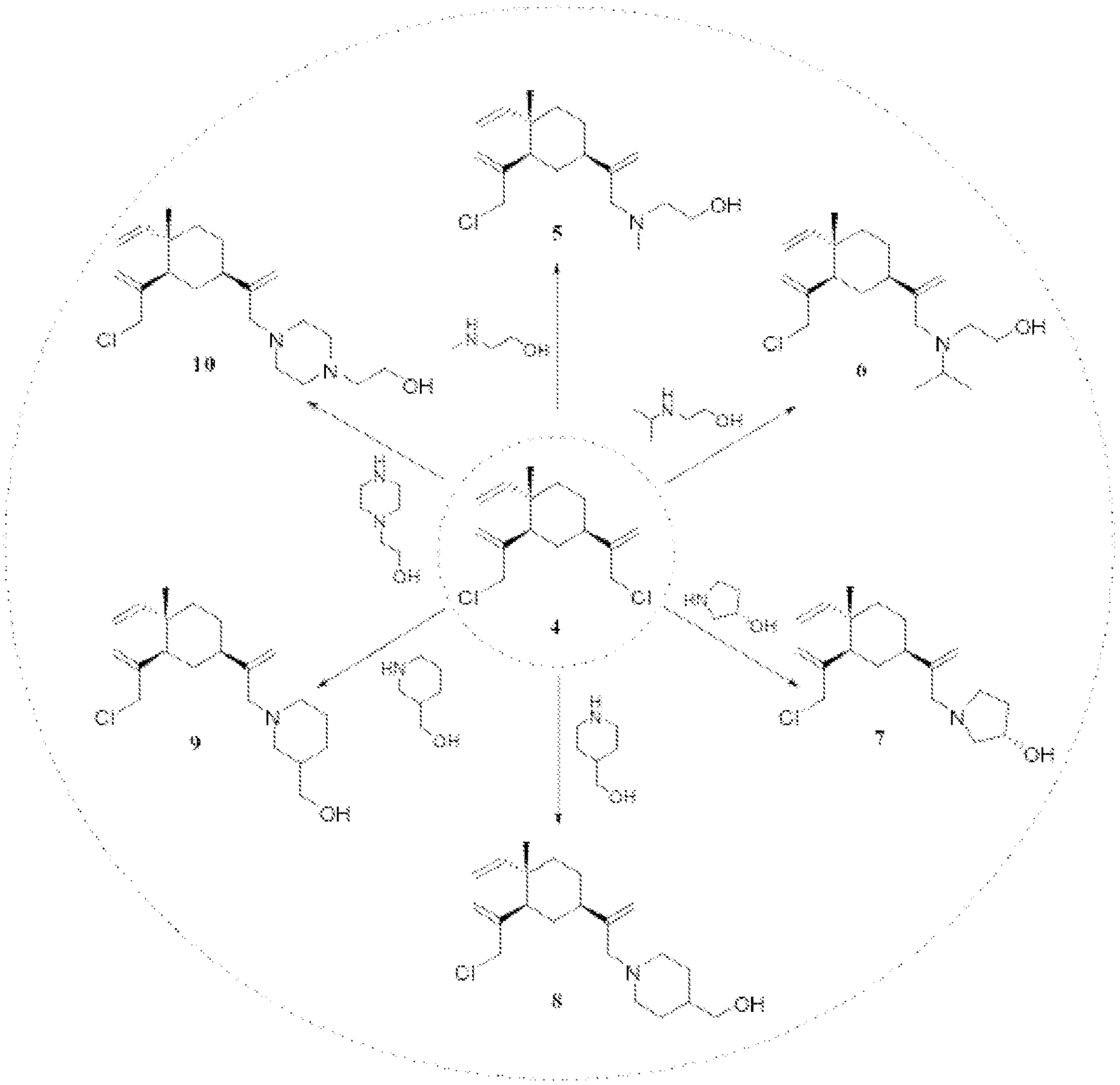
FIG. 3 shows the synthetic routes of intermediates 5 to 10.

As shown in the synthetic route in FIG. 3, a corresponding alcohol amine reactant (1.3 mmol) and N,N-diisopropylethylamine (DIPEA, 172 mg, 1.3 mmol) were added in turn to N,N-dimethylformamide (DMF, 3 mL) containing the intermediate 4 (304 mg, 1.1 mmol) and they were stirred at 60° C. for 12. At the end of a reaction, the reaction product mixture was diluted with water (10 mL), and the resulting mixture was subjected to extraction with ethyl acetate (10 mL), obtaining an organic phase. The organic phase was combined, washed with water (10 mL) and saturated salt water (10 mL), and dried with anhydrous sodium sulfate, obtaining a residue. The residue was purified by silica gel column chromatography (dichloromethane:methanol of 150:1 v/v), obtaining a pale yellow liquid, i.e., intermediates 5 to 10. The spectroscopy data is as follows.

$^{1}$H NMR of Intermediates 5 to 10

2-((2-((1R,3R,4S)-3-(3-chloroprop-1-en-2-yl)-4-methyl-4-vinyl cyclohexyl))(methyl)amino)ethan-1-ol (5)

Light yellow liquid, yield 44%. $^{1}$H NMR (400 MHz, $CDCl_3$) δ 5.78 (dd, J=18.0, 10.3 Hz, 1H), 5.27 (s, 1H), 5.01-4.88 (m, 5H), 4.14-3.91 (m, 2H), 3.61 (t, J=5.4 Hz, 2H), 3.01 (s, 2H), 2.56-2.51 (m, 2H), 2.28 (dd, J=12.5, 3.4 Hz, 1H), 2.20 (s, 3H), 2.11 (t, J=11.8 Hz, 1H), 1.72-1.44 (m, 6H), 0.98 (s, 3H). $^{13}$C NMR (100 MHz, $CDCl_3$) δ 151.0, 149.3, 147.8, 116.2, 111.4, 111.3, 63.1, 59.0, 58.6, 51.0, 41.9, 41.7, 40.0, 39.9, 34.1, 27.3, 16.0. HRMS (ESI) calcd for $C_{18}H_{31}ClNO$ 312.2089 $[M+H]^+$, found 312.2080.

2-((2-((1R,3R,4S)-3-(3-chloroprop-1-en-2-yl)-4-methyl-4-vinyl cyclohexyl)allyl)(isopropyl)amino)ethan-1-ol (6)

Light yellow liquid, yield 60%. $^{1}$H NMR (400 MHz, $CDCl_3$) δ5.77(dd, J=17.1, 11.2 Hz, 1H), 5.26 (s, 1H), 5.02-4.79 (m, 5H), 4.02 (dd, J=47.3, 11.7 Hz, 2H), 3.51 (s, 2H), 3.02 (d, J=18.7 Hz, 3H), 2.54 (s, 2H), 2.27 (dd, J=12.6, 3.1 Hz, 1H), 2.14 -2.02 (m, 1H), 1.71-1.41 (m, 6 H), 0.98 (d, J=7.2 Hz, 9H). $^{13}$C NMR (100 MHz, $CDCl_3$) δ149.2, 147.7, 116.3, 111.4, 58.5, 54.9, 51.2, 49.9, 49.1, 47.9, 41.7, 39.9, 40.0, 34.3, 27.3, 17.8, 17.7, 15.9. HRMS (ESI) calcd for $C_{20}H_{35}ClNO$ 340.2402 $[M+H]^+$, found 340.2394.

(S)-1-(2-((1R,3R,4S)-3-(3-chloroprop-1-en-2-yl)-4-methyl-4-vinyl cyclohexyl)allyl)pyrrolidin-3-ol (7)

Light yellow liquid, yield 48%. $^{1}$H NMR (400 MHz, $CDCl_3$) δ5.77 (dd, J=17.1, 11.1 Hz, 1H), 5.26 (s, 1H), 5.05-4.80 (m, 5H), 4.30 (s, 1H), 4.09 (d, J=11.6 Hz, 1H), 3.96 (d, J=11.7 Hz, 1H), 3.05 (q, J=13.4 Hz, 2H), 2.85 (td, J=8.1, 7.2, 4.1 Hz, 1H), 2.66 (d, J=10.2 Hz, 1H), 2.55 (s, 1H), 2.43 (dd, J=10.2, 5.1 Hz, 1H), 2.31-2.07 (m, 4H), 1.69-1.41 (m, 6H), 0.96 (s, 3H). $^{13}$C NMR (100 MHz, $CDCl_3$) δ 151.4, 149.3, 147.7, 116.3, 111.3, 110.2, 71.5, 63.1, 60.9, 52.6, 51.1, 47.7, 42.0, 39.9, 39.8, 35.0, 34.0, 27.1, 15.8. HRMS (ESI) calcd for $C_{19}H_{31}ClNO$ 324.2089 $[M+H]^+$, found 324.2083.

(1-(2-((1R,3R,4S)-3-(3-chloroprop-1-en-2-yl)-4-methyl-4-vinyl cyclohexyl)allyl)piperidin-4-yl) methanol (8)

Light yellow liquid, yield 60%. $^{1}$H NMR (400 MHz, $CDCl_3$) δ5.79 (dd, J=17.9, 10.4 Hz, 1H), 5.26 (s, 1H), 4.98-4.86 (m, 5H), 4.09 (d, J=11.7 Hz, 1H), 3.97 (d, J =11.7 Hz, 1H), 3.50 (d, J=6.4 Hz, 2H), 2.90 (d, J=14.5 Hz, 4H), 2.32-2.23 (m, 1H), 2.13 (d, J=7.9 Hz, 1H), 1.88 (s, 2H), 1.75-1.57 (m, 7H), 1.53-1.43 (m, 4H), 0.98 (s, 3H). $^{13}$C NMR (100 MHz, $CDCl_3$) δ149.1, 147.6, 115.9, 110.9, 67.8, 63.5, 53.5, 53.3, 50.8, 47.6, 42.0, 39.7, 39.6, 38.5, 33.8, 28.6, 26.8, 15.6. HRMS (ESI) calcd for $C_{21}H_{35}ClNO$ 352.2402 $[M+H]^+$, found 352.2384.

(1-(2-((1R,3R,4S)-3-(3-chloroprop-1-en-2-yl)-4-methyl-4-vinyl cyclohexyl)allyl)piperidin-3-yl) methanol (9)

Light yellow liquid, yield 51%. $^{1}$H NMR (400 MHz, $CDCl_3$) δ 5.83-5.73 (m, 1H), 5.26 (s, 1H), 4.91 (dd, J=10.5, 6.4 Hz, 5H), 4.14-4.02 (m, 1H), 3.97 (d, J=11.7 Hz, 1H), 3.69-3.54 (m, 2H), 2.89 (d, J=3.9 Hz, 2H), 2.68 (d, J=9.7 Hz, 1H), 2.47 (s, 2H), 2.27 (dd, J=11.0, 5.0 Hz, 1H), 2.09 (ddt, J=12.2, 8.2, 4.3 Hz, 2H), 1.82-1.74 (m, 2H), 1.70-1.41 (m, 9H), 0.97 (s, 3H). $^{13}$C NMR (100 MHz, $CDCl_3$) δ150.7, 149.4, 147.8, 147.8, 116.2, 111.3, 111.0, 67.5, 64.1, 57.8, 54.4, 51.0, 47.8, 42.1, 39.9, 39.9, 34.0, 27.8, 27.0, 24.6, 15.8. HRMS (ESI) calcd for $C_{21}H_{35}ClNO$ 352.2402 $[M+H]^+$, found 352.2412.

2-((4-(2-(4-(2-((1R,3R,4S)-3-(3-chloroprop-1-en-2-yl)-4-methyl-4-vinyl cyclohexyl)allyl)piperazin-1-yl)ethan-1-ol (10)

Light yellow liquid, yield 44%. $^{1}$H NMR (400 MHz, $CDCl_3$) δ5.78 (dd, J=18.0, 10.2 Hz, 1H), 5.26 (s, 1H), 4.97-4.85 (m, 5H), 4.09 (d, J=11.5 Hz, 1H), 3.96 (d, J=11.6

Hz, 1H), 3.61 (t, J=5.4 Hz, 2H), 2.91 (d, J=4.2 Hz, 2H), 2.62-2.38 (m, 10H), 2.30-2.25 (m, 1H), 2.15-2.08 (m, 1H), 1.64-1.43 (m, 6H), 0.97 (s, 3H). $^{13}C$ NMR (100 MHz, $CDCl_3$) δ150.7, 149.4, 147.8, 116.3, 111.3, 111.0, 63.5, 59.4, 57.8, 53.3, 53.1, 51.2, 47.7, 42.2, 39.9, 39.9, 34.0, 27.1, 15.8. HRMS (ESI) calcd for $C_{21}H_{36}ClN_2O$ 367.2511 $[M+H]^+$, found 367.2503.

(3) Preparation of Intermediates 12 and 13

At 0° C., 25% NaOH aqueous solution (0.2 mL) was added slowly dropwise to a tetrahydrofuran solution containing 3,4-bis(phenylsulfonyl)-1,2,5-oxadiazole 2-oxide (183 mg, 0.5 mmol). After the dropwise addition, the resulting mixture was stirred for further 10 min, and a reactant ethylene glycol (124 mg, 2 mmol) was added thereto. The resulting reactant mixture reacted for 6 h at room temperature. The reaction product mixture was distilled under reduced pressure to remove solvent, and then diluted by adding water (15 mL). The resulting mixture was subjected to extraction with dichloromethane (20 mL) for three times, and organic phases were combined. The organic phase after combining was washed with water (20 mL×2) and saturated saline (20 mL×2) in turn, and dried with anhydrous sodium sulfate, obtaining a dried organic phase. The dried organic phase was distillated under reduced pressure to remove solvent, obtaining a residue. The residue was purified by silica gel column chromatography (dichloromethane:methanol of 400:1, v/v), obtaining an intermediate 12 (72 mg, 48%).

m.p. 128-130° C. $^1H$ NMR (400 MHz, $CDCl_3$) δ 8.07 (d, J=8.2 Hz, 2H), 7.77 (t, J=7.5 Hz, 1H), 7.63 (t, J=7.8 Hz, 2H), 4.59-4.49 (m, 2H), 4.08-4.02 (m, 2H). $^{13}C$ NMR (100 MHz, $CDCl_3$) δ 159.1, 137.8, 135.9, 129.9, 128.7, 110.7, 73.0, 60.5. HRMS (ESI) calcd for $C_{10}H_{10}N_2NaO_6S$ 309.0152 $[M+Na]^+$, found 309.0142.

Figure 4:
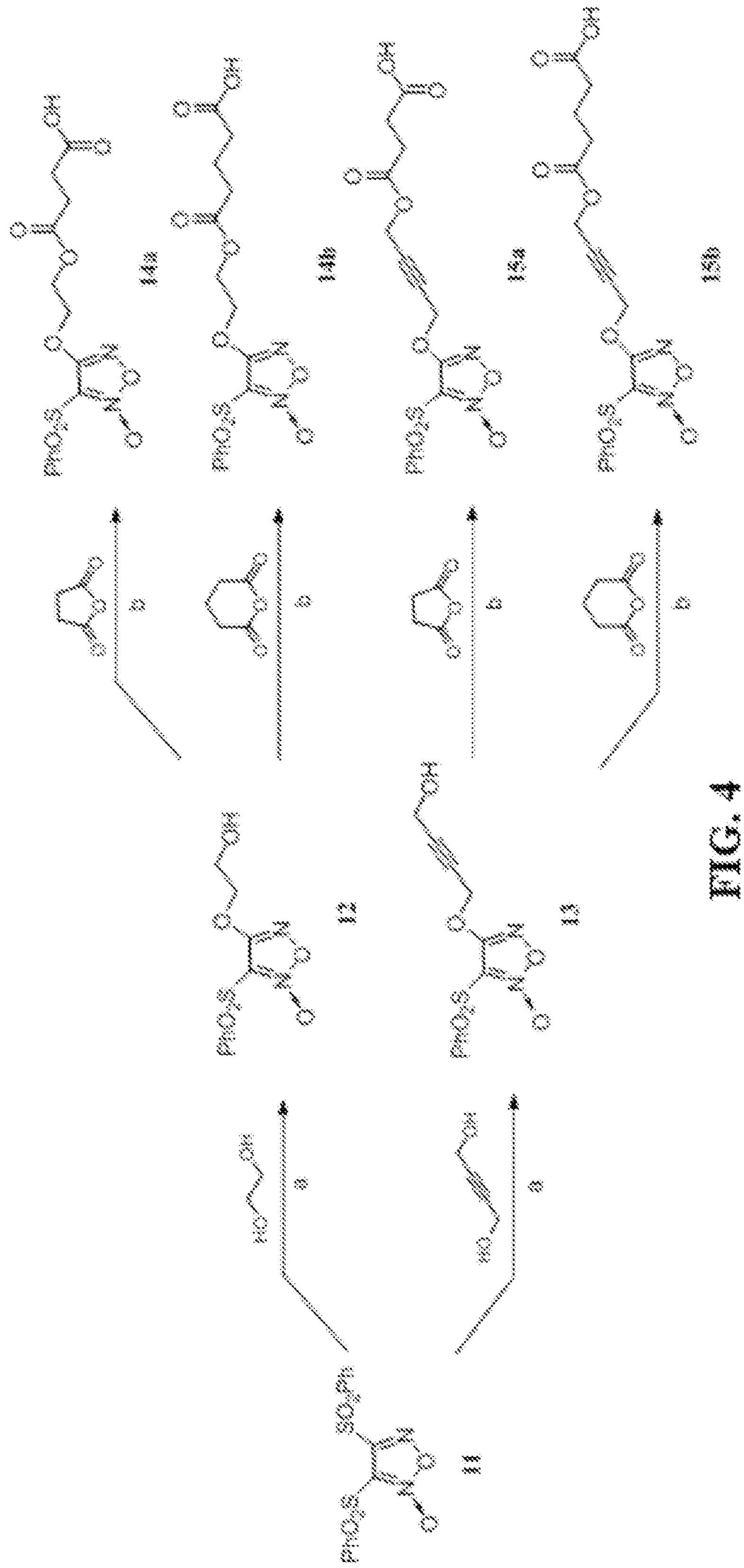
FIG. 4 shows the synthetic routes of intermediates 12, 13, 14a, 14b, 15a, and 15b.

As shown in FIG. 4, intermediate 13 was prepared according to the methods as described above, except that the reactant ethylene glycol was replaced with 1,4-butynediol. $^1H$ NMR Data of Intermediate 13

4-((4-hydroxybut-2-yn-1-yl)oxy)-3-(phenylsulfonyl)-1,2,5-oxadiazole 2-oxide (13)

White solid, yield 53%, m.p. 116-118° C. $^1H$ NMR (400 MHz, $CDCl_3$) δ8.07 (d, J=7.7 Hz, 2H), 7.76 (t, J=7.4 Hz, 1H), 7.63 (t, J=7.7 Hz, 2H), 5.10 (s, 2H), 4.34 (s, 2H). $^{13}C$ NMR (100 MHz, CDCl3) δ158.2, 138.0, 135.9, 129.8, 128.8, 110.8, 88.3, 77.7, 59.0, 51.1. HRMS (ESI) calcd for $C_{12}H_{10}N_2NaO_6S$ 333.0512 $[M+Na]^+$, found 333.0512.

(4) Preparation of Intermediates 14a, 14b, 15a, and 15b

As shown in FIG. 4, reactants succinic anhydride (76 mg, 0.76 mmol) and 4-dimethylaminopyridine DMAP (38 mg, 0.32 mmol) were added in turn to a solution of dichloromethane (5 mL) containing the intermediate 12 (182 mg, 0.63 mmol). The resulting mixture was stirred and reacted at room temperature for 6 h, obtaining a mixed solution. At room temperature, the reaction was quenched by adding water (5 mL). The stirring was continued for 10 min. The resulting mixture was subjected to extraction with dichloromethane (5 mL) for three times, and organic phases were combined. The organic phase after combining was washed with water (20 mL×2) and saturated saline (20 mL×2) in turn, and dried with anhydrous sodium sulfate, obtaining a dried organic phase. The dried organic phase was distilled under reduced pressure, obtaining a residue. The residue was purified by silica gel column chromatography (dichloromethane:methanol of 150:1, v/v), obtaining a white solid, i.e., intermediate 14a (167 mg, 67%).

m.p. 118-120° C. $^1H$ NMR (400 MHz, $CDCl_3$) δ 8.07 (d, J=7.3 Hz, 2H), 7.76 (t, J=7.5 Hz, 1H), 7.63 (t, J=7.9 Hz, 2H), 4.72-4.59 (m, 2H), 4.57-4.44 (m, 2H), 2.92-2.51 (m, 4H). $^{13}C$ NMR (100 MHz, $CDCl_3$) δ 176.9, 171.9, 158.8, 138.2, 135.8, 129.8, 128.8, 110.6, 69.0, 61.6, 29.0, 28.9. HRMS (ESI) calcd for $C_{14}H_{14}N_2NaO_9S$ 409.0312 $[M+Na]^+$, found 409.0295.

As shown in in FIG. 4, intermediates 14b, 15a, and 15b were prepared according to methods described above, except that the reactants were replaced accordingly. $^1H$ NMR Data of Intermediates 14b, 15a, and 15b 4-(2((4-carboxybutyryl)oxy)ethyoxyl)-3-(phenylsulfonyl)-1,2,5-oxadiazole 2-oxide (14b)

White solid, yield 53%, m.p. 91-93° C. $^1H$ NMR (400 MHz, $CDCl_3$) δ8.06 (d, J=8.1 Hz, 2H), 7.76 (t, J=7.5 Hz, 1H), 7.62 (t, J=7.8 Hz, 2H), 4.66-4.60 (m, 2H), 4.55-4.48 (m, 2H), 2.47 (q, J=7.0 Hz, 4H), 1.98 (p, J=7.2 Hz, 2H). $^{13}C$ NMR (100 MHz, $CDCl_3$) δ178.6, 172.7, 158.8, 138.0, 135.8, 129.8, 128.8, 110.6, 69.0, 61.3, 33.0, 32.9, 19.7. HRMS (ESI) calcd for $C_{15}H_{16}N_2NaO_9S$ 423.0469 $[M+Na]^+$, found 423.0465.

4-((4-((3-carboxylpropionyl)oxy)but-2-yn-1-yl)oxy)-3-(phenylsulfonyl)-1,2,5-oxadiazole 2-oxide (15a)

White solid, yield 54%, m.p. 106-108° C. $^1H$ NMR (400 MHz, $CDCl_3$) δ8.07 (d, J=7.4 Hz, 2H), 7.77 (t, J=7.5 Hz, 1H), 7.63 (t, J=7.9 Hz, 2H), 5.10 (s, 2H), 4.77 (s, 2H), 2.70 (dt, J=8.1, 4.7 Hz, 4H). $^{13}C$ NMR (100 MHz, $CDCl_3$) δ177.2, 171.4, 158.1, 138.1, 135.9, 129.9, 128.8, 110.8, 83.9, 78.8, 58.8, 52.3, 28.8, 28.8. HRMS (ESI) calcd for $C_{16}H_{14}N_2NaO_9S$ 433.0312 $[M+Na]^+$, found 433.0317.

4-(4((4-carboxybutyryl)oxy)but-2-yn-1-yloxy)-3-(phenylsulfonyl)-1,2,5-oxadiazole 2-oxide (15b)

White solid, yield 54%, m.p. 94-96° C. $^1H$ NMR (400 MHz, $CDCl_3$) δ8.07 (d, J=7.6 Hz, 2H), 7.77 (t, J=7.5 Hz, 1H), 7.63 (t, J=7.8 Hz, 2H), 5.10 (s, 2H), 4.74 (s, 2H), 2.46 (td, J=7.3, 4.9 Hz, 4H), 1.97 (p, J=7.3 Hz, 2H). $^{13}C$ NMR (100 MHz, $CDCl_3$) δ179.0, 172.1, 158.0, 137.7, 135.8, 129.8, 128.7, 110.6, 83.9, 78.6, 58.6, 52.0, 32.8, 19.6. HRMS (ESI) calcd for $C_{16}H_{14}N_2NaO_9S$ 447.0469 $[M+Na]^+$, found 447.0486.

Figure 5:
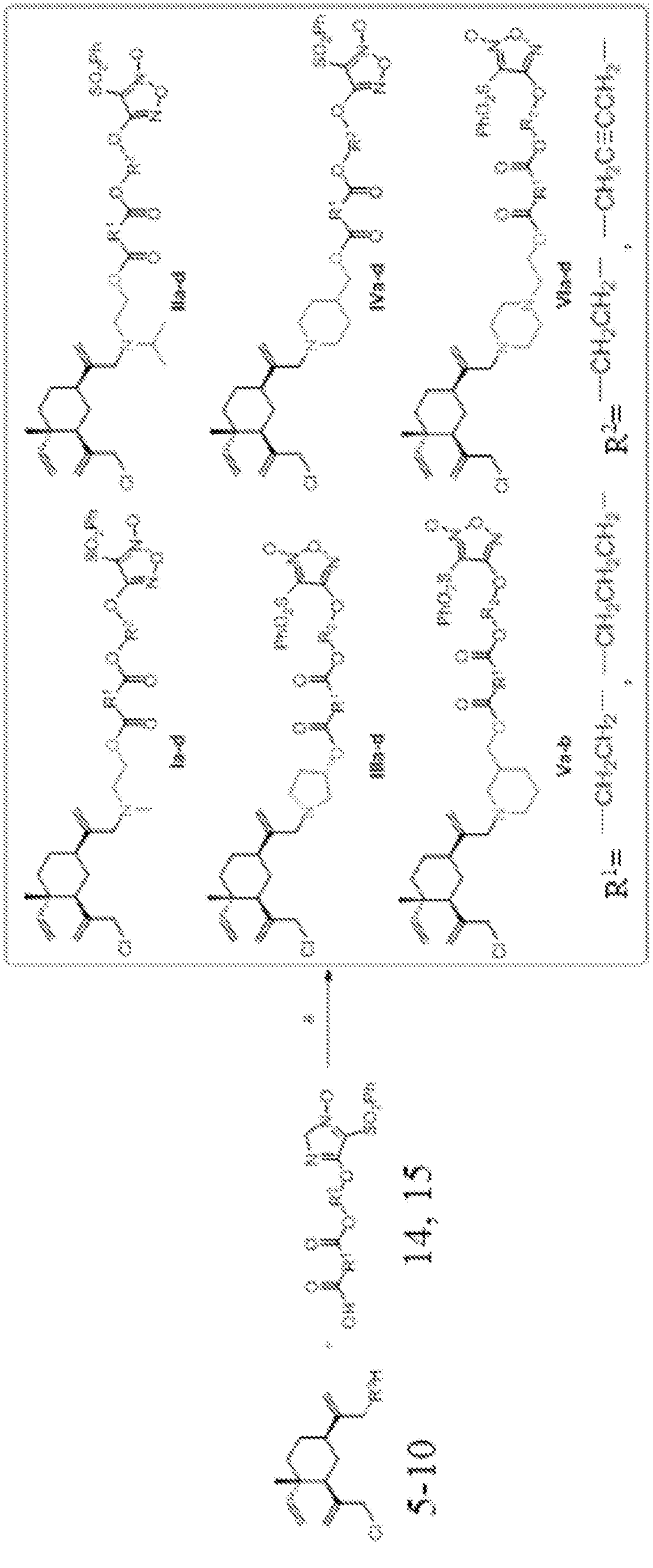
FIG. 5 shows the synthetic routes of the β-elemene nitric oxide donor derivative final products Ia-d, IIa-b, IIIa-d, IVa-d, Va-b, and VIa-b.

(5) Preparation of the β-Elemene Nitric Oxide Donor Derivative Final Products Ia-Id, IIa-IIb, IIIa-IIIb, IVa-IVd, Va-Vb, and VIa-VIb As shown in FIG. 5, the intermediates 5 to 10 (0.08 mmol), NO donor intermediates 14a, 14b, 15a, and 15b (0.10 mmol), 1-ethyl-(3-dimethylaminopropyl)carbodiimide hydrochloride (EDCI, 0.12 mmol) and DMAP (0.01 mmol) were stirred and reacted in anhydrous dichloromethane (2 mL) at room temperature for 8 h. The reaction was monitored by thin-layer chromatography. The resulting reaction mixture was diluted with dichloromethane (5 mL), obtaining an organic layer. The organic layer was washed with water and brine in turn, dried with anhydrous sodium sulfate, obtaining a dried organic layer. The dried organic layer was distilled under reduced pressure to remove solvent, obtaining a residue. The residue was purified by silica gel column chromatography (dichloromethane/methanol), obtaining a light yellow liquid.

Each intermediate used can be prepared according to (1)-(4) above and will not be repeated here.

The technical solutions provided by the present disclosure will be described in detail below with reference to the examples, but they are not to be construed as limiting the scope of protection of the present disclosure.

Example 1

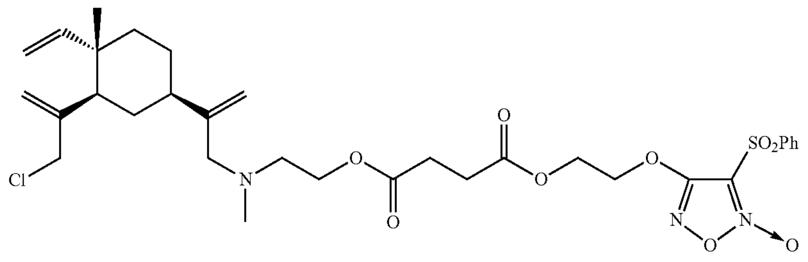

4-(2-((4-(2-((2-((1R,3R,4S)-3-(3-chloroprop-1-en-2-yl)-4-methyl-4-vinyl cyclohexyl))(methyl)amino)ethyoxyl)-4-oxobutanoyl)oxy)ethyoxyl)-3-(phenylsulfonyl)-1,2,5-oxadiazole 2-oxide was prepared according to the following procedures.

Intermediate 14a (39 mg, 0.101 mmol), DMAP (1 mg, 0.008 mmol), and EDCI (24 mg, 0.126 mmol) were added in turn to a dichloromethane (1.5 mL) solution containing intermediate 5 (26 mg, 0.084 mmol), obtaining a reactant mixture. The reactant mixture was stirred at room temperature for 8 h. The reaction product mixture was diluted with dichloromethane (5 mL), washed with water (10 mL×2) and saturated salt solution (10 mL×2) in turn, and dried with anhydrous sodium sulfate, obtaining a dried reaction product mixture. The dried reaction product mixture was distilled under reduced pressure to remove solvent, obtaining a residue. The residue was purified by silica gel column chromatography (a volume ratio of dichloromethane:methanol being 400:1), obtaining a light yellow liquid with a yield of 69%.

$^{1}$H NMR (400 MHz, $CDCl_3$) δ 8.07 (d, J=7.8 Hz, 2H), 7.75 (d, J=7.5 Hz, 1H), 7.63 (t, J=7.8 Hz, 2H), 5.78 (dd, J=17.8, 10.4 Hz, 1H), 5.26 (s, 1H), 5.02-4.87 (m, 5H), 4.65-4.59 (m, 2H), 4.57-4.48 (m, 2H), 4.21 (t, J=5.8 Hz, 2H), 4.09 (d, J=11.7 Hz, 1H), 3.96 (d, J=11.8 Hz, 1H), 3.01 (s, 2H), 2.63 (d, J=5.5 Hz, 6H), 2.32-2.22 (m, 4H), 1.66-1.42 (m, 6H), 0.97 (s, 3H). $^{13}$C NMR (100 MHz, $CDCl_3$) δ 172.0, 172.0, 158.7, 149.2, 147.7, 138.1, 135.6, 129.7, 128.6, 116.1, 111.2, 110.4, 77.0, 68.9, 62.5, 61.4, 55.3, 50.8, 47.9, 42.6, 41.5, 39.8, 33.8, 29.0, 28.9, 27.1, 15.8. HRMS (ESI) calcd for $C_{32}H_{43}ClN_3O_9S$ 680.2403 $[M+H]^+$, found 680.2441.

Example 2

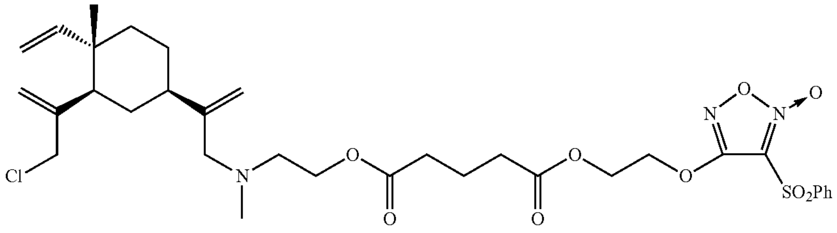

4-(2-((5-(2-((2-((1R,3R,4S)-3-(3-chloroprop-1-en-2-yl)-4-methyl-4-vinyl cyclohexyl)allyl)(methyl)amino) ethyoxyl)-5-oxopentanoyl)oxy)ethyoxyl)-3-(phenylsulfonyl)-1,2,5-oxadiazole 2-oxide was prepared basically according to the procedures as described in Example 1, except that: succinic anhydride used in (3) was replaced with glutaric anhydride.

In this example, a yellow waxy liquid was obtained, with a yield of 71%.

$^{1}$H NMR (400 MHz, $CDCl_3$) δ 8.06 (d, J=8.5 Hz, 2H), 7.76 (t, J=7.5 Hz, 1H), 7.63 (t, J=7.9 Hz, 2H), 5.87-5.71 (m, 1H), 5.26 (s, 1H), 5.01-4.86 (m, 5H), 4.67-4.60 (m, 2H), 4.53-4.46 (m, 2H), 4.17 (t, J=5.7 Hz, 2H), 4.09 (d, J=11.6 Hz, 1H), 3.96 (d, J=11.7 Hz, 1H), 2.95 (s, 2H), 2.57 (t, J=5.1 Hz, 2H), 2.43 (dt, J=17.0, 7.3 Hz, 4H), 2.28 (dd, J=11.9, 4.0 Hz, 1H), 2.16-2.07 (m, 1H), 2.02-1.93 (m, 2H), 1.65-1.35 (m, 6H), 0.96 (s, 3H). $^{13}$C NMR (100 MHz, $CDCl_3$) δ 173.0, 172.8, 158.8, 151.4, 149.4, 147.8, 138.1, 135.8, 129.8, 128.7, 116.3, 110.9, 110.5, 69.0, 63.3, 62.5, 61.2, 55.4, 51.1, 47.7, 42.9, 41.5, 39.9, 39.9, 33.9, 33.2, 33.1, 27.1, 20.0, 15.8. HRMS (ESI) calcd for $C_{33}H_{45}ClN_3O_9S$ 694.2560 $[M+H]^+$, found 694.2562.

Example 3

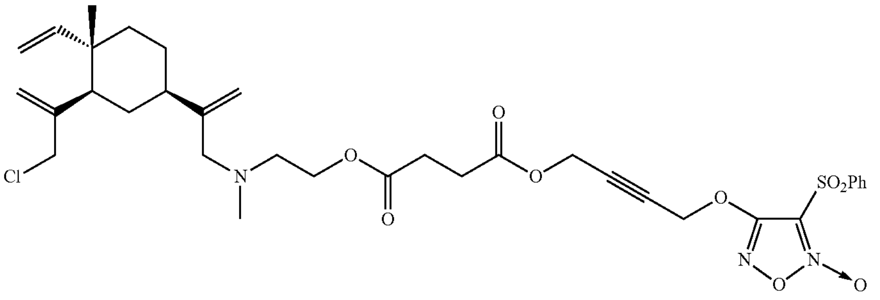

4-((4-((4-(2-((2-((1R,3R,4S)-3-(3-chloroprop-1-en-2-yl)-4-methyl-4-vinyl cyclohexyl)allyl)(methyl)amino) ethyoxyl)-4-oxobutanoyl)oxy)but-2-yn-1-yl)oxy)-3-(phenylsulfonyl)-1,2,5-oxadiazole 2-oxide was prepared basically according to the procedures as described in Example 1, except that: ethylene glycol used in (3) was replaced with 2-butyne-1,4-diol.

In this example, a yellow waxy liquid was obtained, with a yield of 74%.

$^1$H NMR (400 MHz, $CDCl_3$) δ 8.07 (d, J=7.4 Hz, 2H), 7.77 (t, J=7.5 Hz, 1H), 7.64 (t, J=7.9 Hz, 2H), 5.78 (dd, J=16.9, 11.3 Hz, 1H), 5.26 (s, 1H), 5.10 (s, 2H), 5.05-4.85 (m, 5H), 4.76 (s, 2H), 4.20 (t, J=5.6 Hz, 2H), 4.12-4.06 (m, 1H), 3.96 (d, J=11.7 Hz, 1H), 2.97 (s, 2H), 2.70-2.56 (m, 6H), 2.31-2.09 (m, 5H), 1.70-1.41 (m, 6H), 0.97 (s, 3H). $^{13}$C NMR (100 MHz, $CDCl_3$) δ 172.2, 171.6, 158.0, 151.3, 149.4, 149.4, 147.7, 137.9, 135.9, 129.9, 128.8, 116.3, 111.3, 110.7, 83.9, 78.7, 63.2, 62.8, 58.7, 55.3, 52.3, 51.1, 47.7, 42.8, 41.4, 39.9, 39.9, 33.9, 29.0, 28.9, 27.1, 15.8. HRMS (ESI) calcd for $C_{34}H_{43}ClN_3O_9S$ 704.2403 $[M+H]^+$, found 704.2408.

Example 4

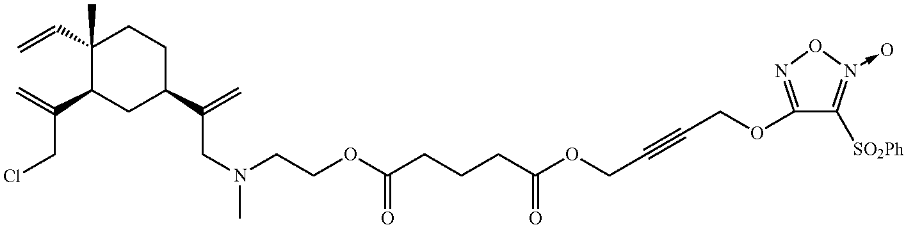

4-((4-((5-(2-((2-((1R,3R,4S)-3-(3-chloroprop-1-en-2-yl)-4-methyl-4-vinyl cyclohexyl)allyl)(methyl)amino) ethyoxyl)-5-oxopentyloxy)but-2-yn-1-yl)oxy)-3-(phenylsulfonyl)-1,2,5-oxadiazole 2-oxide was prepared basically according to the procedures as described in Example 3, except that: succinic anhydride used in (3) was replaced with glutaric anhydride.

In this example, a yellow waxy liquid was obtained, with a yield of 73%.

$^1$H NMR (400 MHz, $CDCl_3$) δ 8.07 (d, J=7.4 Hz, 2H), 7.77 (t, J=7.5 Hz, 1H), 7.63 (t, J=7.8 Hz, 2H), 5.77 (dd, J=17.1, 11.2 Hz, 1H), 5.25 (s, 1H), 5.09 (s, 2H), 4.98-4.83 (m, 5H), 4.73 (s, 2H), 4.17 (t, J=5.8 Hz, 2H), 4.09 (d, J=11.7 Hz, 1H), 3.96 (d, J=11.7 Hz, 1H), 2.96 (s, 2H), 2.57 (t, J=5.5 Hz, 2H), 2.41 (dt, J=17.1, 7.3 Hz, 4H), 2.31-2.18 (m, 4H), 2.12 (s, 1H), 1.96 (p, J=7.1 Hz, 2H), 1.68-1.41 (m, 6H), 0.96 (s, 3H). $^{13}$C NMR (100 MHz, $CDCl_3$) δ 172.9, 172.2, 158.0, 151.3, 149.3, 147.7, 137.8, 135.9, 129.8, 128.8, 116.3, 111.3, 110.9, 110.7, 84.0, 78.6, 63.2, 62.4, 58.7, 55.4, 52.0, 51.1, 47.7, 39.9, 33.8, 33.2, 33.0, 27.1, 20.0, 15.8. HRMS (ESI) calcd for $C_{35}H_{45}ClN_3O_9S$ 718.2560 $[M+H]^+$, found 718.2553.

Example 5

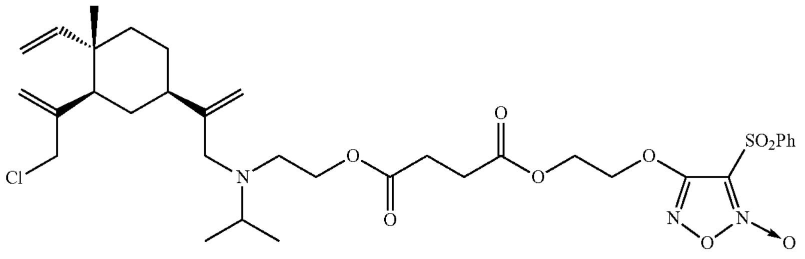

4-(2-((4-(2-((2-((1R,3R,4S)-3-(3-chloroprop-1-en-2-yl)-4-methyl-4-vinyl cyclohexyl)allyl)(isopropyl)amino) ethyoxyl)-4-oxobutanoyl)oxy)ethyoxyl)-3-(phenylsulfonyl)-1,2,5-oxadiazole 2-oxide was prepared basically according to the procedures as described in Example 1, except that: N-methyl-2-hydroxyethylamine used in (1) was replaced with 2-(isopropylamino)ethanol.

In this example, a yellow waxy liquid was obtained, with a yield of 58%.

$^1$H NMR (400 MHz, $CDCl_3$) δ 8.07 (d, J=7.5 Hz, 2H), 7.76 (t, J=7.5 Hz, 1H), 7.63 (t, J=7.8 Hz, 2H), 5.77 (dd, J=17.6, 10.6 Hz, 1H), 5.25 (s, 1H), 5.03-4.84 (m, 5H), 4.66-4.58 (m, 2H), 4.56-4.47 (m, 2H), 4.11-3.93 (m, 4H), 3.06-2.82 (m, 3H), 2.72-2.56 (m, 6H), 2.30-2.09 (m, 2H), 1.65-1.40 (m, 6H), 1.02-0.90 (m, 9H). $^{13}$C NMR (100 MHz, $CDCl_3$) δ 172.2, 172.1, 158.7, 149.8, 149.3, 147.7, 138.0, 135.7, 129.7, 128.7, 116.2, 111.2, 110.4, 110.0, 68.9, 64.0, 61.4, 55.6, 51.2, 50.2, 47.7, 41.3, 39.9, 39.9, 34.0, 28.9, 28.9, 27.1, 18.0, 17.7, 15.7. HRMS (ESI) calcd for $C_{34}H_{47}ClN_3O_9S$ 708.2716 $[M+H]^+$, found 708.2703.

Example 6

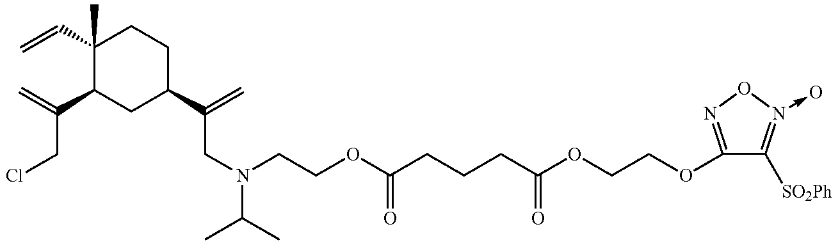

4-(2-((5-(2-((2-((1R,3R,4S)-3-(3-chloroprop-1-en-2-yl)-4-methyl-4-vinyl cyclohexyl)allyl)(isopropyl)amino) ethyoxyl)-5-oxopentyloxy)ethyoxyl)-3-(phenylsulfonyl)-1,2,5-oxadiazole 2-oxide was prepared basically according to the procedures as described in Example 2, except that: N-methyl-2-hydroxyethylamine used in (1) was replaced with 2-(isopropylamino)ethanol.

In this example, a yellow waxy liquid was obtained, with a yield of 68%.

$^1$H NMR (400 MHz, $CDCl_3$) δ 8.06 (d, J=7.4 Hz, 2H), 7.76 (t, J=7.5 Hz, 1H), 7.62 (t, J=7.8 Hz, 2H), 5.77 (dd, J=16.9, 11.3 Hz, 1H), 5.25 (s, 1H), 5.03-4.82 (m, 5H), 4.65-4.56 (m, 2H), 4.54-4.43 (m, 2H), 4.12-3.91 (m, 4H), 3.08-2.79 (m, 3H), 2.58 (t, J=6.6 Hz, 2H), 2.42 (dt, J=26.0, 7.3 Hz, 4H), 2.26 (dd, J=12.7, 3.4 Hz, 1H), 2.13 (t, J=11.3 Hz, 1H), 1.97 (p, J=7.3 Hz, 2H), 1.66-1.41 (m, 6H), 1.01-0.87 (m, 9H). $^{13}$C NMR (100 MHz, $CDCl_3$) δ 172.9, 172.8, 158.8, 149.8, 149.3, 147.8, 138.0, 135.8, 129.8, 128.7, 116.3, 111.3, 110.5, 110.1, 69.0, 63.8, 61.2, 55.6, 51.2, 50.2, 47.8, 41.4, 40.0, 39.9, 34.1, 33.2, 33.1, 27.1, 20.0, 18.1, 17.8, 15.8. HRMS (ESI) calcd for $C_{35}H_{48}ClN_3O_9S$ 722.2873 $[M+H]^+$, found 722.2873.

Example 7

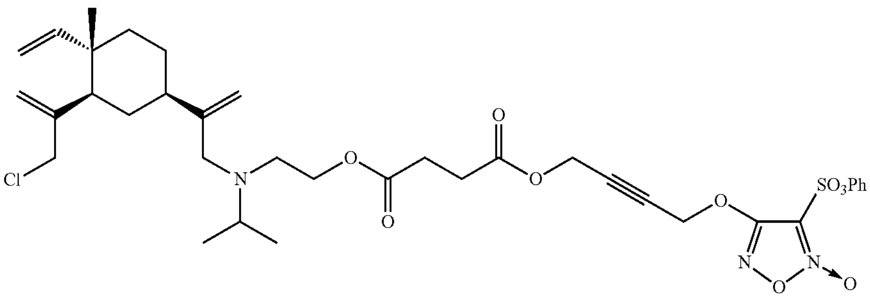

4-((4-((4-(2-((2-((1R,3R,4S)-3-(3-chloroprop-1-en-2-yl)-4-methyl-4-vinyl cyclohexyl)allyl)(isopropyl)amino) ethyoxyl)-4-oxobutanoyl)oxy)but-2-yn-1-yl)oxy)-3-(phenylsulfonyl)-1,2,5-oxadiazole 2-oxide was prepared basically according to the procedures as described in Example 3, except that: N-methyl-2-hydroxyethylamine used in (1) was replaced with 2-(isopropylamino)ethanol.

In this example, a yellow waxy liquid was obtained, with a yield of 47%.

$^1$H NMR (400 MHz, $CDCl_3$) δ 8.08 (d, J=7.7 Hz, 2H), 7.77 (t, J=7.4 Hz, 1H), 7.64 (t, J=7.8 Hz, 2H), 5.78 (dd, J=17.1, 11.1 Hz, 1H), 5.25 (s, 1H), 5.10 (s, 2H), 4.76 (s, 2H), 4.18-3.91 (m, 4H), 2.98 (d, J=45.6 Hz, 3H), 2.65 (dt, J=10.6, 5.1 Hz, 6H), 2.31-2.11 (m, 2H), 1.64-1.41 (m, 6H), 0.97 (s, 9H). $^{13}$C NMR (100 MHz, $CDCl_3$) δ 172.1, 171.6, 158.1, 149.4, 147.9, 138.1, 135.8, 129.9, 128.8, 116.2, 111.3, 110.7, 84.0, 78.8, 58.7, 55.7, 52.2, 51.1, 48.0, 47.9, 41.5, 40.0, 34.2, 29.1, 29.0, 27.3, 22.8, 18.1, 17.8, 15.9. HRMS (ESI) calcd for $C_{36}H_{47}ClN_3O_9S$ 732.2716 $[M+H]^+$, found 732.2711.

Example 8

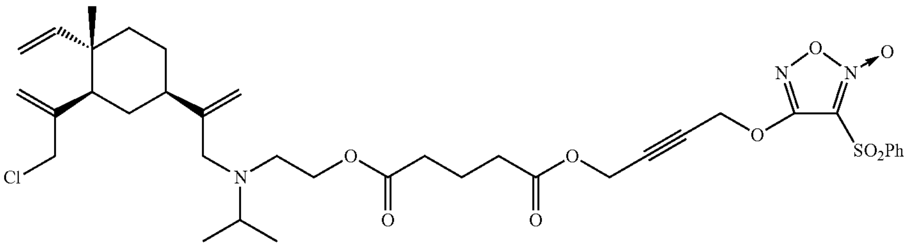

4-((4-((5-(2-((2-((1R,3R,4S)-3-(3-chloroprop-1-en-2-yl)-4-methyl-4-vinyl cyclohexyl)allyl)(isopropylamino) ethyoxyl)-5-oxopentanoyl)oxy)but-2-yn-1-yl)oxy)-3-(phenylsulfonyl)-1,2,5-oxadiazole 2-oxide was prepared basically according to the procedures as described in Example 4, except that: N-methyl-2-hydroxyethylamine used in (1) was replaced with 2-(isopropylamino)ethanol.

In this example, a yellow waxy liquid was obtained, with a yield of 53%.

$^1$H NMR (400 MHz, $CDCl_3$) δ 8.07 (d, J=7.4 Hz, 2H), 7.77 (t, J=7.5 Hz, 1H), 7.63 (t, J=7.8 Hz, 2H), 5.78 (dd, J=17.0, 11.2 Hz, 1H), 5.25 (s, 1H), 5.09 (s, 2H), 5.04-4.81 (m, 5H), 4.74 (s, 2H), 4.13-3.91 (m, 4H), 3.09-2.79 (m, 3H), 2.59 (t, J=6.2 Hz, 2H), 2.40 (dt, J=26.3, 7.4 Hz, 5H), 2.26 (dd, J=12.2, 3.5 Hz, 1H), 2.14 (s, 1H), 1.96 (p, J=7.3 Hz, 2H), 1.66-1.41 (m, 6H), 1.06-0.89 (m, 9H). $^{13}$C NMR (100 MHz, $CDCl_3$) δ 172.7, 172.0, 157.9, 149.3, 147.7, 137.9, 135.7, 129.7, 128.7, 116.1, 111.1, 110.6, 110.0, 84.0, 78.5, 63.7, 58.6, 55.6, 51.8, 51.0, 50.3, 47.9, 47.9, 41.4, 39.9, 39.9, 34.1, 33.2, 33.0, 27.1, 20.0, 18.0, 17.7, 15.8. HRMS (ESI) calcd for $C_{37}H_{49}ClN_3O_9S$ 746.2873 $[M+H]^+$, found 746.2871.

Example 9

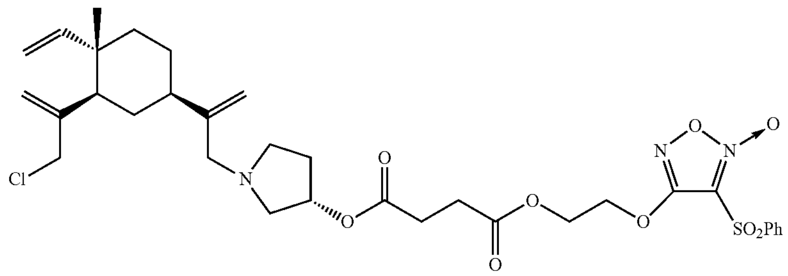

4-(2-((4-(((S)-1-(2-((1R,3R,4S)-3-(3-chloroprop-1-en-2-yl)-4-methyl-4-vinyl cyclohexyl)allyl)pyrrolidine-3-ly)oxy)-4-oxobutanoyl)oxy)ethyoxyl)-3-(phenylsulfonyl)-1,2,5-oxadiazole 2-oxide was prepared basically according to the procedures as described in Example 1, except that: N-methyl-2-hydroxyethylamine used in (1) was replaced with (R)-3-hydroxypyrrolidine.

In this example, a yellow waxy liquid was obtained, with a yield of 68%.

$^1$H NMR (400 MHz, $CDCl_3$) δ 8.06 (d, J=7.5 Hz, 2H), 7.76 (t, J=7.5 Hz, 1H), 7.63 (t, J=7.8 Hz, 2H), 5.77 (dd, J=17.1, 11.2 Hz, 1H), 5.26 (s, 1H), 5.17 (s, 1H), 5.00-4.83 (m, 5H), 4.66-4.57 (m, 2H), 4.56-4.48 (m, 2H), 4.09 (d, J=11.6 Hz, 1H), 3.96 (d, J=11.7 Hz, 1H), 3.12 (d, J=13.4 Hz, 1H), 2.99 (d, J=13.4 Hz, 1H), 2.76-2.60 (m, 7H), 2.40 (s, 1H), 2.31-2.19 (m, 2H), 1.87-1.79 (m, 1H), 1.67-1.40 (m, 6H), 0.96 (s, 3H). $^{13}$C NMR (100 MHz, $CDCl_3$) δ 172.2, 172.2, 158.8, 149.3, 147.7, 138.0, 135.8, 129.8, 128.7, 116.2, 111.3, 110.5, 74.7, 68.9, 61.5, 60.8, 60.0, 53.0, 51.1, 47.6, 42.0, 39.9, 39.8, 34.0, 31.9, 29.2, 29.0, 27.1, 15.8. HRMS (ESI) calcd for $C_{33}H_{43}ClN_3O_9S$ 692.2403 $[M+H]^+$, found 692.2394.

Example 10

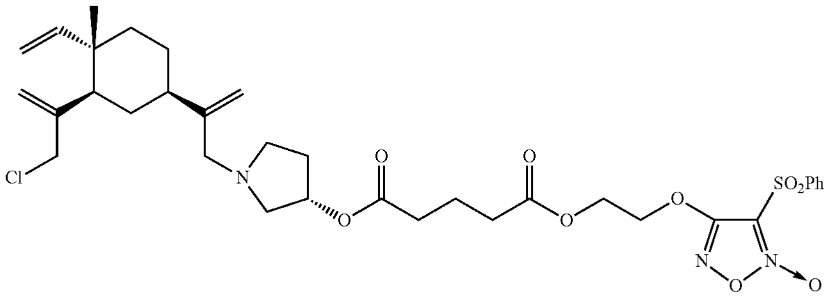

4-(2-((5-(((S)-1-(2-((1R,3R,4S)-3-(3-chloroprop-1-en-2-yl)-4-methyl-4-vinyl cyclohexyl)allyl)pyrrolidine-3-ly)oxy)-5-oxopentanoyl)ethyoxyl)-3-(phenylsulfonyl)-1,2,5-oxadiazole 2-oxide was prepared basically according to the procedures as described in Example 2, except that: N-methyl-2-hydroxyethylamine used in (1) was replaced with (R)-3-hydroxypyrrolidine.

In this example, a yellow waxy liquid was obtained, with a yield of 62%.

$^1$H NMR (400 MHz, $CDCl_3$) δ 8.05 (d, J=7.5 Hz, 2H), 7.76 (t, J=7.5 Hz, 1H), 7.63 (t, J=7.8 Hz, 2H), 5.77 (dd, J=17.0, 11.2 Hz, 1H), 5.25 (s, 1H), 5.16 (s, 1H), 5.03-4.85 (m, 5H), 4.66-4.59 (m, 2H), 4.53-4.46 (m, 2H), 4.09 (d, J=11.6 Hz, 1H), 3.96 (d, J=11.7 Hz, 1H), 3.17-2.91 (m, 2H), 2.71 (d, J=6.6 Hz, 2H), 2.59 (d, J=9.8 Hz, 1H), 2.42 (dt, J=23.1, 7.3 Hz, 5H), 2.31-2.19 (m, 2H), 2.11 (s, 1H), 2.00-1.92 (m, 2H), 1.85-1.76 (m, 1H), 1.67-1.40 (m, 6H), 0.96 (s, 3H). $^{13}$C NMR (100 MHz, $CDCl_3$) δ 172.9, 172.8, 158.8, 149.3, 147.7, 138.0, 135.8, 129.8, 128.7, 116.2, 111.3, 110.5, 74.4, 69.0, 61.2, 60.9, 60.0, 53.0, 51.1, 47.6, 42.0, 39.9, 39.8, 34.0, 33.4, 33.1, 32.0, 27.1, 20.0, 15.8. HRMS (ESI) calcd for $C_{34}H_{45}ClN_3O_9S$ 706.2560 $[M+H]^+$, found 706.2555.

Example 11

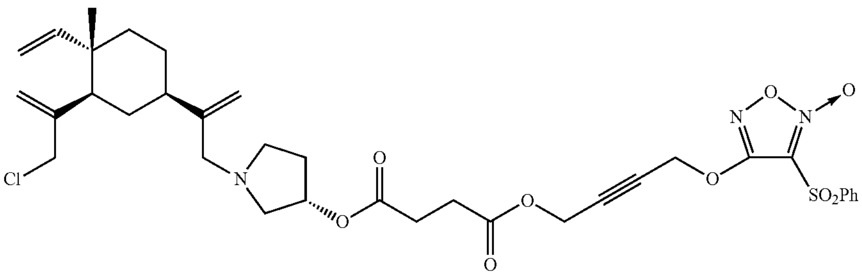

4-((4-((4-(((S)-1-(2-((1R,3R,4S)-3-(3-chloroprop-1-en-2-yl)-4-methyl-4-vinyl cyclohexyl)allyl)pyrrolidine-3-ly) oxy)-4-oxobutanoyl)oxy)but-2-yn-1-yl)oxy)-3-(phenylsulfonyl)-1,2,5-oxadiazole 2-oxide was prepared basically according to the procedures as described in Example 3, except that: N-methyl-2-hydroxyethylamine used in (1) was replaced with (R)-3-hydroxypyrrolidine.

In this example, a yellow waxy liquid was obtained, with a yield of 53%.

$^{1}$H NMR (400 MHz, $CDCl_3$) δ 8.07 (d, J=7.4 Hz, 2H), 7.77 (t, J=7.5 8Hz, 1H), 7.63 (t, J=7.9 Hz, 2H), 5.78 (dd, J=17.9, 10.3 Hz, 1H), 5.26 (s, 1H), 5.19 (s, 1H), 5.09 (s, 2H), 5.02-4.84 (m, 5H), 4.76 (s, 2H), 4.09 (d, J=11.4 Hz, 1H), 3.97 (d, J=11.8 Hz, 1H), 3.16-2.95 (m, 2H), 2.76-2.60 (m, 7H), 2.41 (s, 1H), 2.31-2.08 (m, 3H), 1.88-1.79 (m, 1H), 1.68-1.43 (m, 6H), 0.97 (s, 3H). $^{13}$C NMR (100 MHz, $CDCl_3$) δ 172.0, 171.6, 158.1, 149.4, 147.8, 147.8, 138.0, 135.8, 129.8, 128.8, 116.2, 111.3, 110.7, 84.0, 78.8, 74.8, 60.9, 60.0, 58.7, 53.0, 52.2, 51.0, 47.9, 42.2, 39.9, 39.9, 34.1, 32.0, 29.2, 29.0, 27.2, 15.9. HRMS (ESI) calcd for $C_{35}H_{43}ClN_3O_9S$ 716.2403 $[M+H]^+$, found 716.2400.

Example 12

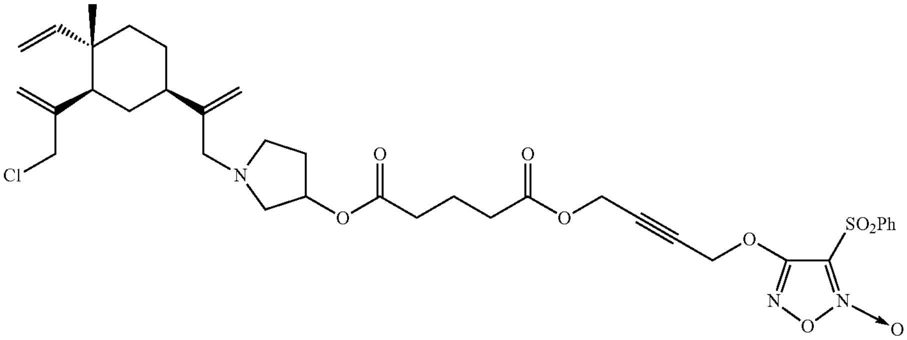

4-((4-((5-(((S)-1-(2-((1R,3R,4S)-3-(3-chloroprop-1-en-2-yl)-4-methyl-4-vinyl cyclohexyl)allyl)pyrrolidine-3-ly) oxy)-5-oxopentanoyl)oxy)but-2-yn-1-yl)oxy)-3-(phenylsulfonyl)-1,2,5-oxadiazole 2-oxide was prepared basically according to the procedures as described in Example 4, except that: N-methyl-2-hydroxyethylamine used in (1) was replaced with (R)-3-hydroxypyrrolidine.

In this example, a yellow waxy liquid was obtained, with a yield of 63%.

$^{1}$H NMR (400 MHz, $CDCl_3$) δ 8.07 (d, J=7.4 Hz, 2H), 7.76 (t, J=7.5 Hz, 1H), 7.63 (t, J=7.8 Hz, 2H), 5.78 (dd, J=17.9, 10.3 Hz, 1H), 5.26 (s, 1H), 5.17 (td, J=6.2, 3.2 Hz, 1H), 5.09 (s, 2H), 5.01-4.82 (m, 5H), 4.74 (s, 2H), 4.09 (d, J=11.5 Hz, 1H), 3.96 (d, J=11.8 Hz, 1H), 3.11 (d, J=13.4 Hz, 1H), 2.99 (d, J=13.4 Hz, 1H), 2.78-2.66 (m, 2H), 2.60 (d, J=10.9 Hz, 1H), 2.40 (dt, J=23.9, 7.3 Hz, 5H), 2.31-2.17 (m, 2H), 2.10 (dq, J=7.6, 5.3, 3.5 Hz, 1H), 1.95 (p, J=7.3 Hz, 2H), 1.81 (dq, J=13.7, 8.7, 6.9 Hz, 1H), 1.70-1.39 (m, 6H), 0.97 (s, 3H). $^{13}$C NMR (100 MHz, $CDCl_3$) δ 172.8, 172.2, 158.0, 151.1, 149.3, 147.7, 137.8, 135.9, 129.8, 128.7, 116.2, 111.3, 110.7, 110.4, 84.0, 78.6, 74.4, 60.8, 60.0, 58.7, 53.0, 52.0, 51.0, 47.6, 42.0, 39.9, 39.8, 34.0, 33.3, 33.0, 31.9, 27.1, 20.0, 15.8. HRMS (ESI) calcd for $C_{36}H_{45}ClN_3O_9S$ 730.2560 $[M+H]^+$, found 730.255.

Example 13

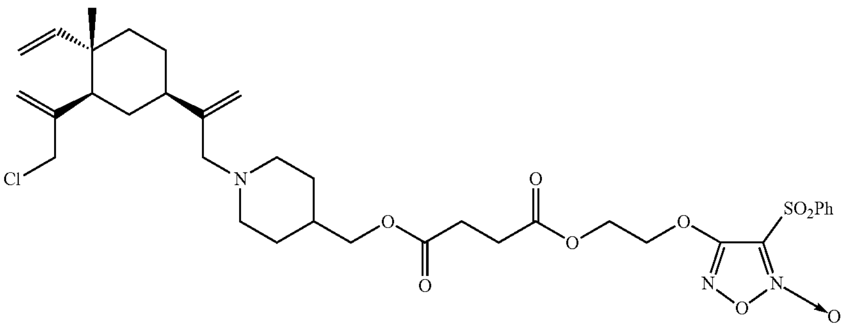

4-(2-((4-((1-(2-((1R,3R,4S)-3-(3-chloroprop-1-en-2-yl)-4-methyl-4-vinyl cyclohexyl)allyl)piperidin-4-yl) methoxyl)-4-oxobutanoyl)oxy)ethyoxyl)-3-(phenylsulfonyl)-1,2,5-oxadiazole 2-oxide was prepared basically according to the procedures as described in Example 1, except that: N-methyl-2-hydroxyethylamine used in (1) was replaced with 4-(hydroxymethyl)piperidine.

In this example, a yellow waxy liquid was obtained, with a yield of 67%.

$^{1}$H NMR (400 MHz, $CDCl_3$) δ 8.06 (d, J=7.7 Hz, 2H), 7.76 (t, J=7.5 Hz, 1H), 7.63 (t, J=7.8 Hz, 2H), 5.78 (dd, J=17.1, 11.1 Hz, 1H), 5.25 (s, 1H), 4.97-4.84 (m, 5H), 4.66-4.56 (m, 2H), 4.57-4.47 (m, 2H), 4.13-3.88 (m, 3H), 2.88 (d, J=17.1 Hz, 4H), 2.68 (s, 4H), 2.34-2.20 (m, 1H), 2.12 (s, 1H), 1.85 (s, 2H), 1.70-1.38 (m, 10H), 0.96 (s, 3H). $^{13}$C NMR (100 MHz, $CDCl_3$) δ 172.25, 172.15, 158.69, 149.29, 147.72, 137.94, 135.74, 129.73, 128.66, 116.14, 111.18, 110.43, 69.29, 68.86, 63.64, 61.42, 53.42, 53.28, 51.08, 47.62, 42.10, 39.85, 39.74, 35.34, 33.91, 28.94, 28.92, 26.95, 15.69. HRMS (ESI) calcd for $C_{35}H_{47}ClN_3O_9S$ 720.2716 $[M+H]^+$, found 720.2709.

Example 14

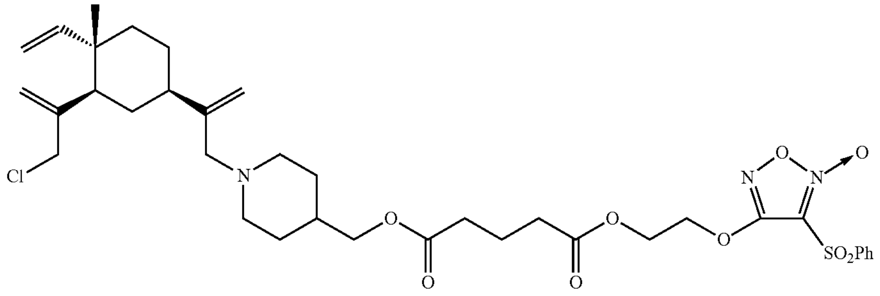

4-(2-((5-((1-(2-((1R,3R,4S)-3-(3-chloroprop-1-en-2-yl)-4-methyl-4-vinyl cyclohexyl)allyl)piperidin-4-yl) methoxyl)-5-oxopentanoyl)oxy)ethyoxyl)-3-(phenylsulfonyl)-1,2,5-oxadiazole 2-oxide was prepared basically according to the procedures as described in Example 2, except that: N-methyl-2-hydroxyethylamine used in (1) was replaced with 4-(hydroxymethyl)piperidine.

In this example, a yellow waxy liquid was obtained, with a yield of 70%.

$^{1}$H NMR (400 MHz, $CDCl_3$) δ 8.06 (d, J=7.4 Hz, 2H), 7.76 (t, J=7.5 Hz, 1H), 7.62 (t, J=7.9 Hz, 2H), 5.78 (dd, J=18.0, 10.3 Hz, 1H), 5.26 (s, 1H), 5.01-4.85 (m, 5H), 4.72-4.59 (m, 2H), 4.54-4.46 (m, 2H), 4.08 (d, J=11.7 Hz, 1H), 3.98-3.90 (m, 3H), 3.03-2.80 (m, 4H), 2.42 (dt, J=18.4, 7.3 Hz, 4H), 2.31-2.23 (m, 1H), 2.15-2.07 (m, 1H), 2.03-1.86 (m, 4H), 1.68-1.42 (m, 10H), 0.97 (s, 3H). $^{13}$C NMR (100 MHz, $CDCl_3$) δ 173.0, 172.8, 158.8, 149.4, 147.8, 138.1, 135.8, 129.8, 128.7, 116.2, 111.3, 110.5, 69.0, 69.0, 63.6, 61.2, 53.4, 53.3, 51.1, 47.8, 42.2, 39.9, 39.8, 35.4, 34.0, 33.3, 33.2, 29.8, 28.8, 27.1, 20.1, 15.8. HRMS (ESI) calcd for $C_{36}H_{49}ClN_3O_9S$ 734.2873 $[M+H]^+$, found 734.889.

Example 15

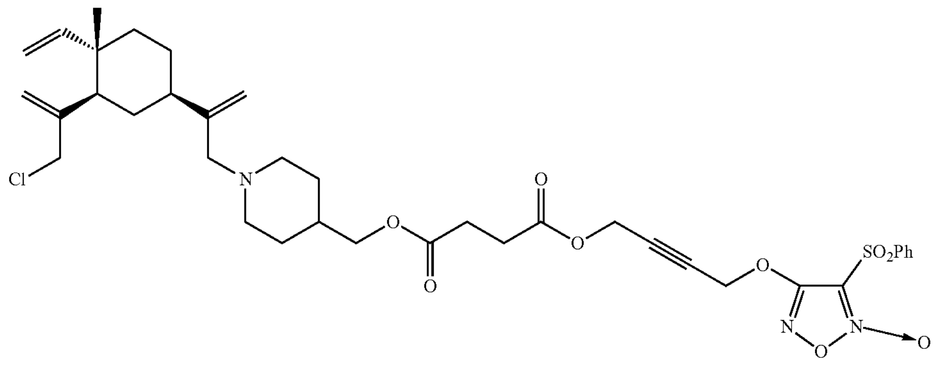

4-((4-((4-((1-(2-((1R,3R,4S)-3-(3-chloroprop-1-en-2-yl)-4-methyl-4-vinyl cyclohexyl)allyl)piperidin-4-yl)methoxyl)-4-oxobutanoyl)oxy)but-2-yn-1-yl)oxy)-3-(phenylsulfonyl)-1,2,5-oxadiazole 2-oxide was prepared basically according to the procedures as described in Example 3, except that: N-methyl-2-hydroxyethylamine used in (1) was replaced with 4-(hydroxymethyl)piperidine.

In this example, a yellow waxy liquid was obtained, with a yield of 65%.

$^1$H NMR (400 MHz, $CDCl_3$) δ 8.07 (d, J=7.4 Hz, 2H), 7.76 (t, J=7.5 Hz, 1H), 7.63 (t, J=7.8 Hz, 2H), 5.78 (dd, J=17.9, 10.4 Hz, 1H), 5.26 (s, 1H), 5.09 (s, 2H), 5.02-4.85 (m, 5H), 4.76 (s, 2H), 4.08 (d, J=11.4 Hz, 1H), 3.99-3.94 (m, 3H), 2.98 (s, 4H), 2.66 (q, J=3.7 Hz, 4H), 2.30-2.25 (m, 1H), 2.17-2.11 (m, 1H), 1.97 (d, J=17.5 Hz, 2H), 1.71-1.43 (m, 10H), 0.97 (s, 3H). $^{13}$C NMR (100 MHz, $CDCl_3$) δ 172.1, 171.6, 158.1, 149.3, 147.9, 138.1, 135.8, 129.8, 128.8, 116.1, 111.3, 110.7, 84.0, 78.8, 69.1, 65.7, 63.5, 58.7, 53.4, 53.3, 52.2, 50.9, 48.0, 42.3, 39.9, 39.9, 35.3, 34.1, 29.8, 29.1, 29.0, 27.2, 15.9. HRMS (ESI) calcd for $C_{37}H_{47}ClN_3O_9S$ 744.2716 $[M+H]^+$, found 744.2700.

Example 16

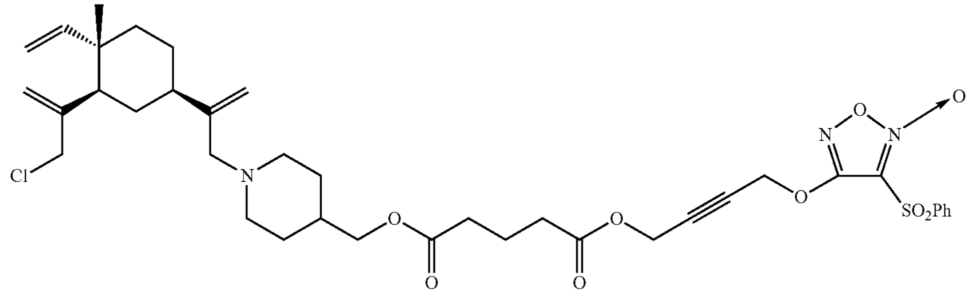

4-((4-((5-((1-(2-((1R,3R,4S)-3-(3-chloroprop-1-en-2-yl)-4-methyl-4-vinyl cyclohexyl)allyl)piperidin-4-yl)methoxyl)-5-oxopentanoyl)oxy)but-2-yn-1-yl)oxy)-3-(phenylsulfonyl)-1,2,5-oxadiazole 2-oxide was prepared basically according to the procedures as described in Example 4, except that: N-methyl-2-hydroxyethylamine used in (1) was replaced with 4-(hydroxymethyl)piperidine.

In this example, a yellow waxy liquid was obtained, with a yield of 60%.

$^1$H NMR (400 MHz, $CDCl_3$) δ 8.07 (d, J=7.5 Hz, 2H), 7.77 (t, J=7.5 Hz, 1H), 7.63 (t, J=7.8 Hz, 2H), 5.78 (dd, J=17.5, 10.8 Hz, 1H), 5.25 (s, 1H), 5.09 (s, 2H), 5.00-4.85 (m, 5H), 4.74 (s, 2H), 4.09 (d, J=11.6 Hz, 1H), 4.01-3.87 (m, 3H), 2.89 (d, J=17.0 Hz, 4H), 2.41 (dt, J=18.4, 7.3 Hz, 5H), 2.30-2.23 (m, 1H), 2.16-2.06 (m, 1H), 2.04-1.77 (m, 5H), 1.73-1.39 (m, 10H), 0.96 (s, 3H). $^{13}$C NMR (100 MHz, $CDCl_3$) δ 173.0, 172.2, 158.0, 149.4, 147.8, 137.8, 135.9, 129.8, 128.8, 116.2, 111.3, 110.7, 84.0, 78.6, 76.8, 69.1, 63.7, 58.7, 53.5, 53.4, 52.0, 51.1, 47.7, 42.2, 39.9, 39.8, 35.4, 34.0, 33.2, 33.0, 29.0, 27.0, 20.1, 15.8. HRMS (ESI) calcd for $C_{38}H_{49}ClN_3O_9S$ 758.2873 $[M+H]^+$, found 758.2866.

Example 17

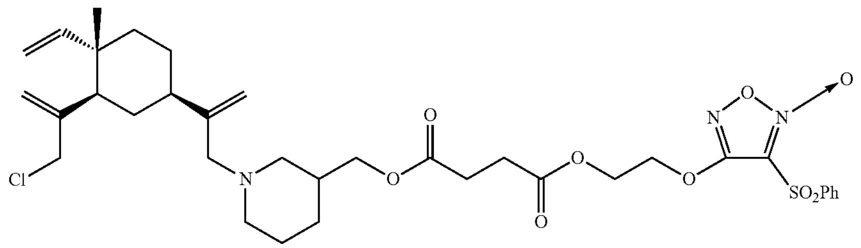

4-(2-((4-((1-(2-((1R,3R,4S)-3-(3-chloroprop-1-en-2-yl)-4-methyl-4-vinyl cyclohexyl)allyl)piperidin-3-yl) methoxyl)-4-oxobutanoyl)oxy)ethyoxyl)-3-(phenylsulfonyl)-1,2,5-oxadiazole 2-oxide was prepared basically according to the procedures as described in Example 1, except that: N-methyl-2-hydroxyethylamine used in (1) was replaced with 3-(hydroxymethyl)piperidine.

In this example, a yellow waxy liquid was obtained, with a yield of 70%.

$^1$H NMR (400 MHz, $CDCl_3$) δ 8.07 (d, J=7.4 Hz, 2H), 7.77 (t, J=7.5 Hz, 1H), 7.63 (t, J=7.9 Hz, 2H), 5.78 (dd, J=17.9, 10.3 Hz, 1H), 5.26 (s, 1H), 4.98-4.82 (m, 5H), 4.65-4.60 (m, 2H), 4.54-4.50 (m, 2H), 4.14-3.87 (m, 4H), 2.88 (s, 2H), 2.67 (t, J=3.8 Hz, 6H), 2.32-2.23 (m, 1H), 2.11 (s, 1H), 1.91 (s, 2H), 1.78-1.41 (m, 12H), 0.97 (s, 3H). $^{13}$C NMR (100 MHz, $CDCl_3$) δ 172.3, 172.2, 158.8, 151.1, 149.4, 147.8, 138.1, 135.8, 129.8, 128.8, 116.2, 111.3, 111.3, 110.5, 69.0, 67.7, 64.0, 61.5, 57.0, 54.2, 51.1, 47.8, 42.2, 39.9, 39.9, 35.7, 34.1, 34.0, 29.0, 27.3, 27.1, 24.6, 15.8. HRMS (ESI) calcd for $C_{35}H_{47}ClN_3O_9S$ 720.2716 $[M+H]^+$, found 720.2721.

Example 18

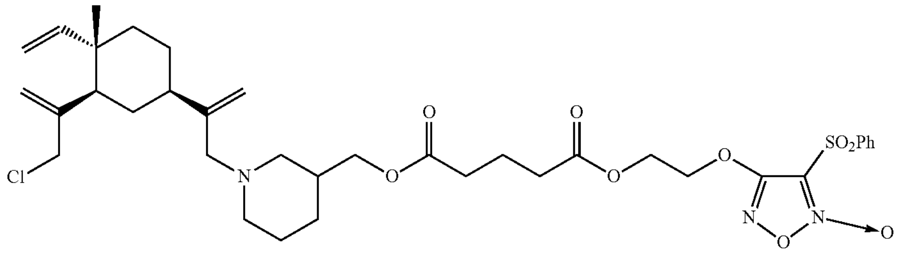

4-(2-((5-((1-(2-((1R,3R,4S)-3-(3-chloroprop-1-en-2-yl)-4-methyl-4-vinyl cyclohexyl)allyl)piperidin-3-yl) methoxyl)-5-oxopentanoyl)oxy)ethyoxyl)-3-(phenylsulfonyl)-1,2,5-oxadiazole 2-oxide was prepared basically according to the procedures as described in Example 2, except that: N-methyl-2-hydroxyethylamine used in (1) was replaced with 3-(hydroxymethyl)piperidine.

In this example, a yellow waxy liquid was obtained, with a yield of 74%.

$^1$H NMR (400 MHz, $CDCl_3$) δ 8.06 (d, J=7.5 Hz, 2H), 7.76 (t, J=7.5 Hz, 1H), 7.63 (t, J=7.8 Hz, 2H), 5.77 (dd, J=17.3, 10.9 Hz, 1H), 5.25 (s, 1H), 4.98-4.80 (m, 5H), 4.68-4.57 (m, 2H), 4.55-4.45 (m, 2H), 4.09 (d, J=11.6 Hz, 1H), 3.94 (dd, J=21.4, 11.3 Hz, 3H), 2.99-2.54 (m, 4H), 2.42 (dt, J=20.6, 7.3 Hz, 4H), 2.30-2.23 (m, 1H), 2.11 (s, 1H), 1.97 (p, J=7.3 Hz, 4H), 1.76-1.36 (m, 10H), 0.97 (s, 3H). $^{13}$C NMR (100 MHz, $CDCl_3$) δ 173.0, 172.8, 158.8, 149.4, 147.8, 138.0, 135.8, 129.8, 128.7, 116.2, 111.3, 110.5, 69.0, 67.3, 63.9, 61.2, 57.0, 54.2, 51.1, 47.8, 42.2, 39.9, 39.8, 35.7, 34.0, 34.0, 33.2, 33.1, 27.3, 27.0, 24.6, 20.0, 15.8. HRMS (ESI) calcd for $C_{36}H_{49}ClN_3O_9S$ 734.2873 $[M+H]^+$, found 734.2871.

Example 19

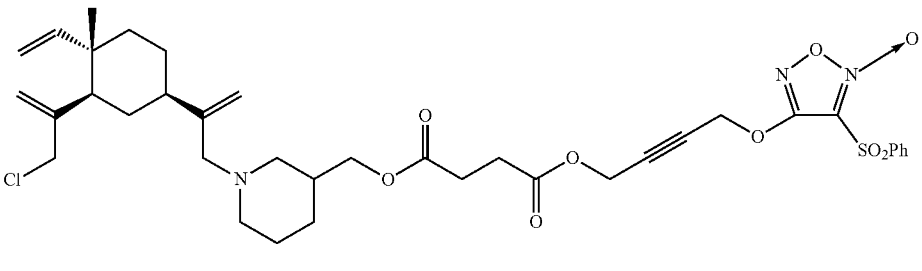

4-((4-((4-((1-(2-((1R,3R,4S)-3-(3-chloroprop-1-en-2-yl)-4-methyl-4-vinyl cyclohexyl)allyl)piperidin-3-yl) methoxyl)-4-oxobutanoyl)oxy)but-2-yn-1-yl)oxy)-3-(phenylsulfonyl)-1,2,5-oxadiazole 2-oxide was prepared basically according to the procedures as described in Example 3, except that: N-methyl-2-hydroxyethylamine used in (1) was replaced with 3-(hydroxymethyl)piperidine.

In this example, a yellow waxy liquid was obtained, with a yield of 70%.

$^{1}$H NMR (400 MHz, $CDCl_3$) δ 8.07 (d, J=7.5 Hz, 2H), 7.77 (t, J=7.5 Hz, 1H), 7.63 (t, J=7.8 Hz, 2H), 5.78 (dd, J=17.8, 10.4 Hz, 1H), 5.25 (s, 1H), 5.10 (s, 2H), 4.91 (d, J=14.0 Hz, 5H), 4.76 (s, 2H), 4.11-3.91 (m, 4H), 2.88 (s, 2H), 2.80-2.51 (m, J=3.7 Hz, 7H), 2.31-2.21 (m, 1H), 2.12 (s, 1H), 1.92 (s, 3H), 1.71-1.39 (m, 10H), 0.97 (s, 3H). $^{13}$C NMR (100 MHz, $CDCl_3$) δ 172.2, 171.6, 158.0, 149.4, 147.8, 137.9, 135.9, 129.8, 128.8, 116.2, 111.3, 110.7, 83.9, 78.7, 67.7, 63.9, 58.7, 57.0, 54.2, 52.2, 51.1, 47.8, 42.2, 39.9, 39.8, 35.7, 34.0, 29.0, 28.9, 27.3, 27.0, 24.6, 15.8. HRMS (ESI) calcd for $C_{37}H_{47}ClN_3O_9S$ 744.2716 $[M+H]^+$, found 744.2709.

Example 20

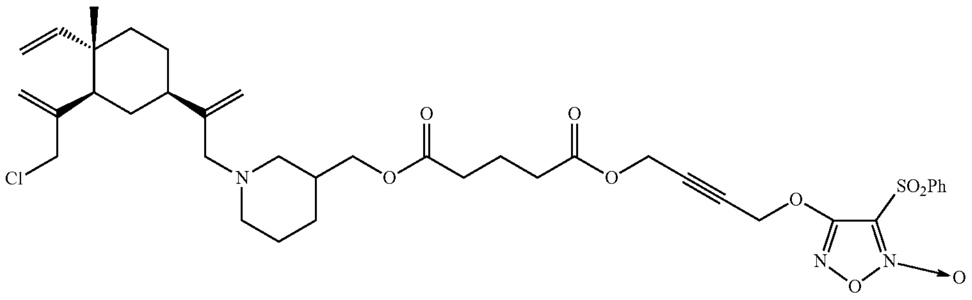

4-((4-((5-((1-(2-((1R,3R,4S)-3-(3-chloroprop-1-en-2-yl)-4-methyl-4-vinyl cyclohexyl)allyl)piperidin-3-yl) methoxyl)-5-oxopentanoyl)oxy)but-2-yn-1-yl)oxy)-3-(phenylsulfonyl)-1,2,5-oxadiazole 2-oxide was prepared basically according to the procedures as described in Example 4, except that: N-methyl-2-hydroxyethylamine used in (1) was replaced with 3-(hydroxymethyl)piperidine.

In this example, a yellow waxy liquid was obtained, with a yield of 73%.

$^{1}$H NMR (400 MHz, $CDCl_3$) δ 8.07 (d, J=7.7 Hz, 2H), 7.77 (t, J=7.5 Hz, 1H), 7.63 (t, J=7.8 Hz, 2H), 5.78 (dd, J=17.9, 10.4 Hz, 1H), 5.26 (s, 1H), 5.10 (s, 2H), 4.92 (d, J=14.0 Hz, 5H), 4.74 (s, 2H), 4.09 (d, J=11.7 Hz, 1H), 3.94 (dd, J=18.4, 11.3 Hz, 3H), 3.02-2.57 (m, 5H), 2.40 (dt, J=20.6, 7.3 Hz, 5H), 2.31-2.23 (m, 1H), 2.11 (s, 1H), 1.96 (p, J=7.3 Hz, 4H), 1.70-1.42 (m, 10H), 0.97 (s, 3H). $^{13}$C NMR (100 MHz, $CDCl_3$) δ 172.9, 172.2, 158.0, 151.1, 149.4, 147.8, 138.0, 135.9, 129.8, 128.8, 116.2, 111.3, 110.7, 84.1, 78.7, 67.4, 64.0, 58.7, 57.0, 54.2, 52.0, 51.1, 47.9, 42.3, 39.9, 39.9, 35.8, 34.1, 33.2, 33.1, 27.3, 27.1, 24.7, 20.1, 15.9. HRMS (ESI) calcd for $C_{38}H_{49}ClN_3O_9S$ 758.2873 $[M+H]^+$, found 758.2897.

Example 21

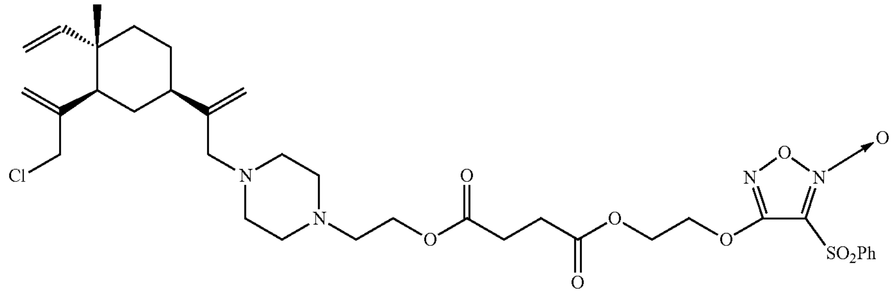

4-(2-((4-(2-(4-(2-((1R,3R,4S)-3-(3-chloroprop-1-en-2-yl)-4-methyl-4-vinyl cyclohexyl)allyl)piperazin-1-yl) ethyoxyl)-4-oxobutanoyl)oxy)ethyoxyl)-3-(phenylsulfonyl)-1,2,5-oxadiazole 2-oxide was prepared basically according to the procedures as described in Example 1, except that: N-methyl-2-hydroxyethylamine used in (1) was replaced with N-(hydroxyethyl)piperazine.

In this example, a yellow waxy liquid was obtained, with a yield of 53%.

$^1$H NMR (400 MHz, $CDCl_3$) δ 8.06 (d, J=7.3 Hz, 2H), 7.75 (t, J=7.5 Hz, 1H), 7.62 (t, J=7.8 Hz, 2H), 5.78 (dd, J=17.8, 10.4 Hz, 1H), 5.26 (s, 1H), 4.98-4.83 (m, 5H), 4.62 (dd, J=5.6, 3.5 Hz, 2H), 4.51 (dd, J=5.4, 3.6 Hz, 2H), 4.21 (t, J=6.0 Hz, 2H), 4.08 (d, J=11.6 Hz, 1H), 3.96 (d, J=11.7 Hz, 1H), 2.97-2.84 (m, 2H), 2.67 (s, 4H), 2.63 (t, J=6.0 Hz, 2H), 2.46 (d, J=40.2 Hz, 8H), 2.29-2.24 (m, 1H), 2.15-2.08 (m, 1H), 1.64-1.43 (m, 6H), 0.97 (s, 3H). $^{13}$C NMR (100 MHz, $CDCl_3$) δ 172.2, 172.1, 158.8, 150.7, 149.4, 147.9, 138.3, 135.7, 129.8, 128.8, 116.2, 111.2, 111.0, 110.5, 69.0, 63.5, 62.4, 61.5, 56.7, 53.7, 53.2, 51.0, 48.0, 42.4, 39.9, 34.1, 29.1, 29.1, 27.1, 15.9. HRMS (ESI) calcd for $C_{35}H_{48}ClN_4O_9S$ 735.2825 [M+H]$^+$, found 735.2831.

Example 22

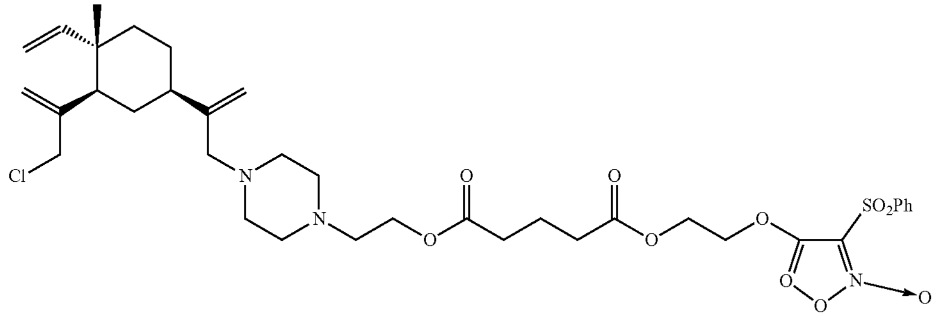

4-(2-((4-(2-(4-(2-((1R,3R,4S)-3-(3-chloroprop-1-en-2-yl)-4-methyl-4-vinyl cyclohexyl)allyl)piperazin-1-yl) ethyoxyl)-4-oxobutanoyl)oxy)ethyoxyl)-3-(phenylsulfonyl)-1,2,5-oxadiazole 2-oxide was prepared basically according to the procedures as described in Example 2, except that: N-methyl-2-hydroxyethylamine used in (1) was replaced with N-(hydroxyethyl)piperazine.

In this example, a yellow waxy liquid was obtained, with a yield of 56%.

$^1$H NMR (400 MHz, $CDCl_3$) δ 8.06 (d, J=7.3 Hz, 2H), 7.76 (t, J=7.5 Hz, 1H), 7.62 (t, J=7.9 Hz, 2H), 5.78 (dd, J=17.9, 10.4 Hz, 1H), 5.26 (s, 1H), 4.99-4.86 (m, 5H), 4.65-4.61 (m, 2H), 4.53-4.47 (m, 2H), 4.21 (t, J=5.9 Hz, 2H), 4.09 (d, J=11.1 Hz, 1H), 3.97 (d, J=11.7 Hz, 1H), 2.92 (s, 2H), 2.62 (t, J=5.9 Hz, 2H), 2.59-2.36 (m, 12H), 2.30-2.24 (m, 1H), 2.16-2.09 (m, 1H), 2.01-1.95 (m, 2H), 1.81 (s, 2H), 1.64-1.41 (m, 6H), 0.98 (s, 3H). $^{13}$C NMR (100 MHz, $CDCl_3$) δ 172.9, 172.7, 158.8, 150.7, 149.4, 147.9, 138.3, 135.8, 129.8, 128.8, 116.2, 111.3, 111.0, 110.6, 69.1, 63.5, 62.0, 61.3, 56.8, 53.6, 53.2, 51.1, 48.0, 42.4, 40.0, 34.1, 33.3, 33.2, 29.8, 27.2, 20.1, 15.9. HRMS (ESI) calcd for $C_{36}H_{50}ClN_4O_9S$ 749.2982 [M+H]$^+$, found 749.2993.

Example 23

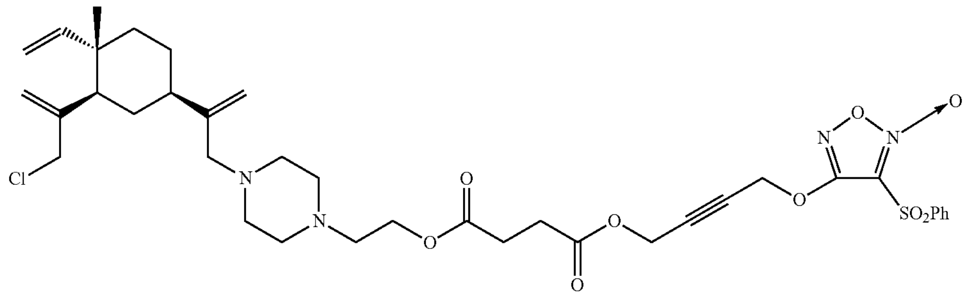

4-((4-((4-(2-(4-(2-((1R,3R,4S)-3-(3-chloroprop-1-en-2-yl)-4-methyl-4-vinyl cyclohexyl)allyl)piperazin-1-yl) ethyoxyl)-4-oxobutanoyl)oxy)but-2-yn-1-yl)oxy)-3-(phenylsulfonyl)-1,2,5-oxadiazole 2-oxide was prepared basically according to the procedures as described in Example 3, except that: N-methyl-2-hydroxyethylamine used in (1) was replaced with N-(hydroxyethyl)piperazine.

In this example, a yellow waxy liquid was obtained, with a yield of 60%.

$^1$H NMR (400 MHz, $CDCl_3$) δ 8.07 (d, J=7.5 Hz, 2H), 7.77 (t, J=7.5 Hz, 1H), 7.63 (t, J=7.8 Hz, 2H), 5.78 (dd, J=17.8, 10.4 Hz, 1H), 5.26 (s, 1H), 5.10 (s, 2H), 4.98-4.86 (m, 5H), 4.76 (s, 2H), 4.23 (t, J=5.9 Hz, 2H), 4.09 (d, J=11.6 Hz, 1H), 3.97 (d, J=11.7 Hz, 1H), 2.92 (s, 2H), 2.69-2.62 (m, 6H), 2.48 (d, J=40.6 Hz, 7H), 2.30-2.24 (m, 1H), 2.16-2.08 (m, 1H), 1.89 (s, 1H), 1.64-1.43 (m, 6H), 0.98 (s, 3H). $^{13}$C NMR (100 MHz, $CDCl_3$) δ 172.1, 171.6, 158.1, 150.7, 149.4, 147.9, 138.1, 135.8, 129.8, 128.8, 116.2, 111.3, 111.1, 110.7, 84.0, 78.8, 63.5, 62.4, 58.7, 56.7, 53.6, 53.2, 52.2, 51.1, 48.0, 42.4, 40.0, 34.1, 29.1, 29.0, 27.2, 15.9. HRMS (ESI) calcd for $C_{37}H_{48}ClN_4O_9S$ 759.2825 [M+H]$^+$, found 759.2811.

Example 24

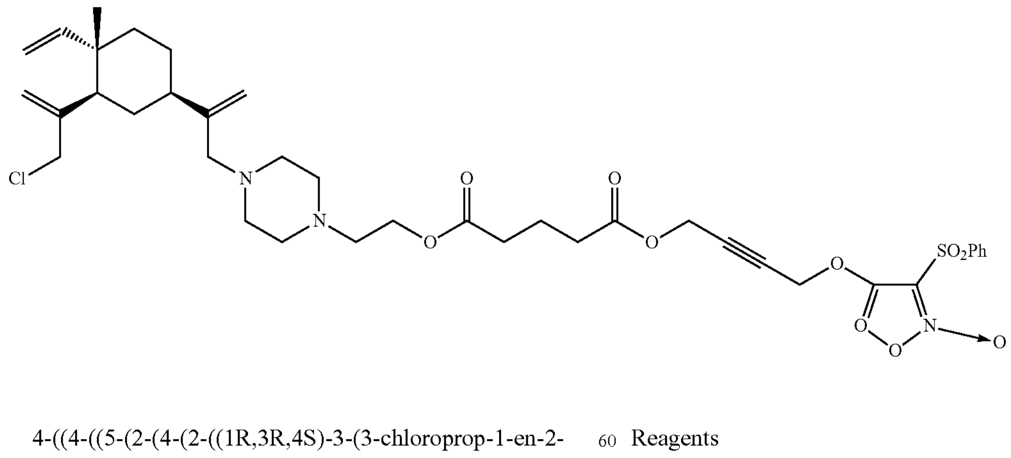

4-((4-((5-(2-(4-(2-((1R,3R,4S)-3-(3-chloroprop-1-en-2-yl)-4-methyl-4-vinyl cyclohexyl)allyl)piperazin-1-yl) ethyoxyl)-5-oxyglutaryl)oxy)but-2-yn-1-yl)oxy)-3-(phenylsulfonyl)-1,2,5-oxadiazole 2-oxide was prepared basically according to the procedures as described in Example 4, except that: N-methyl-2-hydroxyethylamine used in (1) was replaced with N-(hydroxyethyl)piperazine.

In this example, a yellow waxy liquid was obtained, with a yield of 58%.

$^1$H NMR (400 MHz, $CDCl_3$) δ 8.06 (d, J=7.5 Hz, 2H), 7.76 (t, J=7.5 Hz, 1H), 7.63 (t, J=7.9 Hz, 2H), 5.77 (dd, J=17.5, 10.7 Hz, 1H), 5.25 (s, 1H), 5.09 (s, 2H), 4.96-4.86 (m, 5H), 4.73 (s, 2H), 4.20 (t, J=5.9 Hz, 2H), 4.08 (d, J=11.5 Hz, 1H), 3.96 (d, J=11.7 Hz, 1H), 2.91 (s, 2H), 2.62 (t, J=5.9 Hz, 2H), 2.42 (dt, J=20.1, 7.3 Hz, 12H), 2.29-2.24 (m, 1H), 2.13-2.07 (m, 1H), 1.98-1.91 (m, 2H), 1.63-1.41 (m, 6H), 0.96 (s, 3H). $^{13}$C NMR (100 MHz, $CDCl_3$) δ 172.8, 172.1, 157.9, 150.5, 149.3, 147.7, 137.8, 135.8, 129.8, 128.7, 116.2, 111.2, 111.0, 110.6, 84.0, 78.6, 63.3, 61.8, 58.6, 56.7, 53.5, 53.0, 51.9, 51.1, 47.6, 42.1, 39.8, 39.7, 33.9, 33.1, 32.9, 27.0, 19.9, 15.7. HRMS (ESI) calcd for $C_{38}H_{50}ClN_4O_9S$ 773.2982 [M+H]$^+$, found 773.2974.

Pharmacodynamic Experiment

1. In Vitro NO Release Test

1.1 Experimental Equipment and Reagents

Instruments

Multifunctional enzyme marker (MD Spectramac M3, USA)

Clean bench (Suzhou Purification, China)

Reagents

Potassium dihydrogen phosphate (Aladdin Chemical Reagent Co., Ltd.)

Dipotassium hydrogen phosphate (Aladdin Chemical Reagent Co., Ltd.)

L-cysteine (Aladdin Chemical Reagent Co., Ltd.)

1.2 Experimental Method (1) Sodium nitrite solutions with different concentrations were prepared. A calibration curve was drawn.
(2) The sample was treated. A 100 μM solution was prepared. 2.5 mL of the prepared compound solution and 2.5 mL of the cysteine solution were taken and incubated at 37° C. for 120 min, and the resulting mixture was sampled at different time points.
(3) A blank hole and a standard hole were set. 160 μL of the sample was collected and mixed evenly with 0.08 mL of a developer and stood at 37° C. for 15 min. At λ=550 nm, the OD value of absorbance was measured by the enzyme marker. The NO release levels were obtained by substituting the value into the standard curve.

1.3 Test Results

TABLE 1

Results of the in vitro NO release from β-elemene derivatives prepared in Examples 1-24

| | NO-release concentrations (μM) | | | | | | |
|---|---|---|---|---|---|---|---|
| Example | 5 min | 10 min | 20 min | 30 min | 60 min | 90 min | 120 min |
| Example 1 | 1.73 | 2.31 | 2.90 | 4.04 | 7.76 | 12.67 | 17.21 |
| Example 2 | 2.10 | 2.40 | 2.84 | 3.79 | 6.74 | 10.72 | 14.97 |
| Example 3 | 10.78 | 12.02 | 15.83 | 19.79 | 32.99 | 48.39 | 58.84 |
| Example 4 | 12.53 | 14.80 | 19.55 | 23.6 | 42.31 | 66.97 | 93.18 |
| Example 5 | 0.59 | 41.61 | 48.58 | 2.57 | 5.58 | 9.22 | 13.64 |
| Example 6 | 3.38 | 5.87 | 4.62 | 6.22 | 9.97 | 15.53 | 20.60 |
| Example 7 | 5.68 | 7.17 | 9.55 | 9.04 | 20.74 | 30.04 | 40.44 |
| Example 8 | 10.55 | 12.34 | 15.52 | 18.95 | 29.50 | 43.00 | 55.33 |
| Example 9 | 3.25 | 3.90 | 5.98 | 7.59 | 11.11 | 17.29 | 23.48 |
| Example 10 | 8.39 | 9.44 | 10.65 | 12.22 | 18.15 | 26.49 | 34.97 |
| Example 11 | 9.49 | 10.79 | 14.43 | 15.99 | 24.58 | 37.37 | 50.99 |
| Example 12 | 13.20 | 16.04 | 21.29 | 26.90 | 46.58 | 74.45 | 103.92 |
| Example 13 | 11.09 | 12.18 | 14.69 | 17.13 | 25.80 | 38.78 | 51.94 |
| Example 14 | 12.34 | 13.53 | 15.94 | 18.96 | 29.94 | 45.42 | 62.49 |
| Example 15 | 8.67 | 10.07 | 12.979 | 15.92 | 25.47 | 36.31 | 48.15 |
| Example 16 | 16.99 | 18.93 | 22.62 | 27.04 | 42.47 | 64.24 | 86.29 |
| Example 17 | 4.84 | 5.66 | 6.95 | 8.44 | 12.43 | 17.81 | 22.91 |
| Example 18 | 8.89 | 10.18 | 12.42 | 14.32 | 21.50 | 32.40 | 42.83 |
| Example 19 | 13.76 | 15.87 | 19.21 | 22.88 | 34.60 | 48.73 | 56.52 |
| Example 20 | 15.19 | 17.57 | 21.33 | 25.52 | 39.29 | 58.12 | 77.28 |
| Example 21 | 0.08 | 0.41 | 0.99 | 1.64 | 2.98 | 6.43 | 10.20 |
| Example 22 | 0.33 | 0.90 | 1.35 | 1.91 | 4.05 | 7.20 | 10.51 |
| Example 23 | 4.74 | 5.95 | 7.49 | 7.63 | 8.44 | 13.57 | 17.82 |
| Example 24 | 10.64 | 11.37 | 12.38 | 13.68 | 18.24 | 25.90 | 34.64 |

As can be seen from the data in Table 1, all compounds prepared in the examples could effectively release NO, and in most of examples, the level of NO-release increases with increasing time.

2. In Vitro Anti-Tumor Activity Evaluation Test 2.1 Experimental Equipment and Reagents Instruments:
- Clean bench (Suzhou Purification Equipment Co., Ltd.)
- $CO_2$ incubator (SANYO, Japan)
- Inverted biological microscope (OLYMPUS, Japan)
- Enzyme marker (BioTek, USA)

Reagents:
- Penicillin and streptomycin mixture (Jiangsu KeyGEN Biotechnology Co., Ltd., China)
- Trypsin digestion solution (Jiangsu KeyGEN Biotechnology Co., Ltd., China)
- PBS (Jiangsu KeyGEN Biotechnology Co., Ltd., China)
- Fetal Bovine Serum (GIBCO)
- RPMI-1640 (Jiangsu KeyGEN Biotechnology Co., Ltd., China)
- DMEM (Jiangsu KeyGEN Biotechnology Co., Ltd., China)
- L-15 (Jiangsu KeyGEN Biotechnology Co., Ltd., China)
- CCK8 (Jiangsu KeyGEN Biotechnology Co., Ltd., China)
- DMSO (SIGMA)

2.2 Experimental Method (1) Cells were digested and counted. Cell suspensions (H520, SW620 5.0×104 cells/mL, and U87MG 3.5×104 cells/mL) were prepared. 100 μL of cell suspension was added to each well of a 96-well cell culture plate.
(2) The 96-well cell culture plate was incubated in a 37° C., 5%, $CO_2$ incubator for 24 h.
(3) A drug was diluted with a culture medium to a desired working solution concentration. 100 μL of the corresponding drug-containing culture medium was added to each well. At the same time, a negative control group and a positive control group were set up.
(4) The 96-well cell culture plate was incubated in a 37° C., 5%, $CO_2$ incubator for 72 h.
(5) The 96-well plate was stained with CCK-8, and at λ=450 nm, the OD value was determined.
1) 10 μL of CCK-8 was added to each well. The culture plate continued to be incubated in the incubator for 2-3 h.
2) The culture plate was rocked for 10 min to gently mix and remove air bubbles from the 96-well plate.
3) At λ=450 nm, the OD value of each well was read by the enzyme marker, and the inhibitory rates were calculated.
(6) According to the following equation (1), the growth inhibitory rate of the tumor cells was obtained. The obtained results were substituted into an IC 50 calculation software SPSS17.0 to find out the IC50 value. The IC50 results are shown in Table 1.

Equation (1)

$$\text{Cell inhibitory rate}\,\% = \frac{\text{the } OD \text{ value of the negative group} - \text{the OD value of the experimental group}}{\text{the } OD \text{ value of the negative group}} \times 100\%$$

2.3 Experimental Results

TABLE 2

Inhibitory rates of compounds prepared in Examples 1-24 (1 μM) against three human tumor cell lines in terms of antiproliferative activity

| | Inhibitory rates of compounds prepared in examples against different tumor cell lines (%) | | |
|---|---|---|---|
| Examples | SW620 | U87MG | NCI-H520 |
| β-elemene | 2.5 ± 4.1 | 4.3 ± 2.2 | 3.2 ± 0.7 |
| 13,14-dichloro-β-elemene | 3.3 ± 1.0 | 3.5 ± 1.0 | 0.9 ± 3.0 |
| Example 1 | 30.7 ± 3.5 | 39.5 ± 2.1 | 28.8 ± 0.8 |
| Example 2 | 42.3 ± 3.7 | 56.0 ± 2.1 | 48.5 ± 3.0 |
| Example 3 | 30.1 ± 5.2 | 34.9 ± 0.6 | 35.0 ± 2.2 |
| Example 4 | 47.5 ± 3.7 | 55.5 ± 1.9 | 48.7 ± 2.0 |
| Example 5 | 33.0 ± 2.5 | 47.1 ± 0.9 | 44.2 ± 1.3 |
| Example 6 | 35.6 ± 2.8 | 54.3 ± 1.3 | 43.4 ± 1.5 |
| Example 7 | 46.6 ± 1.2 | 56.7 ± 0.9 | 44.5 ± 2.2 |
| Example 8 | 10.8 ± 3.2 | 4.5 ± 1.0 | 5.6 ± 1.6 |
| Example 9 | 39.3 ± 4.2 | 51.3 ± 1.3 | 44.5 ± 2.8 |
| Example 10 | 45.9 ± 3.9 | 53.1 ± 1.4 | 46.7 ± 2.0 |
| Example 11 | 30.5 ± 3.3 | 42.0 ± 6.5 | 46.0 ± 1.0 |
| Example 12 | 31.7 ± 1.4 | 47.8 ± 1.1 | 39.1 ± 0.7 |
| Example 13 | 53.6 ± 2.4 | 52.6 ± 1.7 | 48.5 ± 2.5 |
| Example 14 | 55.4 ± 1.5 | 54.8 ± 1.9 | 50.1 ± 1.1 |
| Example 15 | 31.3 ± 0.3 | 40.5 ± 3.3 | 45.9 ± 1.4 |
| Example 16 | 39.8 ± 1.9 | 52.2 ± 3.4 | 52.3 ± 1.1 |
| Example 17 | 38.3 ± 3.0 | 51.0 ± 2.2 | 45.4 ± 1.9 |
| Example 18 | 46.1 ± 0.9 | 48.3 ± 1.5 | 43.9 ± 1.0 |
| Example 19 | 40.6 ± 2.8 | 41.9 ± 1.1 | 46.1 ± 2.7 |
| Example 20 | 43.2 ± 1.8 | 53.9 ± 0.6 | 44.5 ± 2.4 |
| Example 21 | 43.6 ± 2.5 | 52.6 ± 1.0 | 47.3 ± 2.6 |
| Example 22 | 42.8 ± 0.5 | 52.4 ± 2.0 | 44.1 ± 2.4 |
| Example 23 | 21.2 ± 2.1 | 33.4 ± 1.5 | 30.3 ± 2.9 |
| Example 24 | 43.2 ± 5.5 | 50.3 ± 1.2 | 46.8 ± 2.1 |

As can be seen from Table 2, at the concentration of 1 μM, all 24 compounds exhibit different degrees of inhibition effect against the three human tumor cells SW620, U87MG, and NCI-H520. The antiproliferative activities are significantly stronger than β-elemene and 13,14-dichloro-β-elemene, indicating that the introduction of NO donors has successfully improved the anti-tumor effect of β-elemene.

TABLE 3

$IC_{50}$ (μM) of the compounds prepared in the preferred examples against three human tumor cell lines in terms of antiproliferative activities

| | $IC_{50}$ against different tumor cell lines (μM) | | |
|---|---|---|---|
| Example | SW620 | U87MG | NCI-H520 |
| β-elemene | >100 | >100 | >100 |
| 13,14-dichloro-β-elemene | >100 | >100 | >100 |
| Example 2 | — | 0.358 ± 0.023 | 0.777 ± 0.024 |
| Example 4 | 0.858 ± 0.033 | 0.369 ± 0.013 | 0.719 ± 0.017 |
| Example 5 | — | 0.369 ± 0.025 | — |
| Example 6 | — | 0.366 ± 0.019 | — |
| Example 7 | 1.111 ± 0.115 | 0.882 ± 0.034 | — |
| Example 9 | — | 0.323 ± 0.013 | — |
| Example 10 | 1.022 ± 0.09 | 0.343 ± 0.029 | 0.848 ± 0.053 |
| Example 11 | — | — | 1.019 ± 0.041 |
| Example 12 | — | 0.898 ± 0.054 | — |
| Example 13 | 1.069 ± 0.101 | 1.119 ± 0.022 | 1.301 ± 0.043 |
| Example 14 | 0.814 ± 0.068 | 0.477 ± 0.011 | 0.846 ± 0.027 |
| Example 15 | — | — | 1.038 ± 0.033 |
| Example 16 | — | 2.160 ± 0.548 | 1.046 ± 0.013 |
| Example 17 | 1.088 ± 0.04 | 0.811 ± 0.016 | — |
| Example 18 | — | — | 1.212 ± 0.152 |
| Example 19 | — | 0.985 ± 0.012 | — |
| Example 20 | — | 1.114 ± 0.052 | 1.175 ± 0.066 |
| Example 21 | — | 0.926 ± 0.052 | — |
| Example 22 | — | 0.372 ± 0.006 | 0.962 ± 0.054 |
| Example 24 | — | 0.960 ± 0.075 | 1.062 ± 0.002 |

As shown in Table 3, the antiproliferative activities of most of compounds are significantly more potent than β-elemene and 13,14-dichloro-β-elemene. For SW620 cell line, the activities of Examples 4 and 14 are over 110-fold more active than β-elemene; for U87MG cell line, the antiproliferative activities of Examples 2, 4, 5, 6, 9, 10, and 22 are over 250-fold more potent than β-elemene; and for NCI-H520 cell line, the activities of Examples 2, 4, 10, 14, and 22 are over 100-fold more greater than β-elemene.

3. In Vivo Anti-Tumor Activity Against Malignant Brain Glioma 3.1 Subject Animals and Experimental Equipment Subject Animals:

Source, germ line, strain: BABLc/nude mice, provided by Shanghai Slaughter Laboratory Animal Co., Ltd., China.

Experimental animal production license: SOCK (Shanghai) 2017-0005

Certificate of Conformity No.: 20170005040021

Experimental animal use license: SYXK (Su) 2017-0040

Age: 4-5 weeks

Sex: female

Number of animals: 5 animals per group, 15 animals in total

Experimental Instrument:

Small animal in vivo 3D imaging system Spectrum, PerkinElmer 3.2 Preparation of a Model The cultured human brain glioma U87MG-LUC cell suspension with a concentration of 5×10 7 cells/mL was collected and each animal was inoculated in situ with 20 μL of the cell suspension. 10% chloral hydrate was injected intraperitoneally to anesthetize the mice, and the heads of the mice were fixed with a stereotaxic instrument. The skin of the head was disinfected with an alcohol swab. The skin of the head was cut along the direction of midline of the brain at its slightly right. The right hemisphere was taken as the reference point for fontanelle, 2 mm to the right of the midline, and 1 mm in front as the entry point, and the skull was ground open with a micro-abrasive drill. The cells were fully resuspended with a gun head, a syringe was used to extract the cell suspension. A vertical needle fixed by a stereotaxic instrument was used to feed 3.5 mm and quit 0.5 mm, then stood for 1 min and slowly injected the cells. After injection, the needle was stood for 1 min and slowly withdrawn. Alcohol swabs were used to disinfect the skin, and mice were put back into the feeding cages to wake up naturally after suturing the skin with stitches.

3.3 Grouping and Administration

After 14 days of cell inoculation, the animals were randomly grouped, with 5 animals in each group. At the same time, each group of nude mice began to administer drugs. The drug administration protocol is shown in the group and drug administration protocol. At the end of the experiment, the nude mice were executed immediately. The brain tissues were surgically stripped, photographed, and weighed.

3.4 In Vivo Imaging Detection

Two animals in each group were selected and injected intraperitoneally with Luc bioluminescence signal substrate, 100 μL/each animal, before administration, 1 week, 2 weeks, and 3 weeks after drug administration, respectively. 10 min later, the mice were anesthetized with isoflurane and placed on black box loading platform of an instrument for in vivo imaging detection to observe the bioluminescence signal of in situ tumors in mice's brains.

3.5 Experimental Results

Figure 6A:
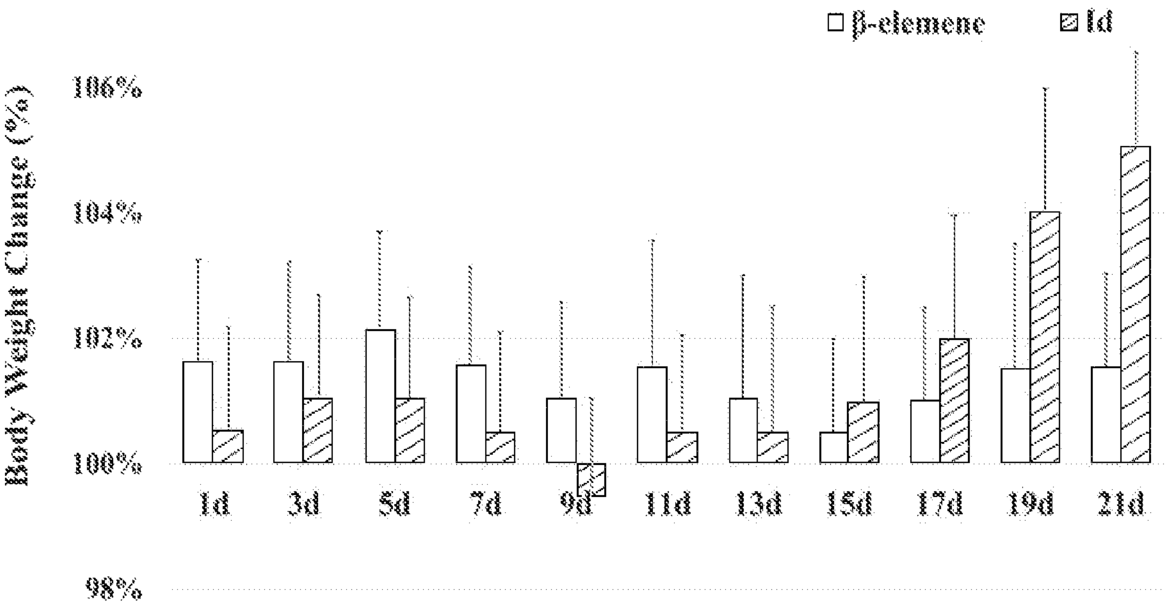
FIG. 6A shows the body weight change of β-elemene and the product prepared in Example 4 against malignant brain glioma (n=5)
Figure 6B:
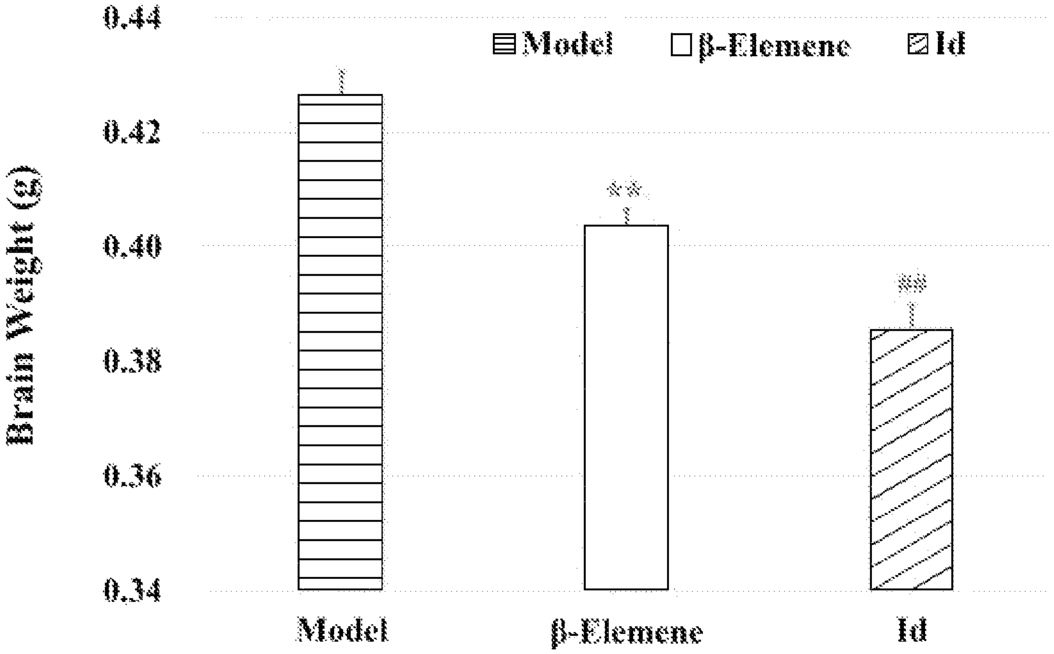
FIG. 6B shows the brain weight of β-elemene and the product prepared in Example 4 against malignant brain glioma (n=5)
Figures 6C, 6D:
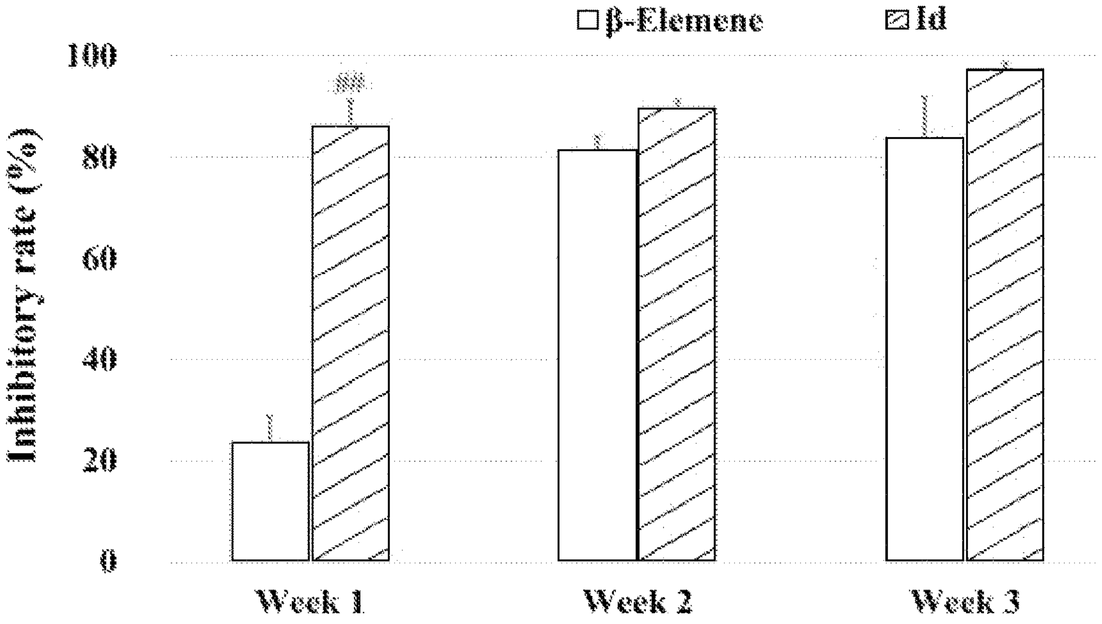
FIG. 6C shows the bioluminescence signal intensity of brain tumor of β-elemene and the product prepared in Example 4 against malignant brain glioma (n=5)
FIG. 6D shows inhibitory rates of β-elemene and the product prepared in Example 4 against malignant brain glioma (n=5).

As shown in FIG. 6, the growth of malignant brain gliomas in mice is effectively inhibited after the administration of β-elemene and Example 4 for 3 weeks. The tumor volume in the model group continues to increase (FIG. 6), but the tumor volume continues to be inhibited and significantly smaller than that in the model group after treatment with β-elemene and Example 4. In terms of brain weight, the weight of the β-elemene and Example 4 group is significantly lighter than that of the model group, and the living and physical conditions of mice are also much better than the model group. On the other hand, the bioluminescence signal intensity of gliomas in the model group continues to increase rapidly, but the bioluminescence signal intensity of β-elemene and Example 4 group declines dramatically. In the first week, the inhibitory activity of Example 4 exceeds 80%, which is significantly more potent than that of β-elemene (>20%). In the second week, both β-elemene and Example 4 reaches >80% inhibition. In the last week of administration, Example 4 blocks the tumor growth by >90%, exhibiting potent anti-malignant brain glioma activity. In summary, both β-elemene and Example 4 exhibits effective therapeutic activity, but Example 4 exhibits stronger inhibition than that of β-elemene.

The above results indicate that the introduction of NO donors effectively enhances the anti-tumor effect of β-elemene in vivo, and is a feasible strategy for the development of β-elemene based antitumor drugs.

Furthermore, it should be understood that after reading the above described contents of the present disclosure, various improvements or modifications can be made to the present disclosure by those skilled in the art, and these equivalent forms likewise fall within the scope limited by the claims appended to the present disclosure.

What is claimed is:

1. A 14-chloro-β-elemene nitric oxide donor derivative, or a pharmaceutically acceptable salt, a solvate, an enantiomer, or a diastereoisomer thereof, the 14-chloro-β-elemene nitric oxide donor derivative having a structural general formula as shown in formula (I):

(I)

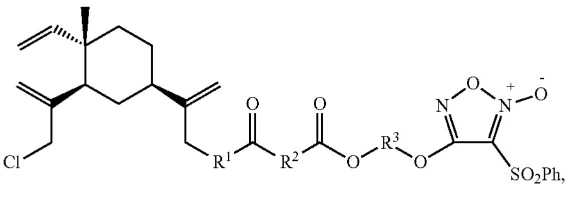

wherein in formula (I), $R^1$ is any one selected from the group consisting of

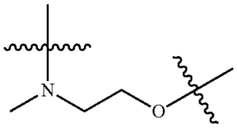
,
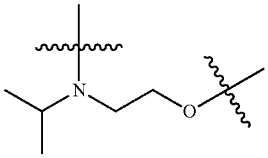
,
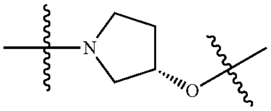
,
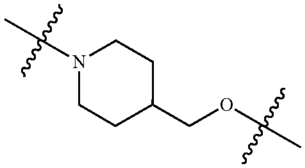
,
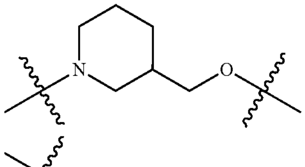
,
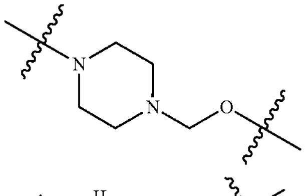
,
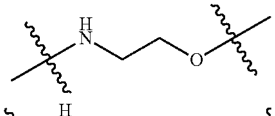
,
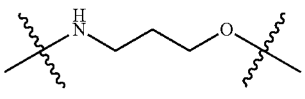
, -continued

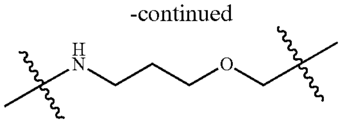,

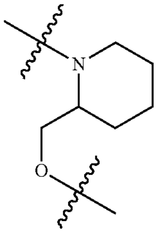, and 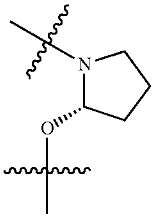;

and each of $R^2$ and $R^3$ is independently selected from the group consisting of $C_{1-10}$ alkyl, $C_{3-12}$ cycloalkyl, $C_{6-12}$ aryl, 5- to 10-membered cyclic heteroaryl, $C_{2-10}$ alkenyl, $C_{2-10}$ alkynyl, and $C_{2-10}$ alkoxy.

2. The 14-chloro-β-elemene nitric oxide donor derivative, or a pharmaceutically acceptable salt, a solvate, an enantiomer, or a diastereoisomer thereof of claim 1, wherein in formula (I):

each of $R^2$ and $R^3$ is independently selected from the group consisting of $C_{2-6}$ alkyl, $C_{2-6}$ alkenyl, and $C_{2-6}$ alkynyl.

3. The 14-chloro-β-elemene nitric oxide donor derivative, or a pharmaceutically acceptable salt, a solvate, an enantiomer, or a diastereoisomer thereof of claim 1, wherein in formula (I):

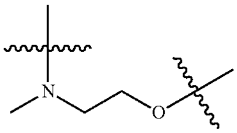, 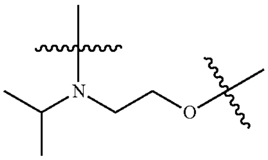,

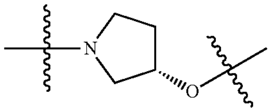,

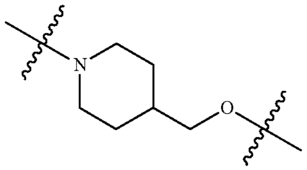,

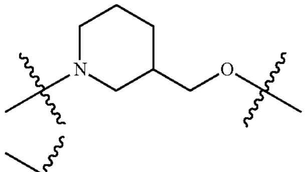,

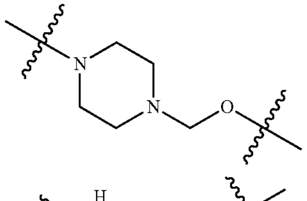,

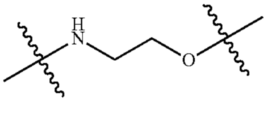,

-continued

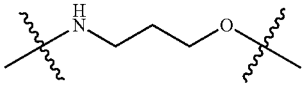,

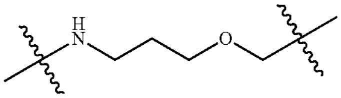,

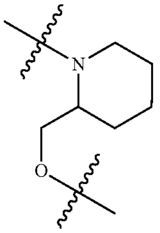, and 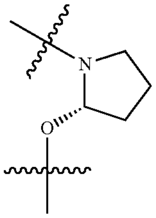;

each of $R^2$ and $R^3$ is independently any one selected from the group consisting of $—CH_2CH_2—$, $—CH_2CH_2CH_2—$, $—CH_2CH_2CH_2CH_2—$, $—CH_2CH_2CH_2CH_2CH_2—$, $—CH{=}CH—$, $—CH_2CH{=}CH—$, $—CH{=}CHCH_2—$, $—CH_2CH{=}CHCH_2—$, $—CH_2CH_2CH{=}CH—$, $—CH{=}CHCH_2CH_2—$, $—CH_2C{\equiv}C—$, $—C{\equiv}CCH_2—$, $—CH_2C{\equiv}CCH_2—$, $—CH_2CH_2C{\equiv}CCH_2—$, $—CH_2CH_2C{\equiv}CCH_2CH_2—$, and $—CH_2C{\equiv}CCH_2CH_2—$.

4. The 14-chloro-β-elemene nitric oxide donor derivative, or a pharmaceutically acceptable salt, a solvate, an enantiomer, or a diastereoisomer thereof of claim 1, wherein the 14-chloro-β-elemene nitric oxide donor derivative is any one selected from the group consisting of compounds having a structure shown in formulas I-1 to I-6:

I-1

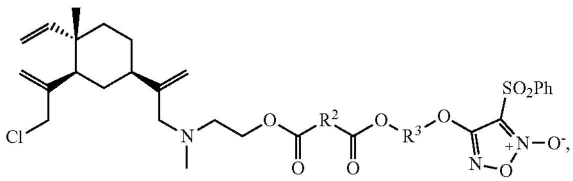,

I-2

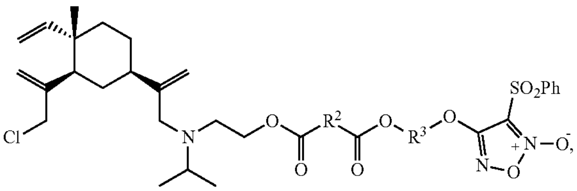,

I-3

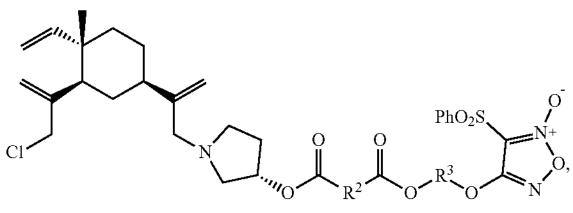,

-continued

I-4

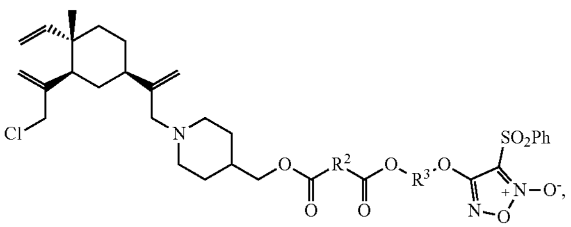

I-5

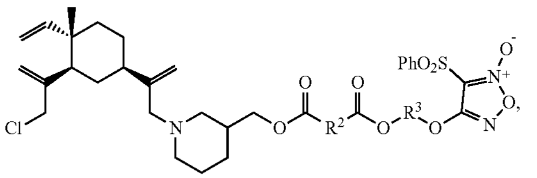

and

-continued

I-6

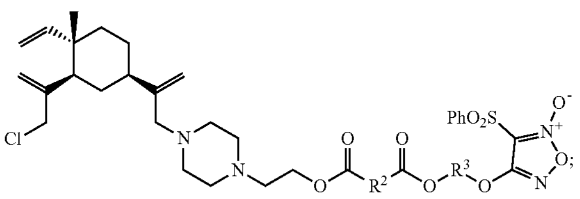

and in the formulas I-1 to I-6, each of $R^2$ and $R^3$ is independently any one selected from the group consisting of $C_{2-6}$ alkyl, $C_{2-6}$ alkenyl, and $C_{2-6}$ alkynyl.

5. The 14-chloro-β-elemene nitric oxide donor derivative, or a pharmaceutically acceptable salt, a solvate, an enantiomer, or a diastereoisomer thereof of claim 1, wherein the 14-chloro-β-elemene nitric oxide donor derivative is any one selected from the group consisting of compounds having a structure shown in formulas 1 to 24:

1

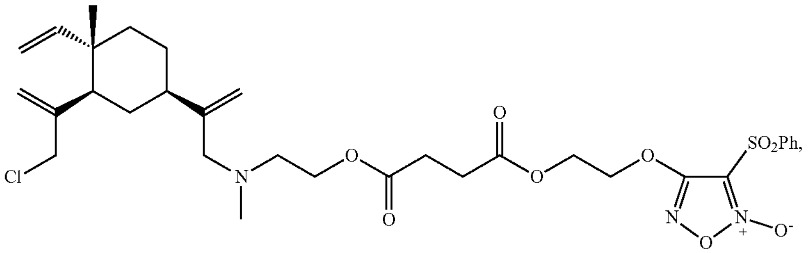

2

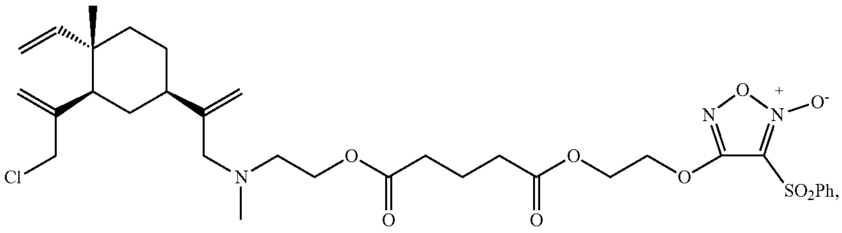

3

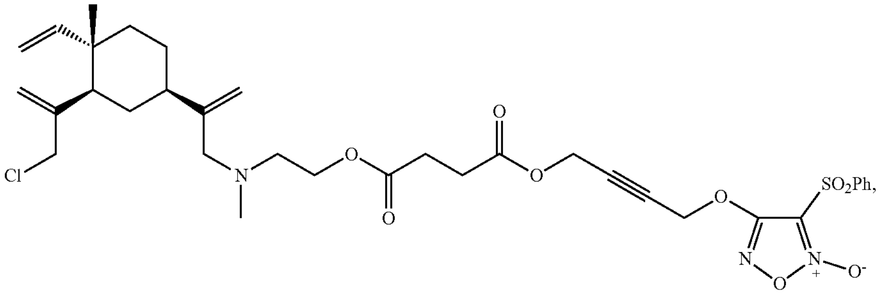

4

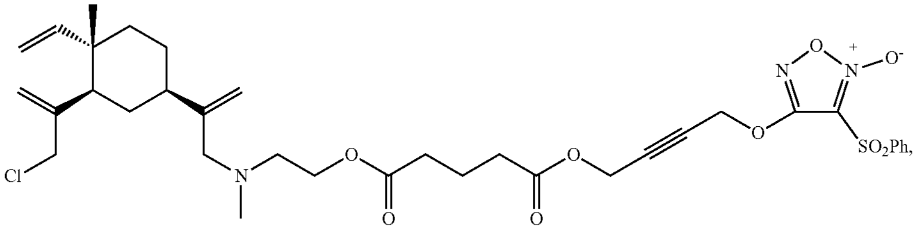

-continued
5
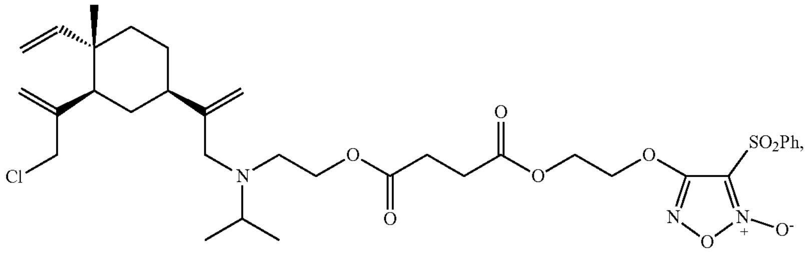
6
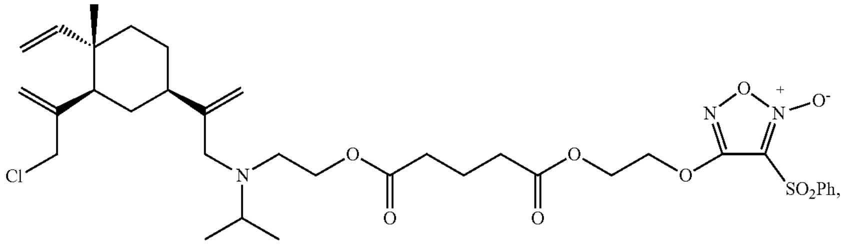
7
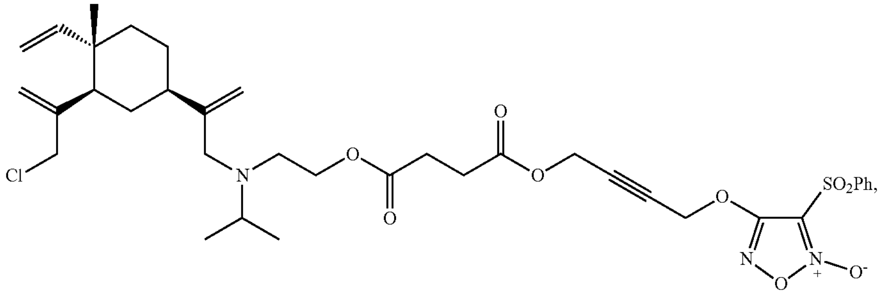
8
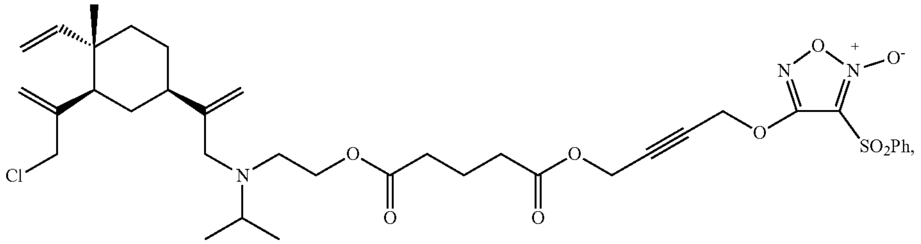
9
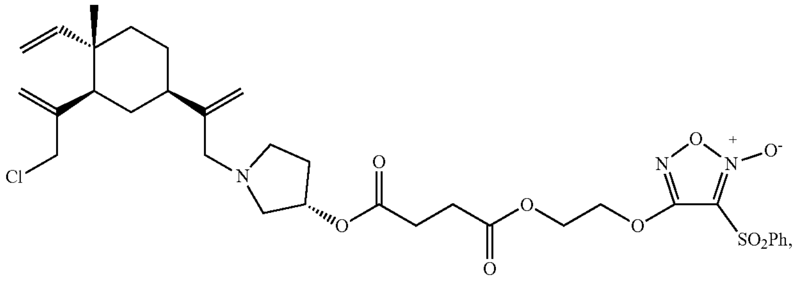

-continued
10
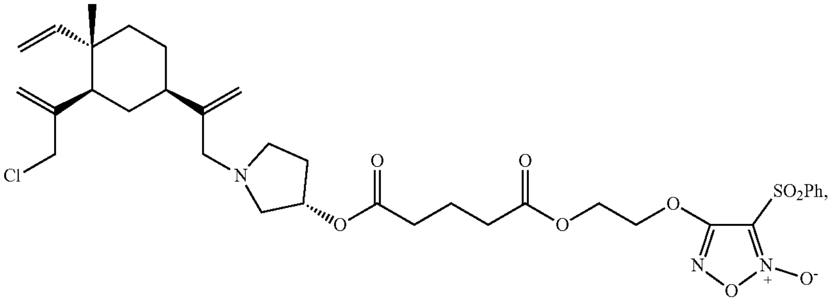
11
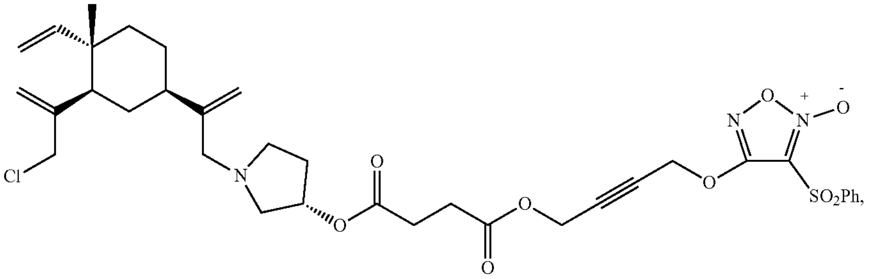
12
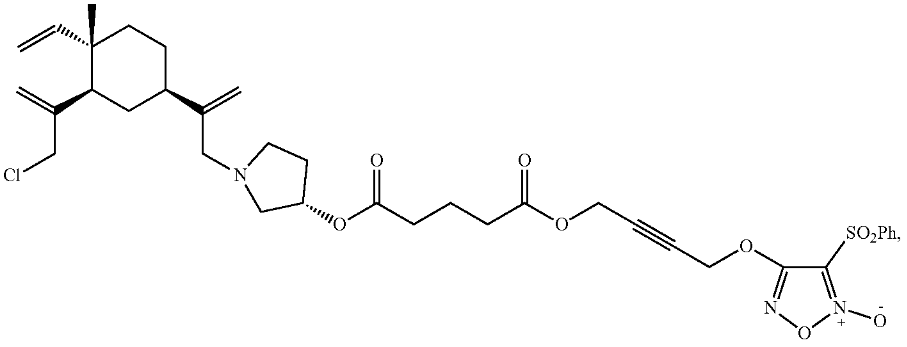
13
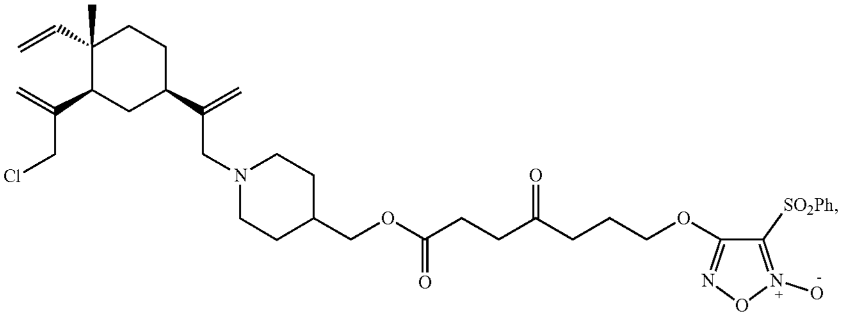
14
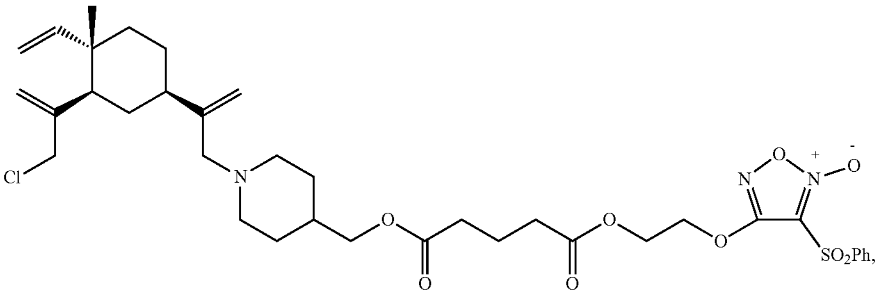

-continued
15
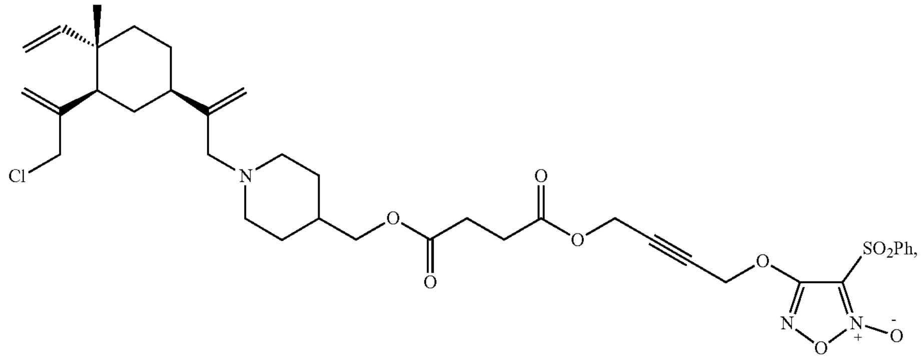
16
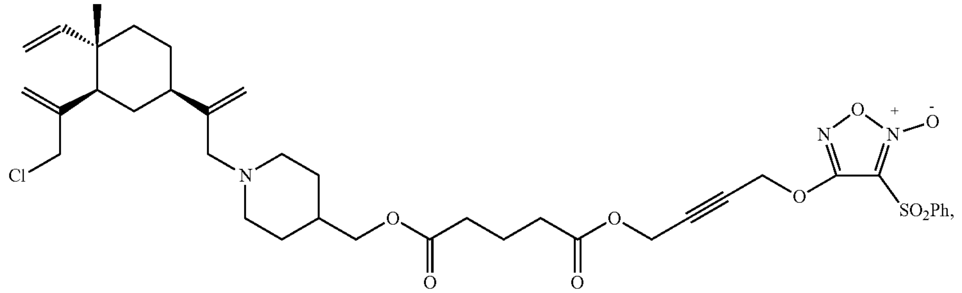
17
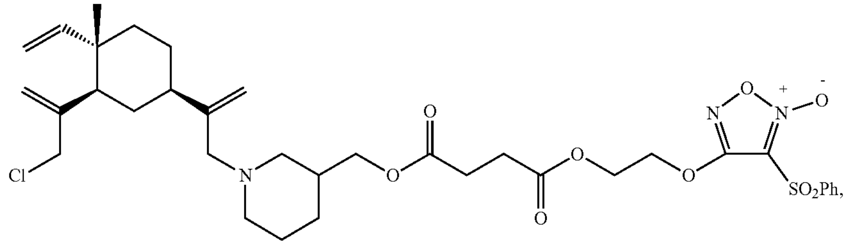
18
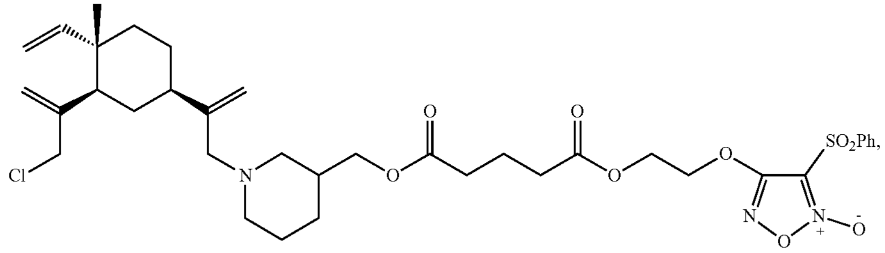
19
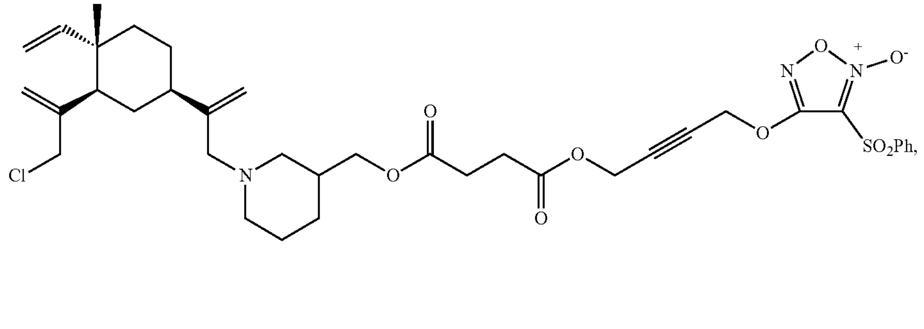

-continued
20
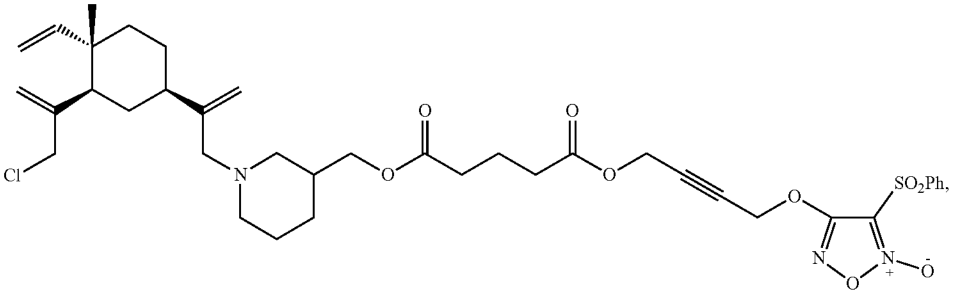
21
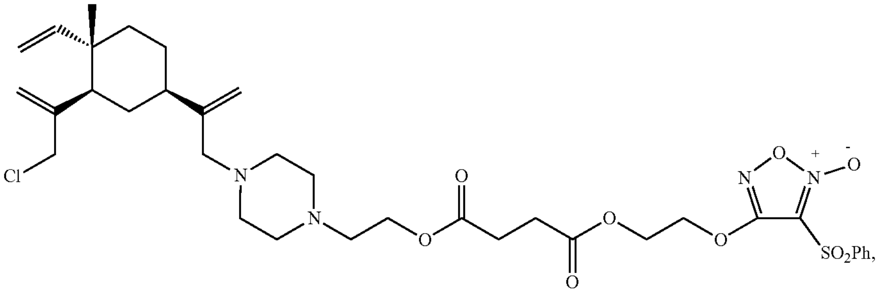
22
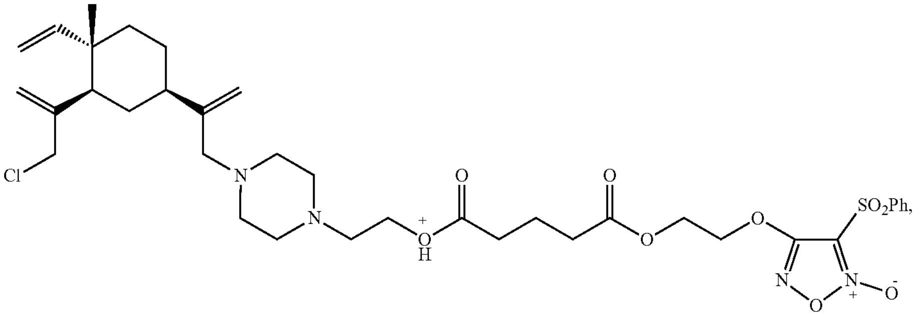
23
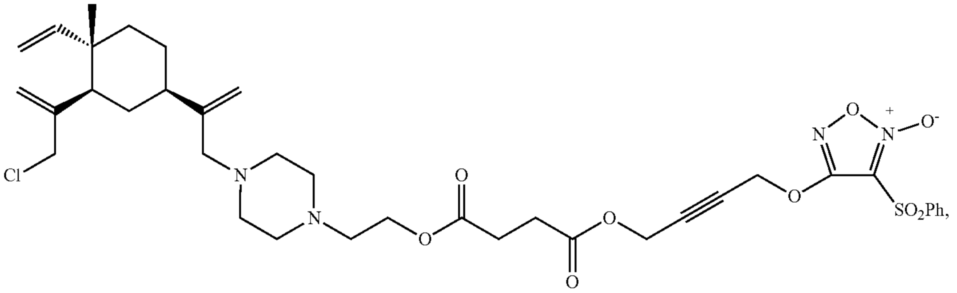
and
24
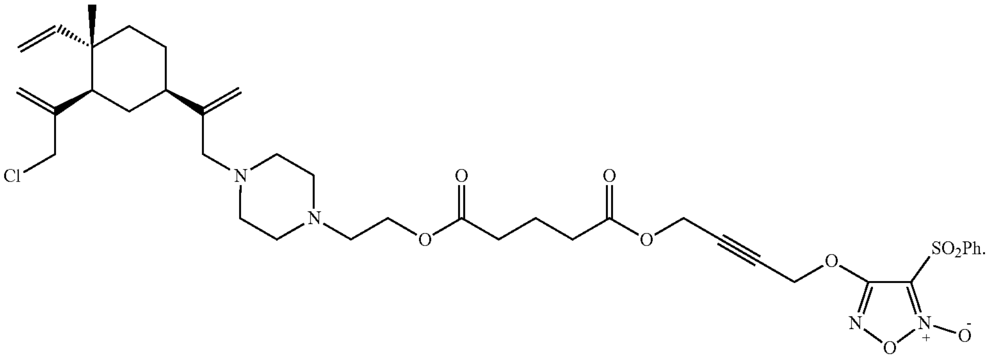

6. A method for treating a tumor, wherein the tumor is lung cancer, colon cancer or malignant brain glioma; comprising administering the 14-chloro-β-elemene nitric oxide donor derivative, or a pharmaceutically acceptable salt, a solvate, an enantiomer, or a diastereoisomer thereof of claim 1 to a subject in need thereof.

7. The method of claim 6, wherein in formula (I):

$R^1$ represents a linear $C_{2-5}$ alcohol amine structure containing nitrogen and oxygen atoms or a cyclic $C_{5-6}$ alcohol amine structure containing nitrogen and oxygen atoms; and each of $R^2$ and $R^3$ is independently selected from the group consisting of $C_{2-6}$ alkyl, $C_{2-6}$ alkenyl, and $C_{2-6}$ alkynyl.

8. The method of claim 6, wherein in formula (I):

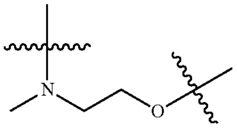
,
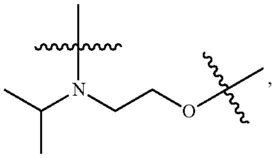
,
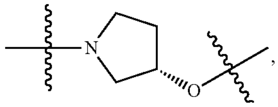
,
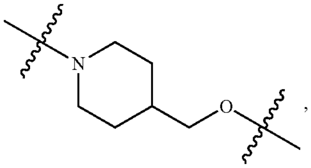
,
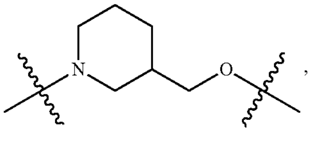
,
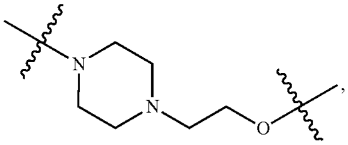
,
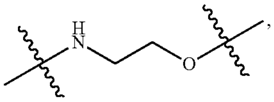
,
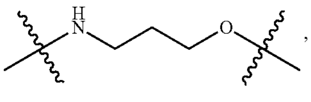
,
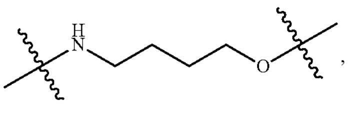
,
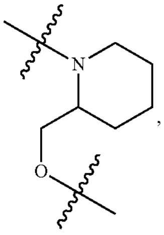
, and -continued

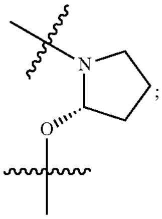
;

each of $R^2$ and $R^3$ is independently and one selected from the group consisting of $—CH_2CH_2—$, $—CH_2CH_2CH_2—$, $—CH_2CH_2CH_2CH_2—$, $—CH_2CH_2CH_2CH_2CH_2—$, $—CH{=}CH—$, $—CH_2CH{=}CH—$, $—CH$ $=CHCH_2—$, $—CH_2CH{=}CHCH_2—$, $—CH_2CH_2CH{=}CH—$, $—CH{=}CHCH_2CH_2—$, $—CH_2C{\equiv}C—$, $—C{\equiv}CCH_2—$, $—CH_2C{\equiv}CCH_2—$, $—CH_2CH_2C{\equiv}CCH_2—$, $—CH_2CH_2C{\equiv}CCH_2CH_2—$, and $—CH_2C{\equiv}CCH_2CH_2—$.

9. The method of claim 6, wherein the 14-chloro-β-elemene nitric oxide donor derivative is any one selected from the group consisting of compounds having a structure shown in formulas I-1 to I-6:

I-1

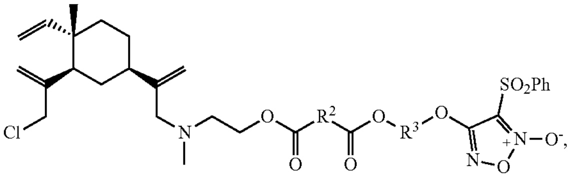

I-2

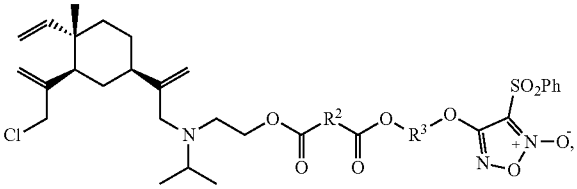

I-3

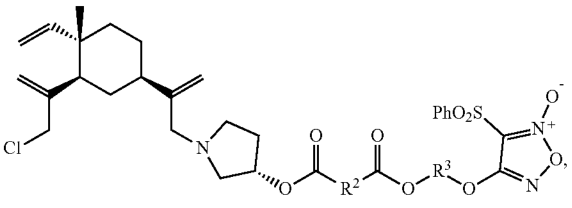

I-4

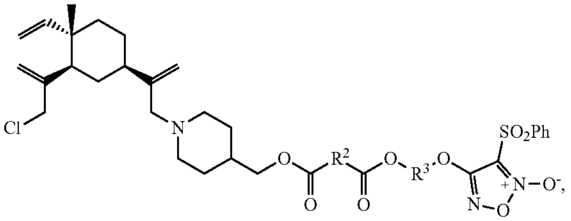

-continued
I-5
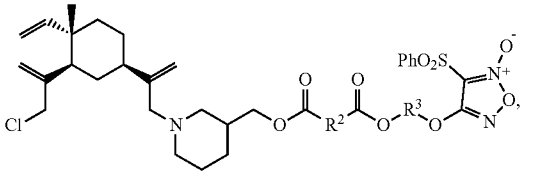
and
-continued
I-6
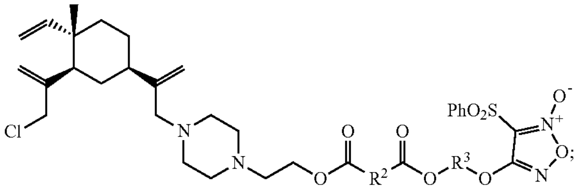
and
in the formulas I-1 to I-6, each of $R^2$ and $R^3$ is independently any one selected from the group consisting of $C_{2-6}$ alkyl, $C_{2-6}$ alkenyl, and $C_{2-6}$ alkynyl.
10. The method of claim 6, wherein the 14-chloro-β-elemene nitric oxide donor derivative is any one selected from the group consisting of compounds having a structure shown in formulas 1 to 24:
1
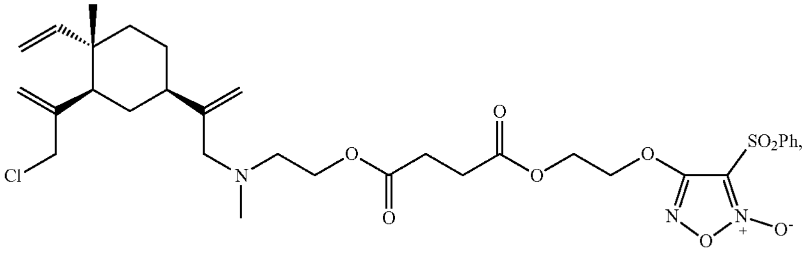
2
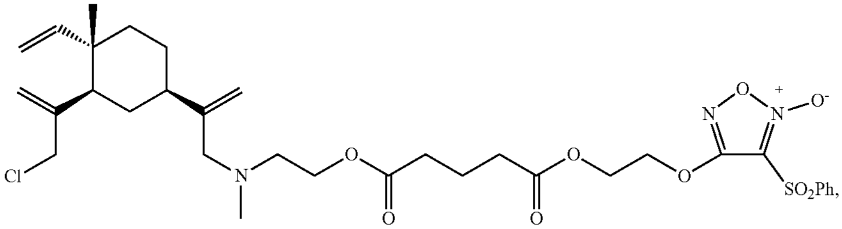
3
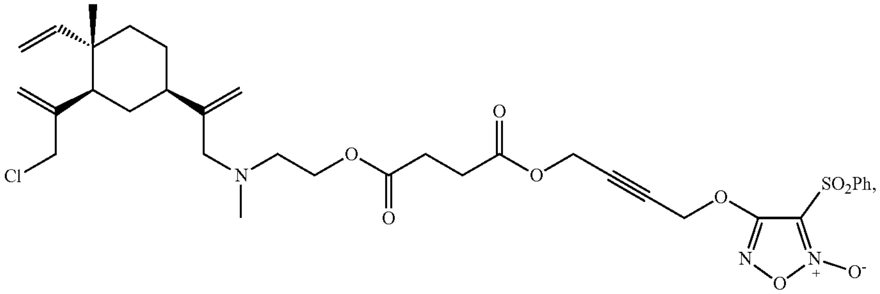
4
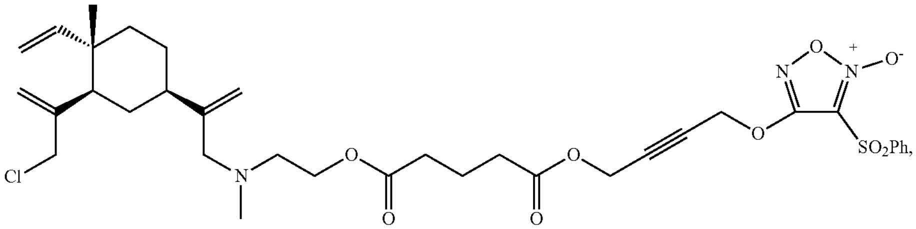

-continued
5
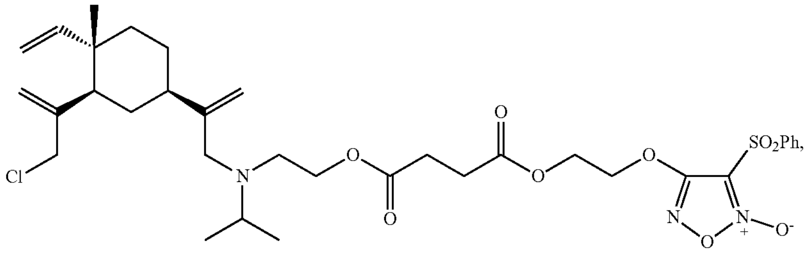
6
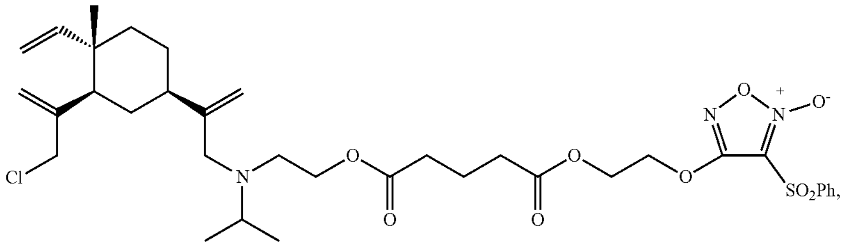
7
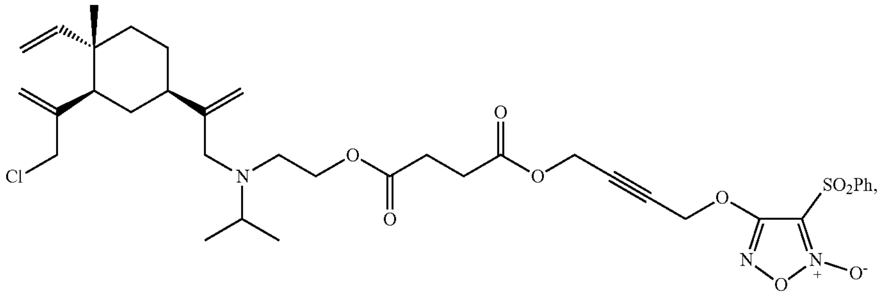
8
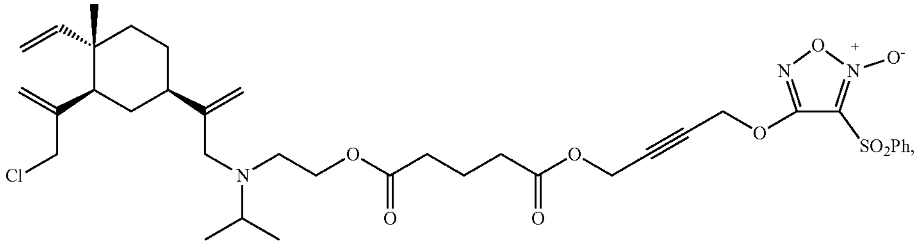
9
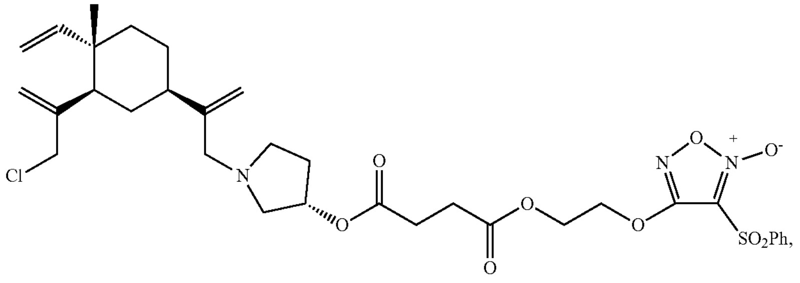

-continued
10
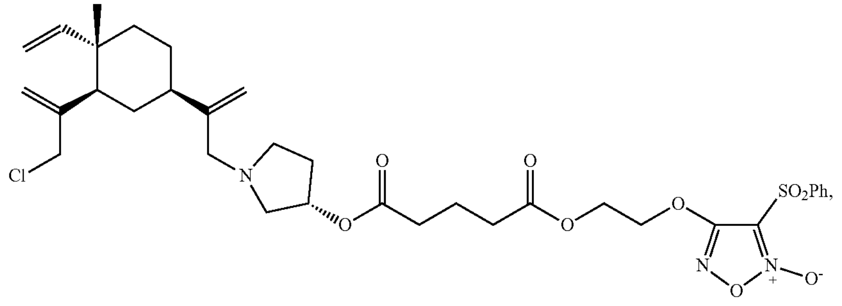
11
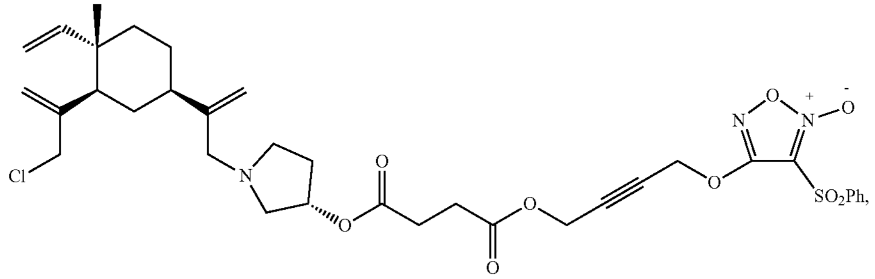
12
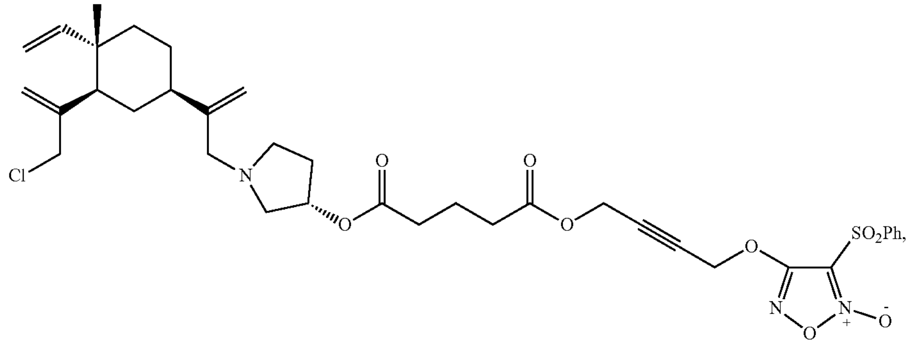
13
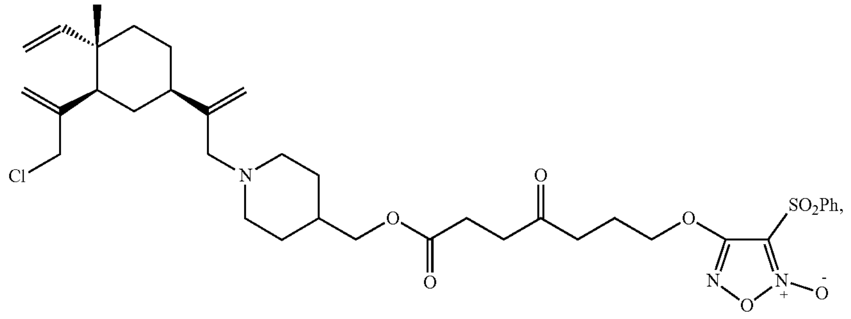
14
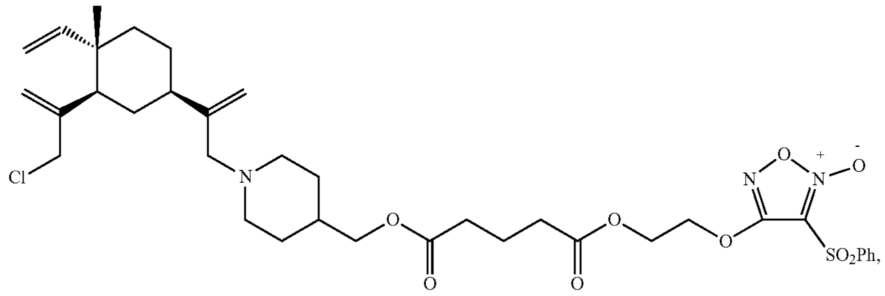

-continued
15
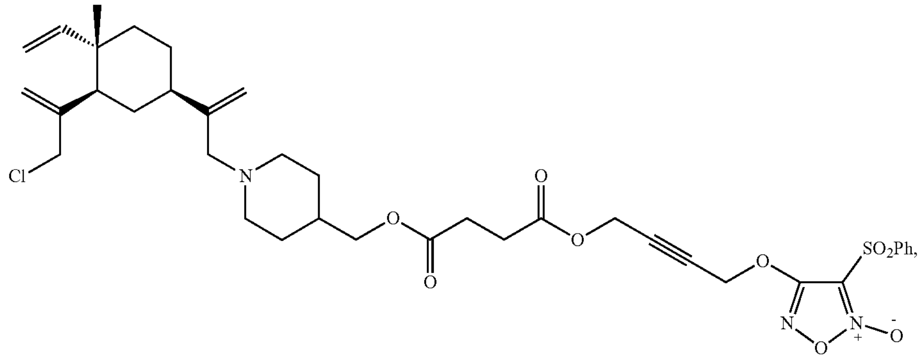
16
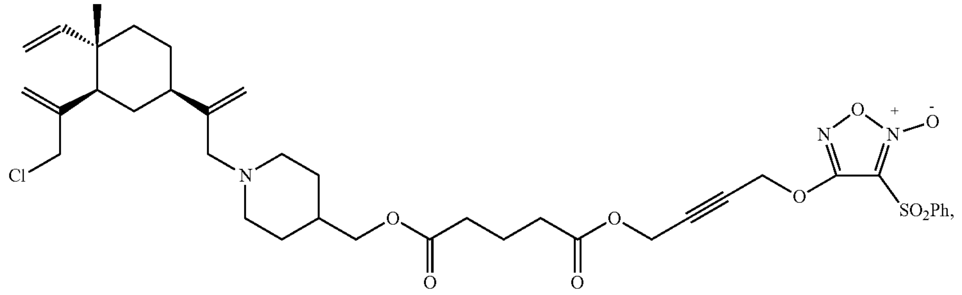
17
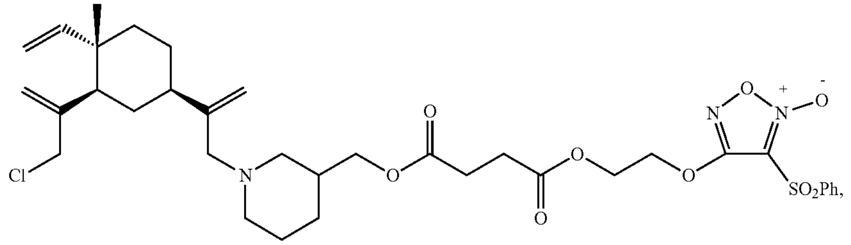
18
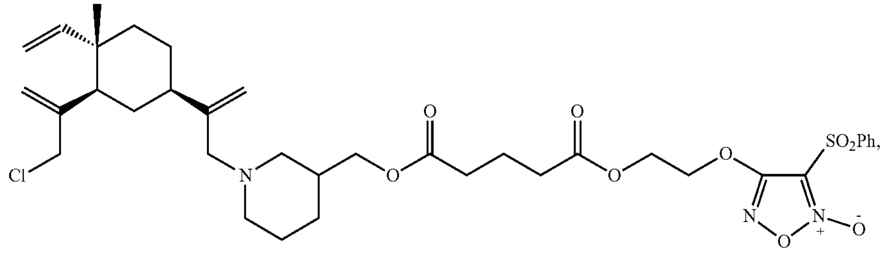
19
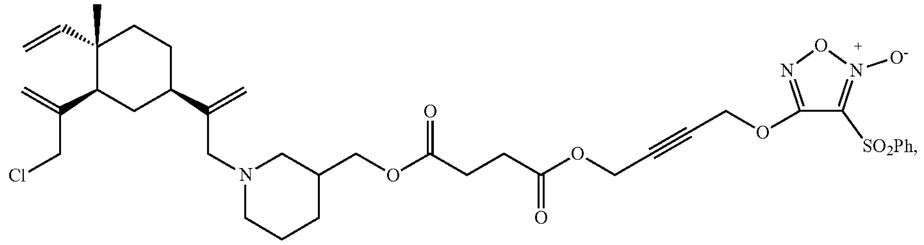

-continued
20
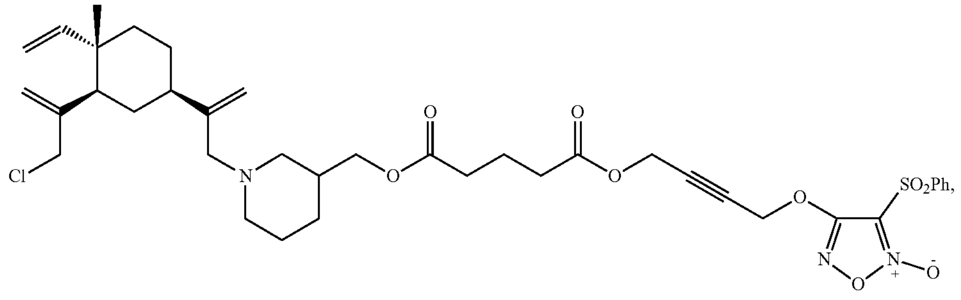
21
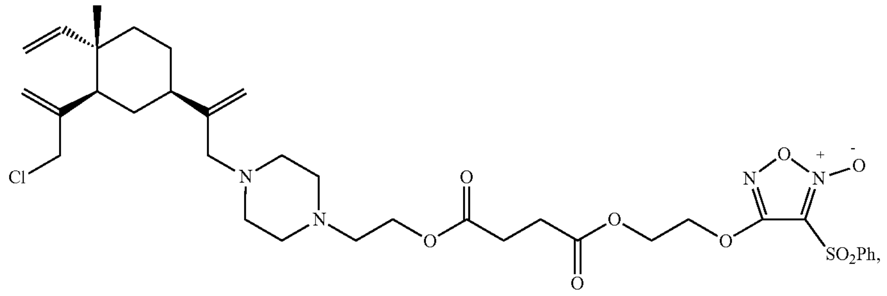
22
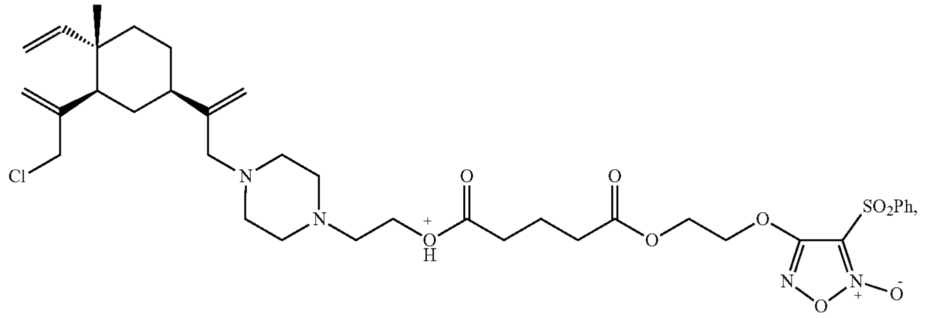
23
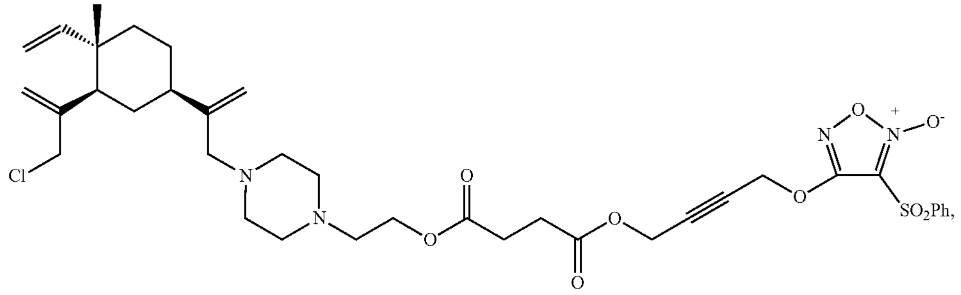
and
24
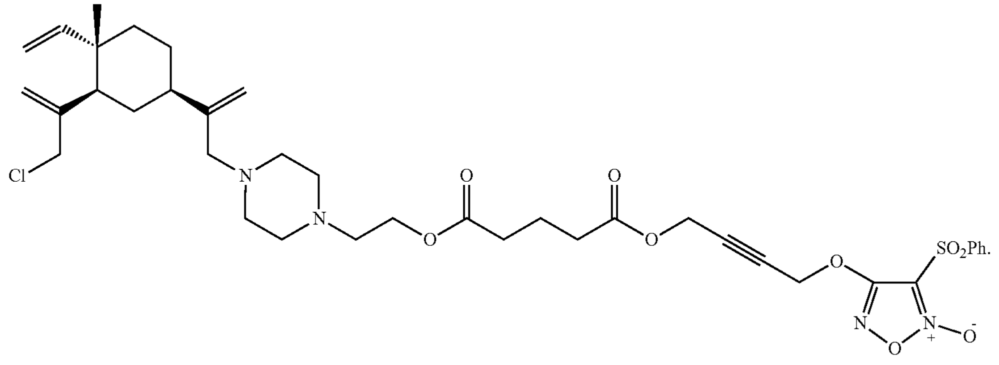
* * * * *